US011587645B2

(12) United States Patent
Amimeur et al.

(10) Patent No.: US 11,587,645 B2
(45) Date of Patent: Feb. 21, 2023

(54) GENERATION OF PROTEIN SEQUENCES USING MACHINE LEARNING TECHNIQUES

(71) Applicant: Just-Evotec Biologies, Inc., Seattle, WA (US)

(72) Inventors: Tileli Amimeur, Seattle, WA (US); Randal Robert Ketchem, Snohomish, WA (US); Jeremy Martin Shaver, Lake Forest Park, WA (US); Rutilio H. Clark, Bainbridge Island, WA (US); John Alex Taylor, Bellevue, WA (US)

(73) Assignee: Just-Evotec Biologics, Inc., Seattle, WA (US)

( * ) Notice: Subject to any disclaimer, the term of this patent is extended or adjusted under 35 U.S.C. 154(b) by 0 days.

(21) Appl. No.: 17/612,918

(22) PCT Filed: May 19, 2020

(86) PCT No.: PCT/US2020/033646
§ 371 (c)(1),
(2) Date: Nov. 19, 2021

(87) PCT Pub. No.: WO2020/236839
PCT Pub. Date: Nov. 26, 2020

(65) Prior Publication Data
US 2022/0230710 A1    Jul. 21, 2022

Related U.S. Application Data

(60) Provisional application No. 63/006,683, filed on Apr. 7, 2020, provisional application No. 62/935,980, filed on Nov. 15, 2019, provisional application No. 62/849,897, filed on May 19, 2019.

(51) Int. Cl.
| | | |
|---|---|---|
| *G16B 40/20* | (2019.01) | |
| *G16B 20/30* | (2019.01) | |
| *G06N 3/12* | (2006.01) | |
| *G06N 3/123* | (2023.01) | |

(52) U.S. Cl.
CPC ............. *G16B 40/20* (2019.02); *G06N 3/123* (2013.01); *G16B 20/30* (2019.02)

(58) Field of Classification Search
None
See application file for complete search history.

(56) References Cited

U.S. PATENT DOCUMENTS

2019/0018019 A1   1/2019 Shan et al.

FOREIGN PATENT DOCUMENTS

| CA | 3132181 A1 | 11/2020 |
|---|---|---|
| CN | 108595916 A | 9/2018 |
| WO | WO-2005072112 A2 | 8/2005 |
| WO | WO-2020225693 A1 * | 11/2020 ............... G06N 3/02 |
| WO | WO-2020236839 A2 | 11/2020 |
| WO | WO-2020236839 A3 | 6/2021 |

OTHER PUBLICATIONS

Creswell et al. Generative Adversarial Networks IEEE Signal Processing Magazine pp. 53-65 (Year: 2018).*
"International Application Serial No. PCT/US2020/033646, International Preliminary Report on Patentability dated Dec. 2, 2021", 8 pgs.
"New Zealand Application Serial No. 782696, First Examiner Report dated Feb. 15, 2022", 5 pgs.
"Canadian Application Serial No. 3,141,476, Office Action dated Feb. 4, 2022", 6 pgs.
"International Application Serial No. PCT/US2020/033646, International Search Report dated Aug. 26, 2020", 2 pgs.
"International Application Serial No. PCT/US2020/033646, Written Opinion dated Aug. 26, 2020", 9 pgs.
Amimeur, T, et al., "Designing Feature-Controlled Humanoid Antibody Discovery Libraries Using Generative Adversarial Networks", bioRxiv., (Apr. 23, 2020), 1-35.
Gupta, A, et al., "Feedback GAN (FBGAN) for DNA: a Novel Feedback-Loop Architecture for Optimizing Protein Functions", arXiv:1804.01694 [q-bio.GN], 1-15.
"European Application Serial No. 20809685.9, Response filed Sep. 21, 2022 to Communication Pursuant to Article 94(3) EPC dated Jun. 3, 2022", 23 pgs.
"Canadian Application Serial No. 3,141,476, Response filed Jun. 1, 2022 to Office Action dated Feb. 4, 2022", 19 pgs.
"European Application Serial No. 20809685.9, Communication Pursuant to Article 94(3) EPC dated Jun. 3, 2022", 7 pgs.
"European Application Serial No. 20809685.9, Extended European Search dated May 19, 2022", 4 pgs.
Daskalakis, Constantinos, et al., "Training GANs with Optimism", [online], [retrieved on May 10, 2022], ARXIV.Org, 201 Olin Library Cornell University, Ithaca, NY 14853, Retrieved from the Internet: <URL:https://arxiv.org/abs/1711.00141>, (Oct. 31, 2017), 1-30.

(Continued)

*Primary Examiner* — John S Brusca
(74) *Attorney, Agent, or Firm* — Schwegman Lundberg & Woessner, P.A.

(57) ABSTRACT

Amino acid sequences of antibodies can be generated using a generative adversarial network that includes a first generating component that generates amino acid sequences of antibody light chains and a second generating component generates amino acid sequences of antibody heavy chains. Amino acid sequences of antibodies can be produced by combining the respective amino acid sequences produced by the first generating component and the second generating component. The training of the first generating component and the second generating component can proceed at different rates. Additionally, the antibody amino acids produced by combining amino acid sequences from the first generating component and the second generating component may be evaluated according to complentarity-determining regions of the antibody amino acid sequences. Training datasets may be produced using amino acid sequences that correspond to antibodies have particular binding affinities with respect to molecules, such as binding affinity with major histocompatibility complex (MHC) molecules.

16 Claims, 16 Drawing Sheets

(56) References Cited

OTHER PUBLICATIONS

Gupta, Anvita, et al., "Feedback GAN for DNA optimizes protein functions", Nature *Machine Intelligence*, vol. 1, No. 2, (Feb. 11, 2019), 105-111.
"New Zealand Application Serial No. 782696, Response filed Aug. 11, 2022 to First Examiner Report dated Feb. 15, 2022", 137 pgs.

\* cited by examiner

GENERATION OF PROTEIN SEQUENCES USING MACHINE LEARNING TECHNIQUES

PRIORITY INFORMATION

This application is a U.S. national stage filing under 35 U.S.C. § 371 from International Application No. PCT/US2020/033646, filed on May 19, 2020, and published as WO2020/236839 A2 on Nov. 26, 2020, which claims benefit of priority to the filing date of U.S. Provisional Application Ser. No. 62/849,897, filed May 19, 2019, and U.S. Provisional Application Ser. No. 62/935,980, filed Nov. 15, 2019 and U.S. Provisional Application Ser. No. 63/006,683, filed Apr. 7, 2020, the contents of which applications are specifically incorporated by reference herein in their entireties.

BACKGROUND

Proteins are biological molecules that are comprised of one or more chains of amino acids. Proteins can have various functions within an organism. For example, some proteins can be involved in causing a reaction to take place within an organism. In other examples, proteins can transport molecules throughout the organism. In still other examples, proteins can be involved in the replication of genes. Additionally, some proteins can have therapeutic properties and be used to treat various biological conditions. The structure and function of proteins are based on the arrangement of amino acids that comprise the proteins. The arrangement of amino acids for proteins can be represented by a sequence of letters with each letter corresponding to an amino acid at a certain position. The arrangement of amino acids for proteins can also be represented by three dimensional structures that not only indicate the amino acids at certain positions of the protein, but also indicate three dimensional features of the proteins, such as an α-helix or a β-sheet.

BRIEF DESCRIPTION OF THE DRAWINGS

The present disclosure is illustrated by way of example and not limitation in the figures of the accompanying drawings, in which like references indicate similar elements.

DETAILED DESCRIPTION

Figure 1:
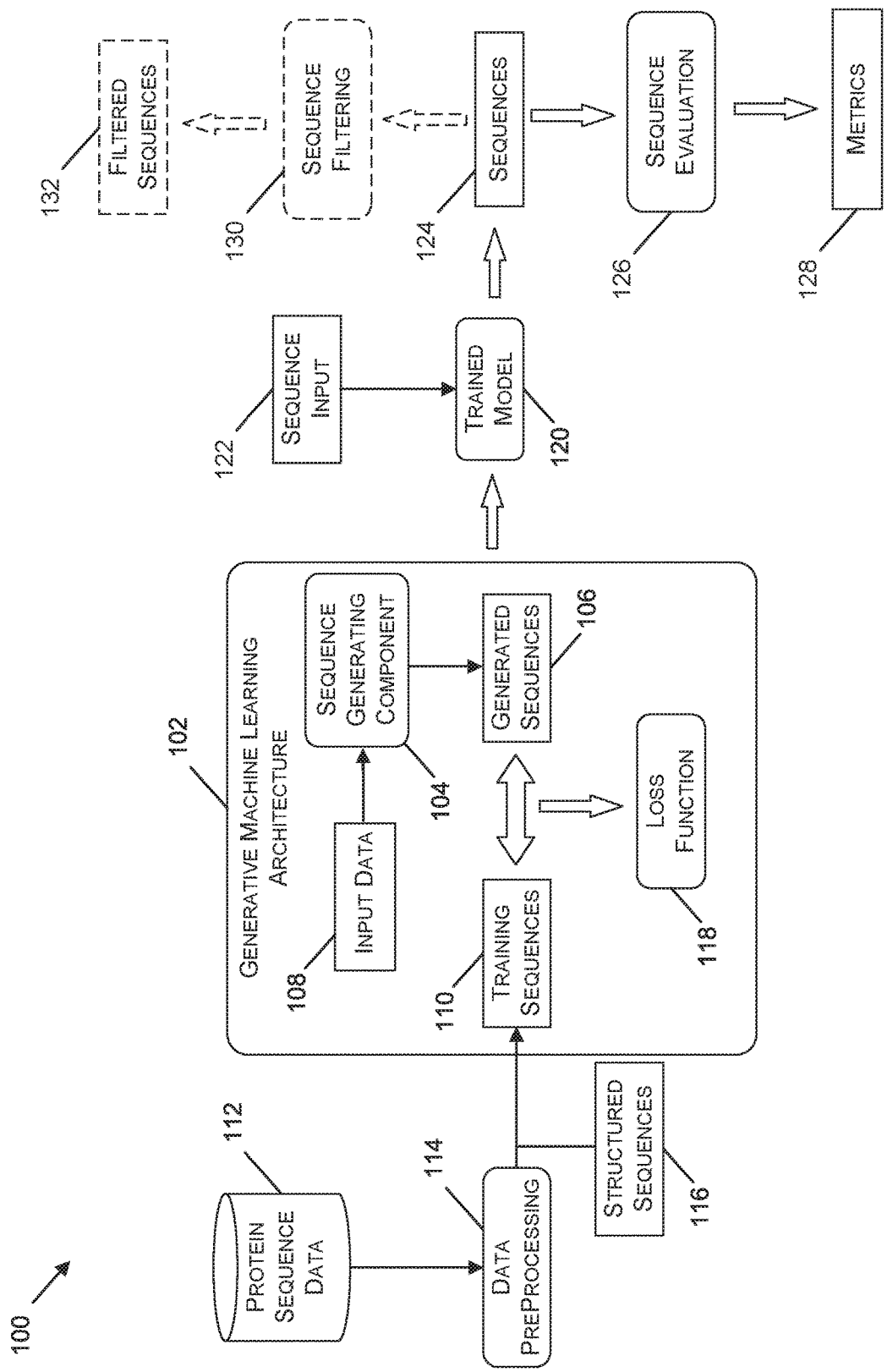
FIG. 1 is a diagram illustrating an example framework to generate protein sequences, in accordance with some implementations.

Proteins can have many beneficial uses within organisms. In particular situations, proteins can be used to treat diseases and other biological conditions that can detrimentally impact the health of humans and other mammals. In various scenarios, proteins can participate in reactions that are beneficial to subjects and that can counteract one or more biological conditions being experienced by the subjects. In some examples, proteins can also bind to target molecules within an organism that may be detrimental to the health of a subject. For these reasons, many individuals and organizations have sought to develop proteins that may have therapeutic benefits.

The development of proteins can be a time consuming and resource intensive process. Often, candidate proteins for development can be identified as potentially having desired biophysical properties, three-dimensional (3D) structures, and/or behavior within an organism. In order to determine whether the candidate proteins actually have the desired characteristics, the proteins can be synthesized and then tested to determine whether the actual characteristics of the synthesized proteins correspond to the desired characteristics. Due to the amount of resources needed to synthesize and test proteins for specified biophysical properties, 3D structures, and/or behaviors, the number of candidate proteins synthesized for therapeutic purposes is limited. In some situations, the number of proteins synthesized for therapeutic purposes can be limited by the loss of resources that takes place when candidate proteins are synthesized and do not have the desired characteristics.

The use of computer-implemented techniques to identify candidate proteins that have particular characteristics has increased. These conventional techniques, however, can be limited in their scope and accuracy. In various situations, conventional computer-implemented techniques to generate protein sequences can be limited by the amount of data available and/or the types of data available that may be needed by those conventional techniques to accurately generate protein sequences with specified characteristics. Additionally, the techniques utilized to produce models that can generate protein sequences with particular characteristics can be complex and the know-how needed to produce models that are accurate and efficient can be complex. In certain scenarios, the length of the protein sequences produced by conventional models can also be limited because the accuracy of conventional techniques can decrease as the lengths of the proteins increases. Thus, the number of proteins generated by conventional techniques is limited.

The techniques and systems described herein can be used to generate amino acid sequences of proteins accurately and efficiently. In particular implementations, generative adversarial networks can be implemented to determine models that can produce amino acid sequences of proteins. The generative adversarial networks can be trained using a number of different training datasets to produce amino acid sequences for proteins having specified characteristics. For example, the generative adversarial networks described herein can produce sequences of amino acids of proteins having particular biophysical properties. In other examples, the generative adversarial networks described herein can produce sequences of amino acids having a particular structure. Additionally, the techniques and systems described herein can utilize computer-implemented processes that analyze the amino acid sequences generated by the generative adversarial networks. The analysis of the amino acid sequences can determine whether the characteristics of the amino acid sequences produced by the generative adversarial networks correspond to a desired set of characteristics. In particular implementations, the computer-implemented processes can filter amino acid sequences produced by the generative adversarial networks to identify amino acid sequences that correspond to a specified set of characteristics.

In further examples, one or more implementations described herein may include an autoencoder architecture that can generate protein sequences. In one or more examples, a variational autoencoder can be used to generate protein sequences. In various examples, a variational autoencoder can be implemented to generate amino acid sequences of antibodies. In one or more implementations, a generative machine learning architecture can include at least one encoder and a decoder that optimize a loss function to produce a model that generates amino acid sequences that correspond to sequences of proteins. After an initial training of the model, the model can be further modified by training the model using data that corresponds to amino acid sequences of proteins that have a specified set of characteristics, such as one or more specified biophysical properties.

Additionally, the techniques and systems described herein can be used to generate amino acid sequences of antibodies that have at least a threshold probability of binding to a specified antigen. In these scenarios, the amino acid sequences can be generated based on antibody-antigen interaction data indicating interactions between antibodies and antigens. For example, the antibody-antigen interaction data can indicate antigen binding regions of antibodies and the corresponding epitopes of the antigens that are bound to the antigen binding regions of the antibodies.

Further, the techniques and systems described herein can be used to produce amino acid sequences of antibodies using amino acid sequences of antibody heavy chains and of antibody light chains that have been generated separately and then combined. In various implementations, a generative adversarial network using two generating components (one for the heavy chain amino acid sequences and another for the light chain amino acid sequences) can be used to separately produce heavy chain amino acid sequences and light chain amino acid sequences that can then be combined to generate antibody sequences that include both heavy chains and light chains. The implementation of separate generating components to generate light chain amino acid sequences and heavy chain amino acid sequences improves the efficiency of the generative adversarial network and minimizes the computing resources utilized to generate amino acid sequences of antibodies in relation to generative adversarial networks that implement a single generating component to produce both the heavy chain and light chain amino acid sequences of antibodies. That is, fewer computing resources are utilized to produce a number of antibody sequences from combinations of separately generated light chains and heavy chains than the same number of antibody sequences generated as amino acid sequences that are initially generated with both light chains and heavy chains. In addition, the number of overall resources utilized to chemically synthesize a library of light chains and a library of heavy chains that can be combined to produce a number of antibodies based on machine generated light chain sequences and heavy chain sequences as described herein is lower than techniques that simply chemically synthesize antibodies already having both heavy chains and light chains.

FIG. 1 is a diagram illustrating an example framework 100 to generate protein sequences, in accordance with some implementations. The framework 100 can include a generative machine learning architecture 102. The generative machine learning architecture 102 can include a sequence generating component 104. The sequence generating component 104 can implement a model to generate amino acid sequences based on input provided to the sequence generating component 104. For example, the sequence generating component 104 can produce generated sequences 106. The generated sequences 106 can include amino acid sequences of proteins. In one or more examples, the generated sequences 106 can include amino acid sequences of antibodies. In various implementations, the model implemented by the sequence generating component 104 can include one or more functions.

In various implementations, the generative machine learning architecture 102 can implement one or more neural network technologies. For example, the machine learning architecture 102 can implement one or more recurrent neural networks. Additionally, the machine learning architecture 102 can implement one or more convolutional neural networks. In certain implementations, the machine learning architecture 102 can implement a combination of recurrent neural networks and convolutional neural networks. In examples, the machine learning architecture 102 can include a generative adversarial network (GAN). In these situations, the sequence generating component 104 can include a generator and the generative machine learning architecture 102 can also include a challenging component. In further examples, the generative machine learning architecture 102 may include an autoencoder. In one or more illustrative examples, the generative machine learning architecture 102 may include a variational autoencoder. In these scenarios, the sequence generating component 104 may include at least one of an encoder or a decoder of a variational autoencoder.

The generated sequences 106 can be produced by the sequence generating component 104 based on input data 108. In one or more examples, the input data 108 can include one or more amino acid sequences, such as a template protein sequence. The input data 108 may also include an input vector that includes computer-generated noise that is produced by a random noise generator or a pseudo-random noise generator.

The generated sequences 106 may be evaluated with respect to training sequences 110. The training sequences 110 may correspond to amino acid sequences obtained from the protein sequence data 112. The protein sequence data 112 can include sequences of proteins obtained from one or more data sources that store protein amino acid sequences. The protein sequence data 112 may include amino acid sequences of one or more proteins, such as fibronectin type III (FNIII) proteins, avimers, antibodies, VHH domains, kinases, zinc fingers, and the like.

The protein sequences included in the protein sequence data 112 can be subject to data preprocessing 114 before being provided to the generative machine learning architecture 102. In implementations, the protein sequence data 112 can be arranged according to a classification system by the data preprocessing 114 before being provided to the generative machine learning architecture 102. The data preprocessing 114 can include pairing amino acids included in the proteins of the protein sequence data 112 with numerical values that can represent structure-based positions within the proteins. The numerical values can include a sequence of numbers having a starting point and an ending point. In an illustrative example, a T can be paired with the number 43 indicating that a Threonine molecule is located at a structure-based position 43 of a specified protein domain type.

In various implementations, the classification system implemented by the data preprocessing 114 can designate a particular number of positions for certain regions of proteins. For example, the classification system can designate that portions of proteins have particular functions and/or characteristics can have a specified number of positions. In various situations, not all of the positions included in the classification system may be associated with an amino acid because the number of amino acids in a particular region of a protein may vary between proteins. To illustrate, the number of amino acids in a region of a protein can vary for different types of proteins. In additional examples, the structure of a protein can be reflected. In examples, positions of the classification system that are not associated with a particular amino acid can indicate various structural features of a protein, such as a turn or a loop. In an illustrative example, a classification system for antibodies can indicate that heavy chain regions. light chain regions, and hinge regions have a specified number of positions assigned to them and the amino acids of the antibodies can be assigned to the positions according to the classification system.

In implementations, the data included in the protein sequence data 112 used to train the generative machine learning architecture 102 can impact the amino acid sequences produced by the sequence generating component 104. For example, the characteristics, biophysical properties, manufacturing characteristics (e.g., titer, yield, etc.) and so forth, of the protein sequence data 112 can impact characteristics, biophysical properties, and/or manufacturing characteristics of the generated sequences 106 produced by the sequence generating component 104. To illustrate, in situations where antibodies are included in the protein sequence data 112 provided to the generative machine learning architecture 102, the amino acid sequences generated by the sequence generating component 104 can correspond to antibody amino acid sequences. In another example, in scenarios where T-cell receptors are included in the protein sequence data 112 provided to the generative machine learning architecture 102, the amino acid sequences generated by the sequence generating component 104 can correspond to T-cell receptor amino acid sequences. In an additional example, in situations where kinases are included in the protein sequence data 112 provided to the generative machine learning architecture 102, the amino acid sequences generated by the sequence generating component 104 can correspond to amino acid sequences of kinases. In implementations where amino acid sequences of a variety of different types of proteins are included in the protein sequence data 112 provided to the generative machine learning architecture 102, the sequence generating component 104 can generate amino acid sequences having characteristics of proteins generally and may not correspond to a particular type of protein.

The output produced by the data preprocessing 114 can include structured sequences 116. The structured sequences 116 can include a matrix indicating amino acids associated with various positions of a protein. In examples, the structured sequences 116 can include a matrix having columns corresponding to different amino acids and rows that correspond to structure-based positions of proteins. For each element in the matrix, a 0 can be used to indicate the absence of an amino acid at the corresponding position and a 1 can be used to indicate the presence of an amino acid at the corresponding position. In situations where a position represents a gap in an amino acid sequence, the row associated with the position can comprise zeroes for each column. The generated sequence(s) 106 can also be represented using a vector according to a same or similar number scheme as used for the structured sequences 116. In some illustrative examples, the structured sequences 116 and the generated sequence(s) 106 can be encoded using a method that may be referred to as a one-hot encoding method.

The generative machine learning architecture 102 may analyze the generated sequences 106 with respect to the training sequences 110 to evaluate a loss function 118 of the generative machine learning architecture 102. In one or more examples, output of the loss function 118 can be used to modify the sequences generated by the sequence generating component 104. For example, output related to the loss function 118 can be used to modify one or more components of the generative machine learning architecture 102, such as an encoder, a decoder, and/or a generator of a GAN, to produce generated sequences 106 that correspond more closely to the training sequences 110. In one or more examples, components of the generative machine learning architecture 102 may be modified to optimize the loss function 118. In various examples, components of the generative machine learning architecture 102 can be modified to minimize the loss function 118.

After the generative machine learning architecture 102 has undergone a training process, a trained model 120 can be generated that can produce sequences of proteins. The trained model 120 can include one or more components of the generative machine learning architecture 102 after a training process using the protein sequence data 112. In one or more implementations, the trained model 120 can include a generator of a GAN that has been trained using the protein sequence data 112. Additionally, the trained model 120 can include at least one of an encoder or a decoder of an autoencoder that has been trained using the protein sequence data 112. In examples, the training process for the generative machine learning architecture 102 can be complete after the function(s) implemented by one or more components of the generative machine learning architecture 102 converge. The convergence of a function can be based on the movement of values of model parameters toward particular values as protein sequences are generated by the sequence generating component 104 and feedback is obtained in relation to the loss function 118 based on differences between the training sequences 110 and the generated sequences 106.

In various implementations, the training of the generative machine learning architecture 102 can be complete when the protein sequences generated by the sequence generating component 104 have particular characteristics. To illustrate, the amino acid sequences generated by the sequence generating component 104 can be analyzed by a software tool that can analyze amino acid sequences to determine at least one of biophysical properties of the amino acid sequences, structural features of the amino acid sequences, or adherence to amino acid sequences corresponding to one or more protein germlines. As used herein, germline, can correspond to amino acid sequences of proteins that are conserved when cells of the proteins replicate. An amino acid sequence can be conserved from a parent cell to a progeny cell when the amino acid sequence of the progeny cell has at least a threshold amount of identity with respect to the corresponding amino acid sequence in the parent cell. In an illustrative example, a portion of an amino acid sequence of a human antibody that is part of a kappa light chain that is conserved from a parent cell to a progeny cell can be a germline portion of the antibody.

Sequence input 122 can be provided to the trained model 120, and the trained model 120 can produce sequences 124. The sequence input 122 can correspond to random or pseudo-random series of numbers that can be used to produce the sequences 124 that can include amino acid sequences of proteins. The sequences 124 produced by the trained model 120 can be represented as a matrix structure that is the same as or similar to the matrix structure used to represent the structured sequences 116 and the generated sequence(s) 106. In various implementations, the matrices produced by the trained model 120 that comprise the sequences 124 can be decoded to produce a string of amino acids that correspond to the sequence of a protein. At operation 126, the sequences 124 can be evaluated to determine whether the sequences 124 have a specified set of characteristics. The sequence evaluation performed at operation 126 can produce metrics 128 that indicate characteristics of the sequences 124. Additionally, the metrics 128 can indicate an amount of correspondence between the characteristics of the sequences 124 and a specified set of characteristics. In some examples, the metrics 128 can indicate a number of positions of an amino acid sequence 124 that vary from an amino acid sequence of a protein produced from a germline gene.

The sequences 124 produced by the model 120 can correspond to various types of proteins. For examples, the sequences 124 can correspond to proteins that function as T-cell receptors. In additional examples, the sequences 124 can correspond to proteins that function as catalysts to cause biochemical reactions within an organism to take place. The sequences 124 can also correspond to one or more types of antibodies. To illustrate, the sequences 124 can correspond to one or more antibody subtypes, such as immunoglobin A (IgA), immunoglobin D (IgD), immunoglobin E (IgE), immunoglobin G (IgG), or immunoglobin M (IgM). Further, the sequences 124 can correspond to additional proteins that bind antigens. In examples, the sequences 124 can correspond to affibodies, affilins, affimers, affitins, alphabodies, anticalins, avimers, monobodies, designed ankyrin repeat proteins (DARPins), nanoCLAMP (clostridal antibody mimetic proteins), antibody fragments, or combinations thereof. In still other examples, the sequences 124 can correspond to amino acid sequences that participate in protein-to-protein interactions, such as proteins that have regions that bind to antigens or regions that bind to other molecules.

In some implementations, the sequences 124 can be subject to sequence filtering at operation 130 to produce one or more filtered sequences 132. The sequence filtering 130 can parse the sequences 124 for one or more of the sequences 124 that correspond to one or more characteristics. For example, the sequence filtering at operation 130 can analyze the sequences 124 to identify sequences 124 that have specified amino acids at particular positions. The sequence filtering 130 can also identify one or more of the sequences 124 that have one or more particular strings of amino acids. In various implementations, the sequence filtering at operation 130 can identify one or more of the sequences 124 that have a set of biophysical properties based on similarities between at least one of the sequences 124 and amino acid sequences of proteins having the set of biophysical properties.

Figure 2:
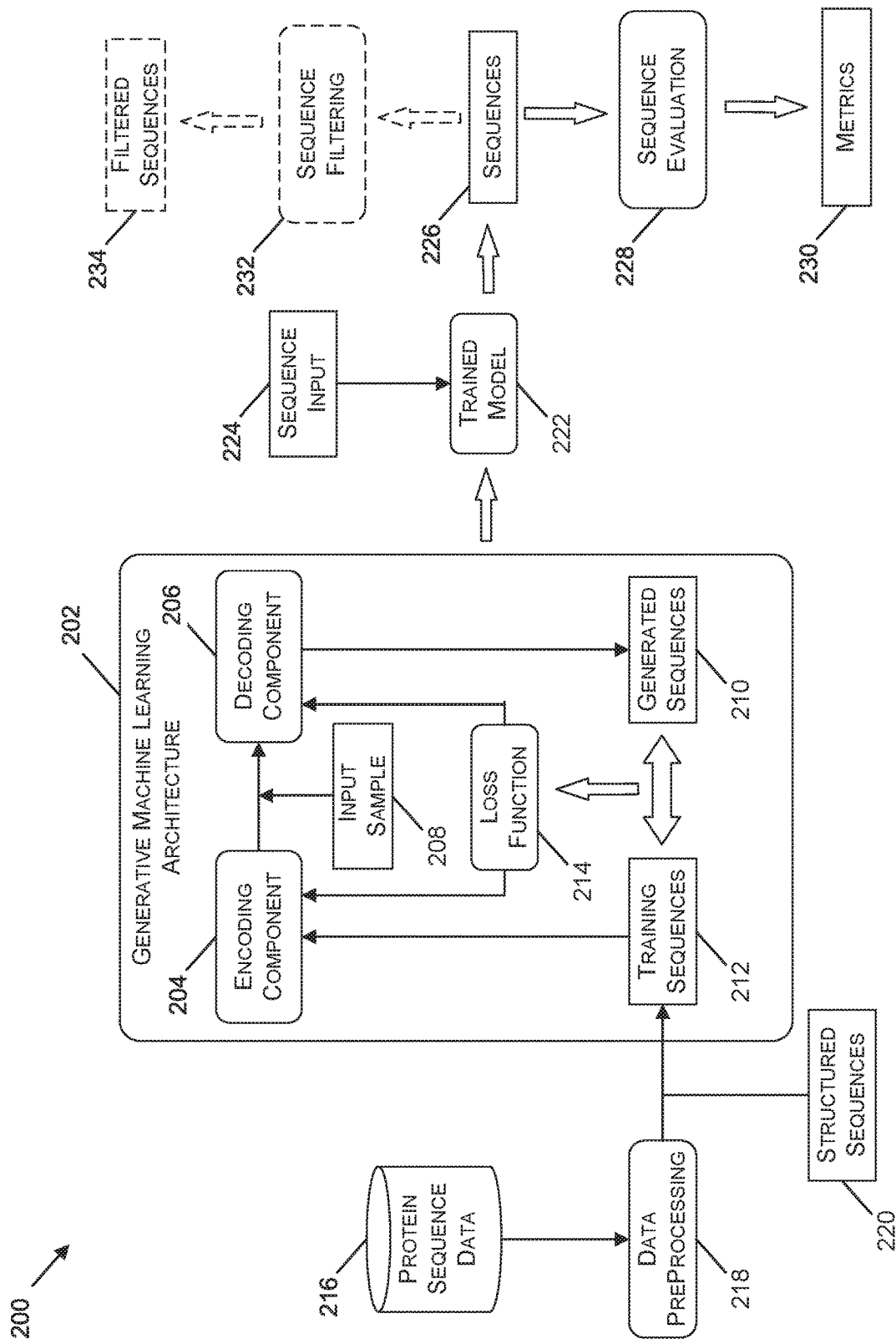
FIG. 2 is a diagram illustrating an example framework that includes an encoding component and a decoding component to generate protein sequences, in accordance with some implementations.

FIG. 2 is a diagram illustrating an example framework 200 that includes an encoding component and a decoding component to generate protein sequences, in accordance with some implementations. The framework 200 can include a generative machine learning architecture 202. The generative machine learning architecture 202 can correspond to an autoencoder implementation and include an encoding component 204 and a decoding component 206. The encoding component 204 can determine an encoding for input amino acid sequences and the encoding can be decoded by the decoding component 206 to produce one or more additional amino acid sequences. In various examples, an input sample 208 can be provided to the decoding component 206 and the decoding component 206 can use the input sample 208 and the encoding to produce generated sequences 210. The generated sequences 210 can be analyzed with respect to the training sequences 212 and a loss function 214 can be optimized based on differences between the generated sequences 210 and the training sequences 212. In one or more examples, output of the loss function 214 can be used to modify the sequences generated by the decoding component 206. In one or more examples, at least one of the encoding component 204 or the decoding component 206 may be modified to optimize the loss function 214. In various examples, at least one of the encoding component 204 or the decoding component 206 can be modified to minimize the loss function 214.

The generated sequences 210 can include amino acid sequences of proteins. In one or more examples, the generated sequences 210 can include amino acid sequences of antibodies. In various implementations, the decoding component 206 can implement a model that produces the generated sequences 210. In various examples, the model implemented by the decoding component 206 can include one or more functions.

The training sequences 212 may correspond to amino acid sequences obtained from the protein sequence data 214. The protein sequence data 214 can include sequences of proteins obtained from one or more data sources that store protein amino acid sequences. The protein sequence data 214 may include amino acid sequences of one or more proteins, such as fibronectin type III (FNIII) proteins, avimers, antibodies, VHH domains, kinases, zinc fingers, and the like.

The protein sequences included in the protein sequence data 214 can be subject to data preprocessing 216 before being provided to the generative machine learning architecture 202. In implementations, the protein sequence data 214 can be arranged according to a classification system by the data preprocessing 216 before being provided to the generative machine learning architecture 202. The data preprocessing 216 can include pairing amino acids included in the proteins of the protein sequence data 214 with numerical values that can represent structure-based positions within the proteins. The numerical values can include a sequence of numbers having a starting point and an ending point. In an illustrative example, a T can be paired with the number 43 indicating that a Threonine molecule is located at a structure-based position 43 of a specified protein domain type.

In various implementations, the classification system implemented by the data preprocessing 216 can designate a particular number of positions for certain regions of proteins. For example, the classification system can designate that portions of proteins have particular functions and/or characteristics can have a specified number of positions. In various situations, not all of the positions included in the classification system may be associated with an amino acid because the number of amino acids in a particular region of a protein may vary between proteins. To illustrate, the number of amino acids in a region of a protein can vary for different types of proteins. In additional examples, the structure of a protein can be reflected. In examples, positions of the classification system that are not associated with a particular amino acid can indicate various structural features of a protein, such as a turn or a loop. In an illustrative example, a classification system for antibodies can indicate that heavy chain regions. light chain regions, and hinge regions have a specified number of positions assigned to them and the amino acids of the antibodies can be assigned to the positions according to the classification system.

In implementations, the data included in the protein sequence data 216 used to train the generative machine learning architecture 202 can impact the amino acid sequences produced by the decoding component 206. For example, the characteristics, biophysical properties, manufacturing characteristics (e.g., titer, yield, etc.) and so forth, of the protein sequence data 216 can impact characteristics, biophysical properties, and/or manufacturing characteristics of the generated sequences 210 produced by the decoding component 206. To illustrate, in situations where antibodies are included in the protein sequence data 216 provided to the generative machine learning architecture 202, the amino acid sequences generated by the decoding component 206 can correspond to antibody amino acid sequences. In another example, in scenarios where T-cell receptors are included in the protein sequence data 216 provided to the generative machine learning architecture 202, the amino acid sequences generated by the decoding component 206 can correspond to T-cell receptor amino acid sequences. In an additional example, in situations where kinases are included in the protein sequence data 216 provided to the generative machine learning architecture 202, the amino acid sequences generated by the decoding component 206 can correspond to amino acid sequences of kinases. In implementations where amino acid sequences of a variety of different types of proteins are included in the protein sequence data 216 provided to the generative machine learning architecture 202, the decoding component 206 can generate amino acid sequences having characteristics of proteins generally and may not correspond to a particular type of protein.

The output produced by the data preprocessing 218 can include structured sequences 220. The structured sequences 220 can include a matrix indicating amino acids associated with various positions of a protein. In examples, the structured sequences 220 can include a matrix having columns corresponding to different amino acids and rows that correspond to structure-based positions of proteins. For each element in the matrix, a 0 can be used to indicate the absence of an amino acid at the corresponding position and a 1 can be used to indicate the presence of an amino acid at the corresponding position. In situations where a position represents a gap in an amino acid sequence, the row associated with the position can comprise zeroes for each column. The generated sequence(s) 210 can also be represented using a vector according to a same or similar number scheme as used for the structured sequences 220. In some illustrative examples, the structured sequences 220 and the generated sequence(s) 210 can be encoded using a method that may be referred to as a one-hot encoding method.

After the generative machine learning architecture 202 has undergone a training process, a trained model 222 can be generated that can produce sequences of proteins. The trained model 222 can include one or more components of the generative machine learning architecture 202 after a training process using the protein sequence data 216. In one or more implementations, the trained model 222 can include at least one of the encoding component 204 or the decoding component 206 that has been trained using the protein sequence data 216. In examples, the training process for the generative machine learning architecture 202 can be complete after the function(s) implemented by one or more components of the generative machine learning architecture 202 converge. The convergence of a function can be based on the movement of values of model parameters toward particular values as protein sequences are generated by the decoding component 206 and feedback is obtained in relation to the loss function 214 based on differences between the training sequences 212 and the generated sequences 210.

In various implementations, the training of the generative machine learning architecture 202 can be complete when the protein sequences generated by the decoding component 206 have particular characteristics. To illustrate, the amino acid sequences generated by the decoding component 206 can be analyzed by a software tool that can analyze amino acid sequences to determine at least one of biophysical properties of the amino acid sequences, structural features of the amino acid sequences, or adherence to amino acid sequences corresponding to one or more protein germlines. As used herein, germline, can correspond to amino acid sequences of proteins that are conserved when cells of the proteins replicate. An amino acid sequence can be conserved from a parent cell to a progeny cell when the amino acid sequence of the progeny cell has at least a threshold amount of identity with respect to the corresponding amino acid sequence in the parent cell. In an illustrative example, a portion of an amino acid sequence of a human antibody that is part of a kappa light chain that is conserved from a parent cell to a progeny cell can be a germline portion of the antibody.

Sequence input 224 can be provided to the trained model 222, and the trained model 222 can produce sequences 226. The sequence input 224 can correspond to random or pseudo-random series of numbers that can be used to produce the sequences 226 that can include amino acid sequences of proteins. The sequences 226 produced by the trained model 222 can be represented as a matrix structure that is the same as or similar to the matrix structure used to represent the structured sequences 220 and the generated sequence(s) 210. In various implementations, the matrices produced by the trained model 222 that comprise the sequences 226 can be decoded to produce a string of amino acids that correspond to the sequence of a protein. At operation 228, the sequences 226 can be evaluated to determine whether the sequences 226 have a specified set of characteristics. The sequence evaluation performed at operation 228 can produce metrics 230 that indicate characteristics of the sequences 226. Additionally, the metrics 230 can indicate an amount of correspondence between the characteristics of the sequences 226 and a specified set of characteristics. In some examples, the metrics 230 can indicate a number of positions of an amino acid sequence 226 that vary from an amino acid sequence of a protein produced from a germline gene.

The sequences 226 produced by the model 222 can correspond to various types of proteins. For examples, the sequences 226 can correspond to proteins that function as T-cell receptors. In additional examples, the sequences 226 can correspond to proteins that function as catalysts to cause biochemical reactions within an organism to take place. The sequences 226 can also correspond to one or more types of antibodies. To illustrate, the sequences 226 can correspond to one or more antibody subtypes, such as immunoglobin A (IgA), immunoglobin D (IgD), immunoglobin E (IgE), immunoglobin G (IgG), or immunoglobin M (IgM). Further, the sequences 226 can correspond to additional proteins that bind antigens. In examples, the sequences 226 can correspond to affibodies, affilins, affimers, affitins, alphabodies, anticalins, avimers, monobodies, designed ankyrin repeat proteins (DARPins), nanoCLAMP (clostridal antibody mimetic proteins), antibody fragments, or combinations thereof. In still other examples, the sequences 226 can correspond to amino acid sequences that participate in protein-to-protein interactions, such as proteins that have regions that bind to antigens or regions that bind to other molecules.

In some implementations, the sequences 226 can be subject to sequence filtering at operation 232 to produce one or more filtered sequences 234. The sequence filtering 232 can parse the sequences 226 for one or more of the sequences 226 that correspond to one or more characteristics. For example, the sequence filtering at operation 232 can analyze the sequences 226 to identify sequences 226 that have specified amino acids at particular positions. The sequence filtering 232 can also identify one or more of the sequences 226 that have one or more particular strings of amino acids. In various implementations, the sequence filtering at operation 232 can identify one or more of the sequences 226 that have a set of biophysical properties based on similarities between at least one of the sequences 226 and amino acid sequences of proteins having the set of biophysical properties.

Figure 3:
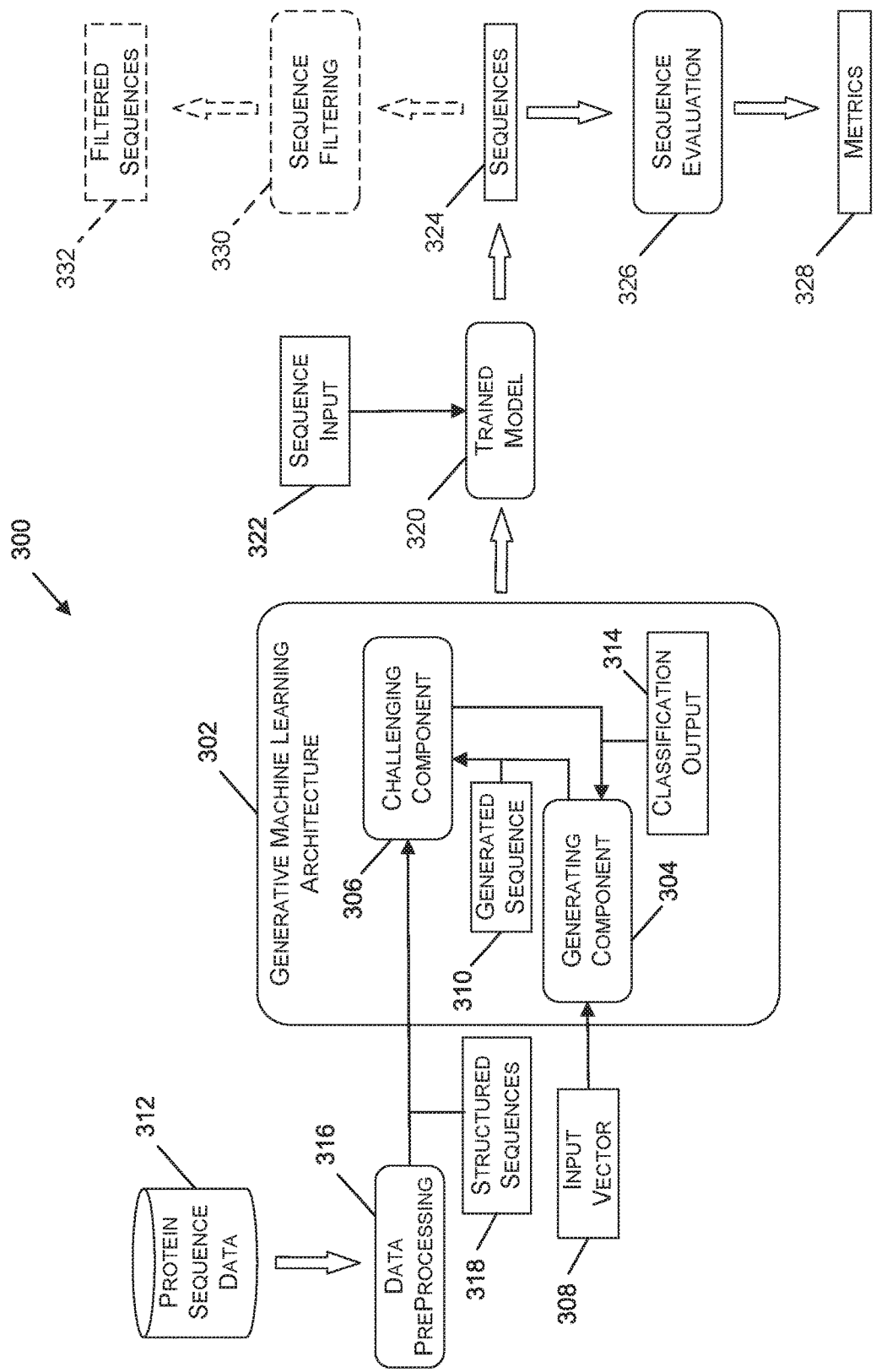
FIG. 3 is a diagram illustrating an example framework including a generating component and a challenging component to generate protein sequences, in accordance with some implementations.

FIG. 3 is a diagram illustrating an example framework 300 including a generating component and a challenging component to generate protein sequences, in accordance with some implementations. The framework 300 can include a generative machine learning architecture 302. The generative machine learning architecture 302 can include a generating component 304 and a challenging component 306. The generating component 304 can implement a model to generate amino acid sequences based on input provided to the generating component 304. In various implementations, the model implemented by the generating component 304 can include one or more functions. The challenging component 306 can generate output indicating whether the amino acid sequences produced by the generating component 304 satisfy various characteristics. The output produced by the challenging component 306 can be provided to the generating component 304 and the model implemented by the generating component 304 can be modified based on the feedback provided by the challenging component 306. In various implementations, the challenging component 306 can compare the amino acid sequences generated by the generating component 304 with amino acid sequences of proteins and generate an output indicating an amount of correspondence between the amino acid sequences produced by the generating component 304 and the amino acid sequences of proteins provided to the challenging component 306.

In various implementations, the machine learning architecture 302 can implement one or more neural network technologies. For example, the machine learning architecture 302 can implement one or more recurrent neural networks. Additionally, the machine learning architecture 302 can implement one or more convolutional neural networks. In certain implementations, the machine learning architecture 302 can implement a combination of recurrent neural networks and convolutional neural networks. In examples, the machine learning architecture 302 can include a generative adversarial network (GAN). In these situations, the generating component 304 can include a generator and the challenging component 306 can include a discriminator. In additional implementations, the machine learning architecture 302 can include a Wasserstein generative adversarial network (wGAN). In these scenarios, the generating component 304 can include a generator and the classifying component 306 can include a critic.

In the illustrative example of FIG. 3, an input vector 308 can be provided to the generating component 304 and the generating component 304 can produce one or more generated sequences 310 from the input vector 308 using a model. In particular implementations, the input vector 308 can include noise that is generated by a random or pseudo-random number generator. The generated sequence(s) 310 can be compared by the challenging component 306 against sequences of proteins included in the protein sequence data 312 that have been encoded according to a particular schema. The protein sequence data 312 can include sequences of proteins obtained from one or more data sources that store protein sequences.

Based on similarities and differences between the generated sequence(s) 310 and the sequences obtained from the protein sequence data 312, the classifying component 306 can generate a classification output 314 that indicates an amount of similarity or an amount of difference between the generated sequence 310 and sequences included in the protein sequence data 312. In examples, the challenging component 306 can label the generated sequence(s) 310 as zero and the structured sequences obtained from the protein sequence data 312 as one. In these situations, the classification output 314 can correspond to a number from 0 and 1. In additional examples, the challenging component 306 can implement a distance function that produces an output that indicates an amount of distance between the generated sequence(s) 310 and the proteins included in the protein sequence data 312. In these scenarios, the challenging component 306 can label the generated sequence(s) 310 as −1 and the encoded amino acid sequences obtained from the protein sequence data 312 as 1. In implementations where the challenging component 306 implements a distance function, the classification output 314 can be a number from −∞ to ∞. In some examples, the amino acid sequence obtained from the protein sequence data 312 can be referred to as ground truth data.

The protein sequences included in the protein sequence data 312 can be subject to data preprocessing 316 before being provided to the challenging component 306. In implementations, the protein sequence data 312 can be arranged according to a classification system before being provided to the challenging component 306. The data preprocessing 316 can include pairing amino acids included in the proteins of the protein sequence data 312 with numerical values that can represent structure-based positions within the proteins. The numerical values can include a sequence of numbers having a starting point and an ending point. In an illustrative example, a T can be paired with the number 43 indicating that a Threonine molecule is located at a structure-based position 43 of a specified protein domain type. In illustrative examples, structure-based numbering can be applied to any general protein type, such as fibronectin type III (FNIII) proteins, avimers, antibodies, VHH domains, kinases, zinc fingers, and the like.

In various implementations, the classification system implemented by the data preprocessing 316 can designate a particular number of positions for certain regions of proteins. For example, the classification system can designate that portions of proteins have particular functions and/or characteristics can have a specified number of positions. In various situations, not all of the positions included in the classification system may be associated with an amino acid because the number of amino acids in a particular region of a protein may vary between proteins. To illustrate, the number of amino acids in a region of a protein can vary for different types of proteins. In additional examples, the structure of a protein can be reflected. In examples, positions of the classification system that are not associated with a particular amino acid can indicate various structural features of a protein, such as a turn or a loop. In an illustrative example, a classification system for antibodies can indicate that heavy chain regions, light chain regions, and hinge regions have a specified number of positions assigned to them and the amino acids of the antibodies can be assigned to the positions according to the classification system.

In implementations, the data used to train the machine learning architecture 302 can impact the amino acid sequences produced by the generating component 304. For example, in situations where antibodies are included in the protein sequence data 312 provided to the challenging component 306, the amino acid sequences generated by the generating component 304 can correspond to antibody amino acid sequences. In another example, in scenarios where T-cell receptors are included in the protein sequence data 312 provided to the challenging component 306 the amino acid sequences generated by the generating component 304 can correspond to T-cell receptor amino acid sequences. In an additional example, in situations where kinases are included in the protein sequence data 312 provided to the challenging component 306, the amino acid sequences generated by the generating component 304 can correspond to amino acid sequences of kinases. In implementations where amino acid sequences of a variety of different types of proteins are included in the protein sequence data 312 provided to the classifying component 306, the generating component 304 can generate amino acid sequences having characteristics of proteins generally and may not correspond to a particular type of protein. Further, in various examples, the amino acid sequences produced by the generating component 304 can correspond to the types of proportions of amino acid sequences included in the protein sequence data 312 provided to the challenging component 306.

The output produced by the data preprocessing 316 can include structured sequences 318. The structured sequences 318 can include a matrix indicating amino acids associated with various positions of a protein. In examples, the structured sequences 318 can include a matrix having columns corresponding to different amino acids and rows that correspond to structure-based positions of proteins. For each element in the matrix, a 0 can be used to indicate the absence of an amino acid at the corresponding position and a 1 can be used to indicate the presence of an amino acid at the corresponding position. In situations where a position represents a gap in an amino acid sequence, the row associated with the position can comprise zeroes for each column. The generated sequence(s) 310 can also be represented using a vector according to a same or similar number scheme as used for the structured sequences 318. In some illustrative examples, the structured sequences 318 and the generated sequence(s) 310 can be encoded using a method that may be referred to as a one-hot encoding method.

After the machine learning architecture 302 has undergone a training process, a trained model 320 can be generated that can produce sequences of proteins. The trained model 320 can include the generating component 304 after a training process using the protein sequence data 312. In examples, the training process for the machine learning architecture 302 can be complete after the function(s) implemented by the generating component 304 and the function(s) implemented by the challenging component 306 converge. The convergence of a function can be based on the movement of values of model parameters toward particular values as protein sequences are generated by the generating component 304 and feedback is obtained from the challenging component 306. In various implementations, the training of the machine learning architecture 302 can be complete when the protein sequences generated by the generating component 304 have particular characteristics. To illustrate, the amino acid sequences generated by the generating component 304 can be analyzed by a software tool that can analyze amino acid sequences to determine at least one of biophysical properties of the amino acid sequences, structural features of the amino acid sequences, or adherence to amino acid sequences corresponding to one or more protein germlines. As used herein, germline, as used herein, can correspond to amino acid sequences of proteins that are conserved when cells of the proteins replicate. An amino acid sequence can be conserved from a parent cell to a progeny cell when the amino acid sequence of the progeny cell has at least a threshold amount of identity with respect to the corresponding amino acid sequence in the parent cell. In an illustrative example, a portion of an amino acid sequence of a human antibody that is part of a kappa light chain that is conserved from a parent cell to a progeny cell can be a germline portion of the antibody.

Sequence input 322 can be provided to the trained model 320, and the trained model 320 can produce sequences 324.

The sequence input 322 can correspond to random or pseudo-random series of numbers that can be used to produce the sequences 324 that can include amino acid sequences of proteins. The sequences 324 produced by the trained model 320 can be represented as a matrix structure that is the same as or similar to the matrix structure used to represent the structured sequences 318 and the generated sequence(s) 310. In various implementations, the matrices produced by the trained model 320 that comprise the sequences 324 can be decoded to produce a string of amino acids that correspond to the sequence of a protein. At 326, the sequences 324 can be evaluated to determine whether the sequences 324 have a specified set of characteristics. The sequence evaluation 326 can produce metrics 328 that indicate characteristics of the sequences 324. Additionally, the metrics 328 can indicate an amount of correspondence between the characteristics of the sequences 324 and a specified set of characteristics. In some examples, the metrics 328 can indicate a number of positions of an amino acid sequence 324 that vary from an amino acid sequence of a protein produced from a germline gene.

The sequences 324 produced by the model 320 can correspond to various types of proteins. For examples, the sequences 324 can correspond to proteins that function as T-cell receptors. In additional examples, the sequences 324 can correspond to proteins that function as catalysts to cause biochemical reactions within an organism to take place. The sequences 324 can also correspond to one or more types of antibodies. To illustrate, the sequences 324 can correspond to one or more antibody subtypes, such as immunoglobin A (IgA), immunoglobin D (IgD), immunoglobin E (IgE), immunoglobin G (IgG), or immunoglobin M (IgM). Further, the sequences 324 can correspond to additional proteins that bind antigens. In examples, the sequences 324 can correspond to affibodies, affilins, affimers, affitins, alphabodies, anticalins, avimers, monobodies, designed ankyrin repeat proteins (DARPins), nanoCLAMP (clostridal antibody mimetic proteins), antibody fragments, or combinations thereof. In still other examples, the sequences 324 can correspond to amino acid sequences that participate in protein-to-protein interactions, such as proteins that have regions that bind to antigens or regions that bind to other molecules.

In some implementations, the sequences 324 can be subject to sequence filtering 330 to produce one or more filtered sequences 332. The sequence filtering 330 can parse the sequences 324 for one or more of the sequences 324 that correspond to one or more characteristics. For example, the sequence filtering 330 can analyze the sequences 324 to identify sequences 324 that have specified amino acids at particular positions. The sequence filtering 330 can also identify one or more of the sequences 324 that have one or more particular strings of amino acids. In various implementations, the sequence filtering 330 can identify one or more of the sequences 324 that have a set of biophysical properties based on similarities between at least one of the sequences 324 and amino acid sequences of proteins having the set of biophysical properties.

Figure 4:
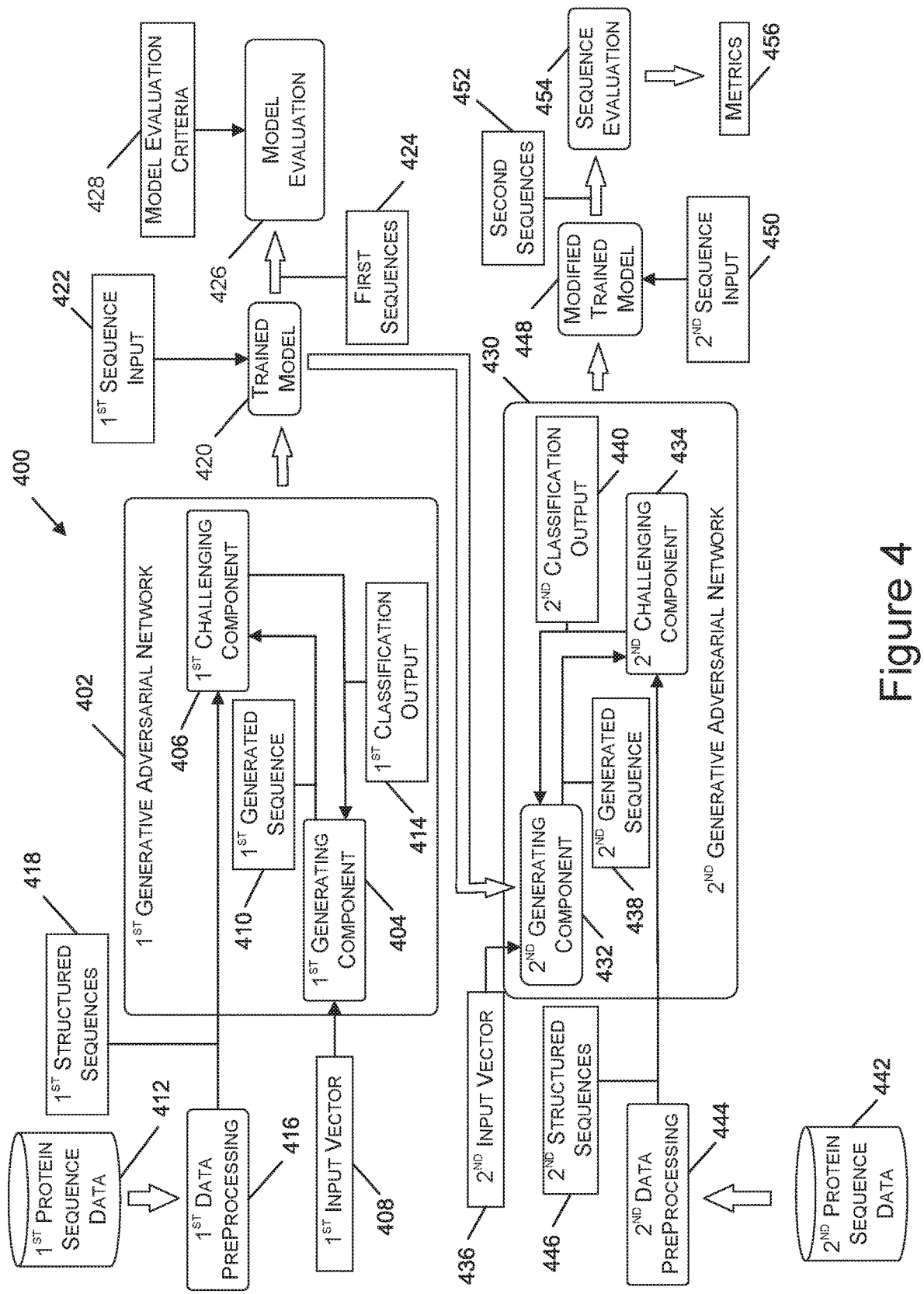
FIG. 4 is a diagram illustrating an example framework to generate protein sequences using a first set of training data that has a first set of characteristics and a second set of training data that has a second, different set of characteristics, in accordance with some implementations.

FIG. 4 is a diagram illustrating an example framework 400 to generate protein sequences using a first set of training data having a first set of characteristics and a second set of training data that has a second set of characteristics that is different from the first set of characteristics, in accordance with some implementations. The framework 400 can include a first generative adversarial network 402. The first generative adversarial network 402 can include a first generating component 404 and a first challenging component 406. In various implementations, the first challenging component 406 can be a discriminator. In additional situations, such as when the first generative adversarial network 402 is a Wasserstein GAN, the first challenging component 406 can include a critic. The first generating component 204 can implement a model to generate amino acid sequences based on input provided to the first generating component 404. The first challenging component 406 can generate output indicating whether the amino acid sequences produced by the generating component 404 satisfy various characteristics. The output produced by the first challenging component 406 can be provided to the generating component 404 and a model implemented by the first generating component 404 can be modified based on the feedback provided by the first challenging component 406. In various implementations, the first challenging component 406 can compare the amino acid sequences produced by the first generating component 404 with amino acid sequences of proteins and generate an output indicating an amount of correspondence between the amino acid sequences produced by the first generating component 404 and the amino acid sequences of proteins provided to the first challenging component 406.

A first input vector 408 can be provided to the first generating component 404 and the first generating component 404 can produce one or more first generated sequences 410 using the first input vector 408 using a model. In particular implementations, the first input vector 408 can be produced using a random or pseudo-random number generator. In illustrative examples, the first input vector 408 can include a noise signal that includes a series of numbers.

The first generated sequence(s) 410 can be compared by the first challenging component 406 against sequences of proteins included in the protein sequence data 412. The first protein sequence data 412 can include sequences of proteins obtained from one or more data sources that store protein sequences. Based on similarities and differences between the first generated sequence(s) 410 and the sequences obtained from the protein sequence data 412, the first challenging component 406 can generate a first classification output 414 that indicates an amount of similarity or an amount of difference between the first generated sequence(s) 410 and sequences included in the first protein sequence data 412. The first challenging component 406 can label the first generated sequence(s) 410 with a zero and structured sequences derived from the first protein sequence data 412 with a one. In these situations, the first classification output 414 can include a number from 0 and 1 In additional examples when the first generative adversarial network 402 is a Wasserstein GAN, the first challenging component 406 can implement a distance function that produces an output that indicates an amount of distance between the first generated sequence(s) 410 and the proteins included in the first protein sequence data 412. In these scenarios, the first challenging component 406 can label the first generated sequence(s) 410 as −1 and the encoded amino acid sequences obtained from the first protein sequence data 412 as 1. In implementations where the first challenging component 406 implements a distance function, the first classification output 414 can be a number from $-\infty$ to $\infty$. In some examples, the amino acid sequences obtained from the first protein sequence data 412 can be referred to as ground truth data.

The protein sequences included in the protein sequence data 412 can be subject to first data preprocessing 416 before being provided to the first challenging component 406. In implementations, the protein sequence data 412 can be arranged according to a classification system before being provided to the first challenging component 406. The first data preprocessing 416 can include pairing amino acids included in the proteins of the first protein sequence data 412 with numerical values that can represent positions within the proteins. The numerical values can include a sequence of numbers having a starting point and an endpoint. The first data preprocessing 416 can generate first structured sequences 418 that are provided to the first challenging component 406. The first structured sequences 418 can include a matrix indicating amino acids associated with various positions of a protein. In examples, the first structured sequences 418 can include a matrix having columns corresponding to different amino acids and rows that correspond to structure-based positions of proteins. For each element in the matrix, a 0 can be used to indicate the absence of an amino acid at the corresponding position and a 1 can be used to indicate the presence of an amino acid at the corresponding position. In situations where a position represents a gap in an amino acid sequence, the row associated with the position can comprise zeroes for each column. The first generated sequence(s) 410 can also be represented using a vector according to a same or similar number scheme as used for the first structured sequences 418. In some illustrative examples, the first structured sequences 418 and the first generated sequence(s) 410 can be encoded using a method that may be referred to as a one-hot encoding method.

After the first generative adversarial network 402 has undergone a training process, a trained model 420 can be generated that can produce sequences of proteins. In examples, the training process for the first generative adversarial network 402 can be complete after the function(s) implemented by the first generating component 404 converge. In various implementations, the training of the first generative adversarial network 402 can be complete when the protein sequences generated by the first generating component 404 have particular characteristics. To illustrate, the amino acid sequences generated using the trained model 420 can be analyzed by a software tool that can analyze amino acid sequences to determine at least one of biophysical properties of the amino acid sequences, structural features of the amino acid sequences, or adherence to amino acid sequences corresponding to one or more amino acid sequences derived from a germline gene of a protein.

First sequence input 422 can be provided to the trained model 420, and the trained model 420 can produce first sequences 424. The first sequence input 422 can correspond to random or pseudo-random series of numbers that can be used to produce the first sequences 424 that correspond to amino acids and the first sequences 424 can include amino acid sequences of proteins. The first sequences 424 produced by the trained model 420 can be represented as a matrix structure that is the same as or similar to the matrix structure used to represent the first structured sequences 418 and the first generated sequence(s) 410. In various implementations, the matrices produced by the trained model 420 that comprise the first sequences 424 can be decoded to produce a string of amino acids that correspond to the sequence of a protein. At operation 426, a model evaluation 426 can be performed with respect to the trained model 420 based on the first sequences 424 produced by the trained model 420 and based on model evaluation criteria 428. In particular implementations, the model evaluation criteria 428 can be the same or similar to the criteria utilized to determine whether the training of the first generative adversarial network 402 has been completed. In additional implementations, the model evaluation criteria 428 can be different from the criteria utilized to determine whether the training of the first generative adversarial network 402 has been completed. In illustrative examples, the model evaluation criteria 428 can correspond to characteristics of the sequences produced using the trained model 420. In these scenarios, the model evaluation 426 can include comparing the first sequences 424 to sequence characteristics included in the model evaluation criteria 428. To illustrate, the model evaluation 426 can include determining whether the first sequences 424 include specified amino acid sequences at particular positions. In additional implementations, the model evaluation 426 can include determining whether the first sequences 424 correspond to amino acids having specified biophysical and/or having specified tertiary structures. Further, the model evaluation 426 can include determining whether there is convergence with respect to the model 420. In some examples, the model evaluation 426 can include review by a human expert of the first sequences 424 based on the model evaluation criteria 428.

In illustrative examples, the protein sequence data 412 can include amino acid sequences of antibodies. In these scenarios, the amino acid sequences provided to the first challenging component 406 can correspond to antibodies having a number of different characteristics. For example, the first challenging component 406 can be provided amino acid sequences from antibodies of different isotypes, IgA, IgD, IgE, IgD, and/or IgM. In additional examples, the amino acid sequences provided to the first challenging component 406 can be related to proteins derived from genes of different germlines. In further examples, the amino acid sequences of antibodies provided to the first challenging component 406 can have various lengths and/or sequences for the variable regions of the light chains and/or the variable regions for the heavy chains. In still other examples, the amino acid sequences provided to the first challenging component 406 can be at least portions of light chain regions of antibodies, at least portions of heavy chain regions of antibodies, or combinations thereof. In still additional examples, the amino acid sequences provided to the first challenging component 406 can have a number of different biophysical properties of antibodies, such as amino acid sequences corresponding to hydrophobic regions, amino acid sequences corresponding to negatively charged regions, amino acid sequences corresponding to positively charged regions, or combinations thereof. Further, the amino acid sequences provided to the first challenging component 406 can correspond to antibodies and/or antibody regions having various solubility characteristics and/or various thermal degradation characteristics.

As a result of training the first generative adversarial network 402 on a number of amino acid sequences of proteins having a first set of characteristics. In examples, the first generative adversarial network 402 can be trained using amino acid sequences having a relatively general property. In some implementations, the first generative adversarial network 402 can be trained using a dataset on the order of thousands or more amino acid sequences. In a particular illustrative example, the first generative adversarial network 402 can be trained to generate amino acid sequences that exhibit characteristics that correspond to antibodies, in general. In these implementations, the model evaluation 426 can determine whether the first sequences 424 correspond to general characteristics of antibodies. For example, the model evaluation criteria 428 can identify the structure of antibodies in the first sequences 424. To illustrate, the model evaluation 426 can determine whether the first sequences 424 have variable regions and constant regions. The model evaluation 426 can also determine whether the first sequences 424 have a specified number or range of numbers of amino acids that correspond to a number of amino acids in a heavy chain region and/or a specified number or range of numbers of amino acids in a light chain region. Additionally, the model evaluation 426 can determine whether the first sequences 424 have hinge regions linking constant regions of heavy chains. Further, the model evaluation 426 can determine whether the first sequences 424 have amino acids that can form disulfide bonds at specified positions.

After the model evaluation 426 determines that the trained model 420 satisfies one or more of the model evaluation criteria, the trained model 420 can undergo further training on another dataset. In implementations, the trained model 420 can be represented as being included in a second generative adversarial network 430 that comprises a second generating component 432 and a second challenging component 434. In particular examples, the trained model 420 can be represented by the second generating component 432. In various implementations, the second generating component 432 can include the trained model 420 after one or more modifications have been made to the trained model 420. For example, modifications can be made to the trained model 420 in relation to the architecture of the trained model 420, such as the addition of one or more hidden layers or changes to one or more network filters. The second generating component 432 can obtain a second input vector 436 to produce second generated sequence(s) 438. In various implementations, the second challenging component 434 can be a discriminator. In additional situations, such as when the second generative adversarial network 430 is a Wasserstein GAN, the second challenging component 434 can include a critic. The second input vector 436 can include a random or pseudo-random sequence of numbers.

The second challenging component 434 can generate second classification output 440 indicating whether the amino acid sequences produced by the second generating component 432 satisfy various characteristics. In illustrative examples, based on similarities and differences between the second generated sequence(s) 438 and the sequences provided to the second challenging component 434, such as amino acid sequences included in the protein sequence data 412, the second challenging component 434 can generate the second classification output 440 that indicates an amount of similarity or an amount of difference between the second generated sequence(s) 238 and comparison sequences provided to the second challenging component 434. The comparison sequences provided to the second challenging component 434 can correspond to amino acid sequences included in second protein sequence data 442. The second protein sequence data 442 can include amino acid sequences that can be at least partially different from the amino acid sequences included in the first protein sequence data 412. In some illustrative examples, the second protein sequence data 442 can include a subset of the first protein sequence data 412. In implementations, protein sequence filtering can be applied to the first protein sequence data 412 by analyzing the first protein data 412 according to one or more criteria. For example, the second protein sequence data 442 can correspond to particular types of proteins and/or amino acid sequences that include regions having specified amino acids at particular positions. Additionally, the second protein sequence data 442 can correspond to amino acid sequences of proteins that have specified biophysical properties. In various implementations, the second protein sequence data 442 can correspond to amino acid sequences of proteins that have specified structural properties. Examples of specified structural properties can include surface charge of one or more regions and post translational modifications.

The second challenging component 434 can label the second generated sequence(s) 438 with a zero and structured sequences derived from the protein sequence data 442 with a one. In these situations, the second classification output 440 can include a number from 0 and 1 In additional examples when the second generative adversarial network 430 is a Wasserstein GAN, the second challenging component 434 can implement a distance function that produces an output that indicates an amount of distance between the second generated sequence(s) 238 and the proteins included in the second protein sequence data 442. In implementations where the second challenging component 434 implements a distance function, the second classification output 440 can be a number from $-\infty$ to $\infty$. In some examples, the amino acid sequences obtained from the second protein sequence data 442 can be referred to as ground truth data.

After the filtered sequences 444 have been produced by the protein sequence filtering 442, the filtered sequences can be subject to second data preprocessing 446 before being provided to the second challenging component 434. In implementations, the filtered sequences 444 can be arranged according to a classification system before being provided to the second challenging component 434. The second data preprocessing 444 can include pairing amino acids included in the proteins of the second protein sequence data 442 with numerical values that can represent positions within the proteins. The numerical values can include a sequence of numbers having a starting point and an endpoint. The second data preprocessing 444 can generate second structured sequences 446 that are provided to the second challenging component 434. The second structured sequences 446 can include a matrix indicating amino acids associated with various positions of a protein. In examples, the second structured sequences 446 can include a matrix having columns corresponding to different amino acids and rows that correspond to structure-based positions of proteins. For each element in the matrix, a 0 can be used to indicate the absence of an amino acid at the corresponding position and a 1 can be used to indicate the presence of an amino acid at the corresponding position. The matrix can also include an additional column that represents a gap in an amino acid sequence where there is no amino acid at a particular position of the amino acid sequence. Thus, in situations where a position represents a gap in an amino acid sequence, a 1 can be placed in the gap column with respect to the row associated with the position where an amino acid is absent. The second generated sequence(s) 438 can also be represented using a vector according to a same or similar number scheme as used for the second structured sequences 446. In some illustrative examples, the second structured sequences 446 and the second generated sequence(s) 438 can be encoded using a method that may be referred to as a one-hot encoding method.

After the second generative adversarial network 430 has undergone a training process, a modified trained model 448 can be generated that can produce sequences of proteins. The modified trained model 448 can represent the trained model 420 after being trained using the second protein sequence data 442. In examples, the training process for the second generative adversarial network 430 can be complete after the function(s) implemented by the second generating component 432 and the second challenging component 434 converge. The convergence of a function can be based on the movement of values of model parameters toward particular values as protein sequences are generated by the second generating component 432 and feedback is obtained from the second challenging component 434. In various implementations, the training of the second generative adversarial network 430 can be complete when the protein sequences generated by the second generating component 432 have particular characteristics.

Second sequence input 450 can be provided to the modified trained model 448, and the modified trained model 448 can produce second sequences 452. The second sequence input 450 can include a random or pseudo-random series of numbers and the second sequences 452 can include amino acid sequences that can be sequences of proteins. At operation 454, the second sequences 452 can be evaluated to determine whether the second sequences 452 have a specified set of characteristics. The sequence evaluation 454 can produce metrics 456 that indicate characteristics of the second sequences 452, such as biophysical properties of a protein or a region of a protein and/or the presence or absence of amino acids located at specified positions. Additionally, the metrics 456 can indicate an amount of correspondence between the characteristics of the second sequences 452 and a specified set of characteristics. In some examples, the metrics 456 can indicate a number of positions of a second sequence 452 that vary from a sequence produced by a germline gene of a protein. Further, the sequence evaluation 454 can determine the presence or absence of structural features of proteins that correspond to the second sequences 452.

By continuing to train the trained model 420 as part of the second generative adversarial network 430, the modified trained model 448 can be produced that generates amino acid sequences that are more specifically tailored than those produced by the trained model 420. For example, the second generative adversarial network 430 can be training using filtered amino acid sequences that correspond to proteins have particular structure features and/or specified biophysical properties. Thus, once the trained model 420 has been produced by the first generative adversarial network 402 to generate amino acid sequences that correspond to proteins, the modified trained model 448 can be produced as part of the second generative adversarial network 430 to produce amino acid sequences of more specific proteins according to the second protein sequence data 442 provided to the second generative adversarial network 430.

Additionally, in many situations where it is desired to produce amino acid sequences of proteins having specific characteristics, the number of sequences available to train a generative adversarial network is limited. In these situations, the accuracy, efficiency, and/or effectiveness of the generative adversarial network to produce amino acid sequences of proteins having the specified characteristics may be unsatisfactory. Thus, without a sufficient number of amino acid sequences available to train a generative adversarial network, the amino acid sequences produced by the generative adversarial network may not have the desired characteristics. By implementing the techniques and systems described with respect to FIG. 4, a first generative adversarial network 402 can perform part of the process of determining amino acid sequences that correspond to proteins or that correspond to a broader class of proteins using a first dataset and the second generative adversarial network 430 can perform an additional part of the process where amino acid sequences of proteins having more specific characteristics are accurately and efficiently generated using a second, different dataset.

In illustrative examples, the modified model 448 can produce amino acid sequences that correspond to antibodies or portions of antibodies having particular characteristics. For example, after the first generative adversarial network 402 has produced the trained model 420 to generate amino acid sequences that have characteristics of antibodies, generally, the second generative adversarial network 430 can produce the modified trained model 448 to produce antibodies or portions of antibodies that have at least one of specified biophysical characteristics, amino acid sequences that correspond to antibodies or antibody regions related to a germline gene, or amino acid sequences of antibodies that have specified structural features, such as particular structure properties at specified locations. In particular illustrative examples, the trained model 420 can be used to generate amino acid sequences that correspond to IgG antibodies and the modified trained model 448 can be used to generate amino acid sequences that correspond to IgG antibodies including light chains with variable regions having particular amino acids at specified positions. In additional illustrative examples, the trained model 420 can be used to generate amino acid sequences of heavy chains of antibodies and the modified trained model 448 can be used to generate amino acid sequences of heavy chains of antibodies that can form disulfide bonds at specified positions.

While the illustrative example of FIG. 4 illustrates the training of a model using multiple training sets in a framework that includes two generative adversarial networks. in additional implementations, the training of a model using multiple training datasets can also be represented using a single generative adversarial network. Further, while the illustrative example of FIG. 4 illustrates the training of a model using generative adversarial networks with two training datasets, in various implementations, more than two datasets can be used to train models using generative adversarial networks according to implementations described herein.

Figure 5:
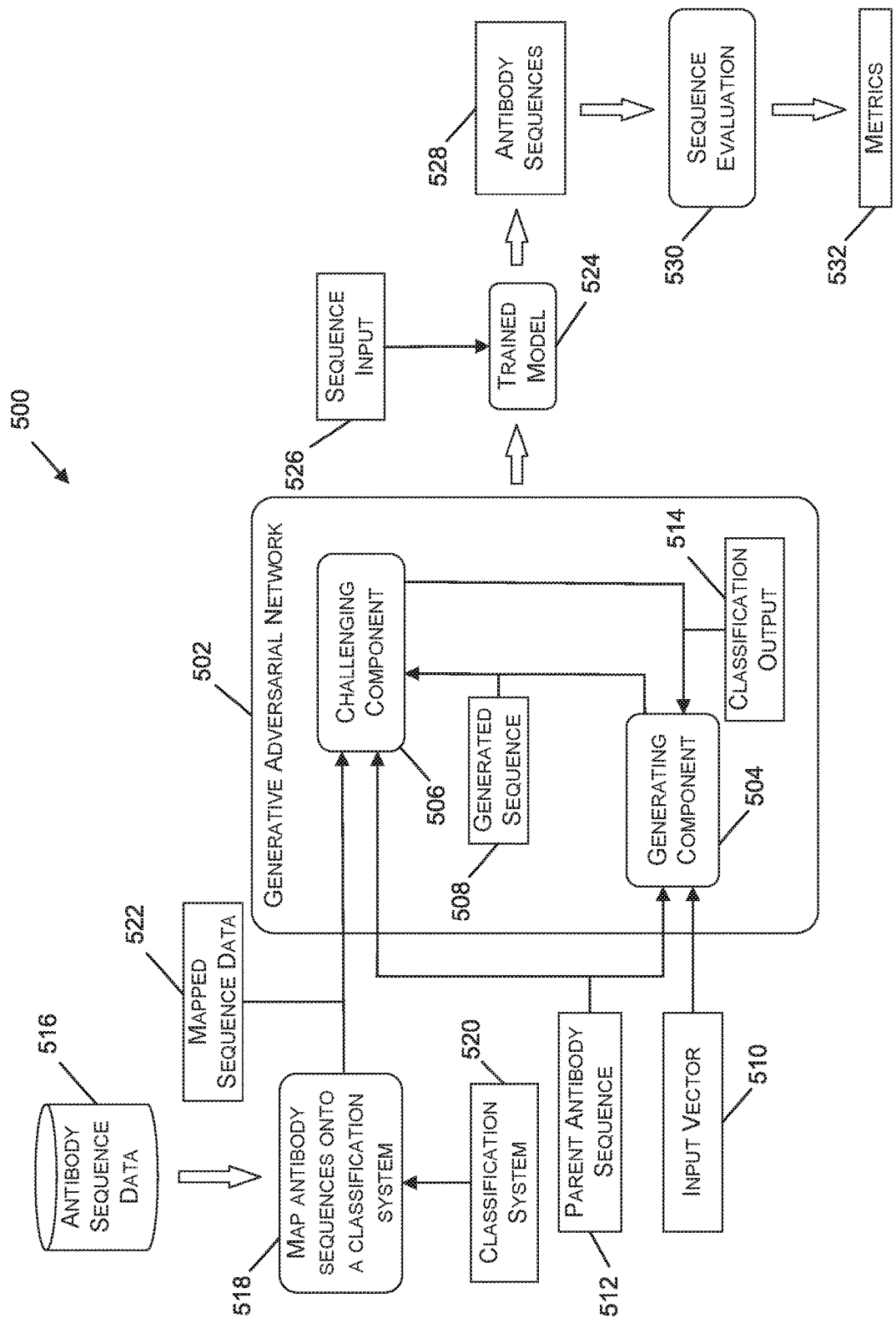
FIG. 5 is a diagram illustrating an example framework to generate antibody sequences that are variants of a parent antibody, in accordance with some implementations.

FIG. 5 is a diagram illustrating an example framework 500 to generate antibody sequences that are variants of a parent antibody, in accordance with some implementations. The framework 500 can include a generative adversarial network 502 that can include a generating component 504 and a challenging component 506. The generating component 504 can implement a model to generate amino acid sequences based on input provided to the generating component 504. In various implementations, the model implemented by the generating component 504 can include one or more functions. In implementations, the generating component 504 can utilize a model to produce generated sequence(s) 508. In various examples, the generating component 504 can implement a model to generate amino acid sequences based on an input vector 510 provided to the generating component 504 and a parent antibody sequence 512. The training input 510 can include a random or pseudo-random sequence of numbers of a specified length. The parent antibody sequence 512 can be provided to the generating component 504 as a matrix having columns corresponding to different amino acids and rows that correspond to structure-based positions of proteins. For each element in the matrix, a 0 can be used to indicate the absence of an amino acid at the corresponding position and a 1 can be used to indicate the presence of an amino acid at the corresponding position. The matrix can also include an additional column that represents a gap in an amino acid sequence where there is no amino acid at a particular position of the amino acid sequence. Thus, in situations where a position represents a gap in an amino acid sequence, a 1 can be placed in the gap column with respect to the row associated with the position where an amino acid is absent.

The parent antibody sequence 512 can include a base molecule that the generative adversarial network 502 can utilize to train a model to produce variant antibody sequences that correspond to the parent antibody sequence 512.

The challenging component 506 can generate output indicating whether the amino acid sequences produced by the generating component 504 satisfy various characteristics. In various implementations, the challenging component 506 can be a discriminator. In additional situations, such as when the generative adversarial network 502 is a Wasserstein GAN, the challenging component 506 can include a critic. In examples, the challenging component 506 can generate classification output 514 indicating whether the amino acid sequences produced by the generating component 504 satisfy various characteristics. In illustrative examples, based on similarities and differences between the generated sequence(s) 508 and additional sequences provided to the challenging component 506, such as amino acid sequences included in antibody sequence data 516, the challenging component 506 can generate the classification output 514 to indicate an amount of similarity or an amount of difference between the generated sequence(s) 508 and sequences provided to the challenging component 506 included in the antibody sequence data 516. The antibody sequence data 516 can include amino acid sequences of antibodies that are obtained from one or more databases that store antibody sequences. Additionally, the classification output 514 can indicate an amount of similarity or an amount of difference between the generated sequence(s) 508 and the parent antibody sequence 512.

In examples, the challenging component 506 can label the generated sequence(s) 508 as zero and the structured sequences obtained from the protein sequence data 516 as 1. The challenging component 506 can also label the parent antibody sequence 512 as 1. In these situations, the classification output 514 can include a first number from 0 to 1 with respect to one or more amino acid sequences included in the antibody sequence data 516 and a second number from 0 to 1 with respect to the parent antibody sequence 512. In additional examples, the challenging component 506 can implement a distance function that produces an output that indicates an amount of distance between the generated sequence(s) 508 and the proteins included in the antibody sequence data 516. Further, the challenging component 506 can implement a distance function that produces an output that indicates an amount of distance between the generated sequence(s) 508 and the parent antibody sequence 512. In implementations where the challenging component 506 implements a distance function, the classification output 514 can include a first number from $-\infty$ to $\infty$ indicating a distance between the generated sequence(s) 508 and one or more sequences included in the antibody sequence data 516 and a second number from $-\infty$ to $\infty$ indicating a distance between the generated sequence(s) 508 and the parent antibody sequence 512.

In various implementations, the classification output 514 related to the amount of difference or the amount of similarity between the generated sequence(s) 508 and the parent antibody sequence 512 can be determined using a penalty function. In particular implementations, the challenging component 506 can evaluate the generated sequence(s) 508 with respect to the parent antibody sequence 512 in relation to an amount of similarity between the generated sequence(s) 508 and the parent antibody sequence 512 and/or an amount of dissimilarity between the generated sequence(s) 508 and the parent antibody sequence 512. In examples, a first threshold amount of dissimilarity between the generated sequence(s) 508 and the parent antibody sequence 512 can be specified. Additionally, a second threshold amount of similarity between the generated sequence(s) 508 and the parent antibody sequence 512 can be specified. The challenging component 506 can evaluate the generated sequence(s) 508 in relation to the parent antibody sequence 512 based on at least one of the first threshold amount of dissimilarity or the second threshold amount of similarity. In implementations, the challenging component 506 can implement the penalty function based on the amounts of similarity and/or dissimilarity between the generated sequence(s) 508 and the parent antibody sequence 512 in relation to the first threshold and/or the second threshold and utilize the output of the penalty function when generating the portion of the classification output 514 that corresponds to the parent antibody sequence 512 with respect to the generated sequence(s) 508.

The antibody sequences included in the antibody sequence data 516 can be subject to data preprocessing at 518 wherein the antibody sequences are mapped onto a classification system 520 before being provided to the challenging component 506. The classification system 520 can indicate that certain regions of antibodies are to be represented by particular numbers of positions. For example, a heavy chain variable region can be represented by 125 to 165 positions, such as 149 positions, within the classification system 520. In other examples, a heavy chain constant region can be represented by 110 to 140 positions, such as 123 positions, within the classification system 520. In additional examples, a hinge region of a heavy chain can be represented by 110 to 140 positions, such as 123 positions, within the classification system 520. In situations where an amino acid sequence of an antibody does not include a number of amino acids that corresponds to the specified number of positions for a region of the antibody, the data preprocessing at 518 can introduce a null value for one or more positions in the classification system 520. In implementations, the null regions can correspond to gaps that can indicate structural information of the antibodies. Thus, the classification system 520 can accommodate variable numbers of amino acids included in various regions of an antibody. Mapping the antibody sequences of at least a portion of the antibody sequence data 516 onto the classification system 520 can generate a standardized dataset that can be processed by the generative adversarial network 502 and that is independent of the number of amino acids included in individual regions of the antibodies.

In illustrative examples, the mapping of antibody sequences onto the classification system 520 taking place at 518 can include determining variable regions and constant regions of the antibodies. The variable regions and the constant regions of the antibodies can be determined by comparing the amino acid sequences included in the antibody sequence data 516 with template amino acid sequences that correspond to the various regions of the antibody. In particular examples, a position specific scoring matrix (PSSM) can be generated for each region type to determine alignment between the portions of the antibody sequences with the template amino acid sequences for the antibody regions. In situations where a local alignment is determined between an antibody sequence and a template sequence, antibody sequences produced from germline genes can be used to further determine positioning of individual amino acids of the antibody sequence within the classification system 520.

After the sequences related to the germline genes are used to identify a portion of an antibody sequence that may correspond to a particular type of antibody region, an amount of identity between a particular portion of an antibody sequence with a template sequence can be determined. In situations where a minimum number of amino acids in a given antibody sequence correspond to a template sequence and/or where an amount of identity between a template sequence and a given antibody sequence is at least a threshold amount of identity, the given antibody sequence can be classified as the particular region corresponding to the template. In an example, a given antibody sequence can be classified as being a complementarity determining region (CDR) of a heavy chain of an antibody. Additionally, individual antibody sequences that have been classified as being related to a particular region can also be assigned a score that can indicate a likelihood that a given antibody sequence corresponds to the classification. Portions of antibody sequences that have overlapping sequences can be filtered by score such that the highest scoring portion of the antibody sequence is assigned the classification. Gaps within the antibody sequences can be determined in situations where the number of amino acids for a given portion of an antibody sequence that has a particular classification is less than the number of positions assigned to classification in the classification system 520.

Although a particular classification system 520 has been described with respect to the illustrative example of FIG. 5, additional classification systems can be used in addition to, or in the alternative, with respect to the classification system 520. For example, the Kabat classification scheme, the Chotia classification scheme, the Martin classification scheme, the Gelfand classification scheme, the IMGT classification scheme, the Aho classification scheme, combinations thereof, and the like can be utilized to classify amino acid sequences of antibodies included in the antibody sequence data 516.

After the antibody sequence data 516 has been mapped onto the classification system 520 at 518, mapped sequence data 522 can be provided to the challenging component 506. The mapped sequence data 522 can include a matrix indicating the positions of amino acids for the regions of an antibody and indicating the amino acids associated with the individual positions. In situations where a gap is present in the amino acid sequence with respect to the classification system, a null value can be associated with each amino acid included in the matrix.

After the generative adversarial network 502 has undergone a training process, a trained model 524 can be generated that can produce sequences of proteins. In examples, the training process for the generative adversarial network 502 can be complete after the function(s) implemented by the generating component 504 converge. The convergence of a function can be based on the movement of values of model parameters toward particular values as antibody sequences are generated by the generating component 504 and feedback is obtained from the challenging component 506. In various implementations, the training of the generative adversarial network 502 can be complete when the antibody sequences produced by the generating component 504 have particular characteristics. To illustrate, the amino acid sequences generated by the generating component 504 can be analyzed by a software tool that can analyze amino acid sequences to determine at least one of biophysical properties of the amino acid sequences, structural features of the amino acid sequences, or adherence to amino acid sequences corresponding to one or more genes of at least one antibody germline.

Sequence input 526 can be provided to the model 524, and the model 524 can produce antibody sequences 528. The sequence input 526 can correspond to random or pseudo-random series of numbers having a specified length. In various implementations, the antibody sequences 528 can include variants of the parent antibody sequence 512. At 530, the antibody sequences 528 can be evaluated to determine whether the antibody sequences 528 have a specified set of characteristics. The sequence evaluation 530 can produce metrics 532 that indicate characteristics of the antibody sequences 528. Additionally, the metrics 532 can indicate an amount of correspondence between the characteristics of the antibody sequences 528 and a specified set of characteristics. In some examples, the metrics 532 can indicate a number of positions of an amino acid sequence 528 that vary from an amino acid sequence derived from a germline gene of an antibody.

Figure 6:
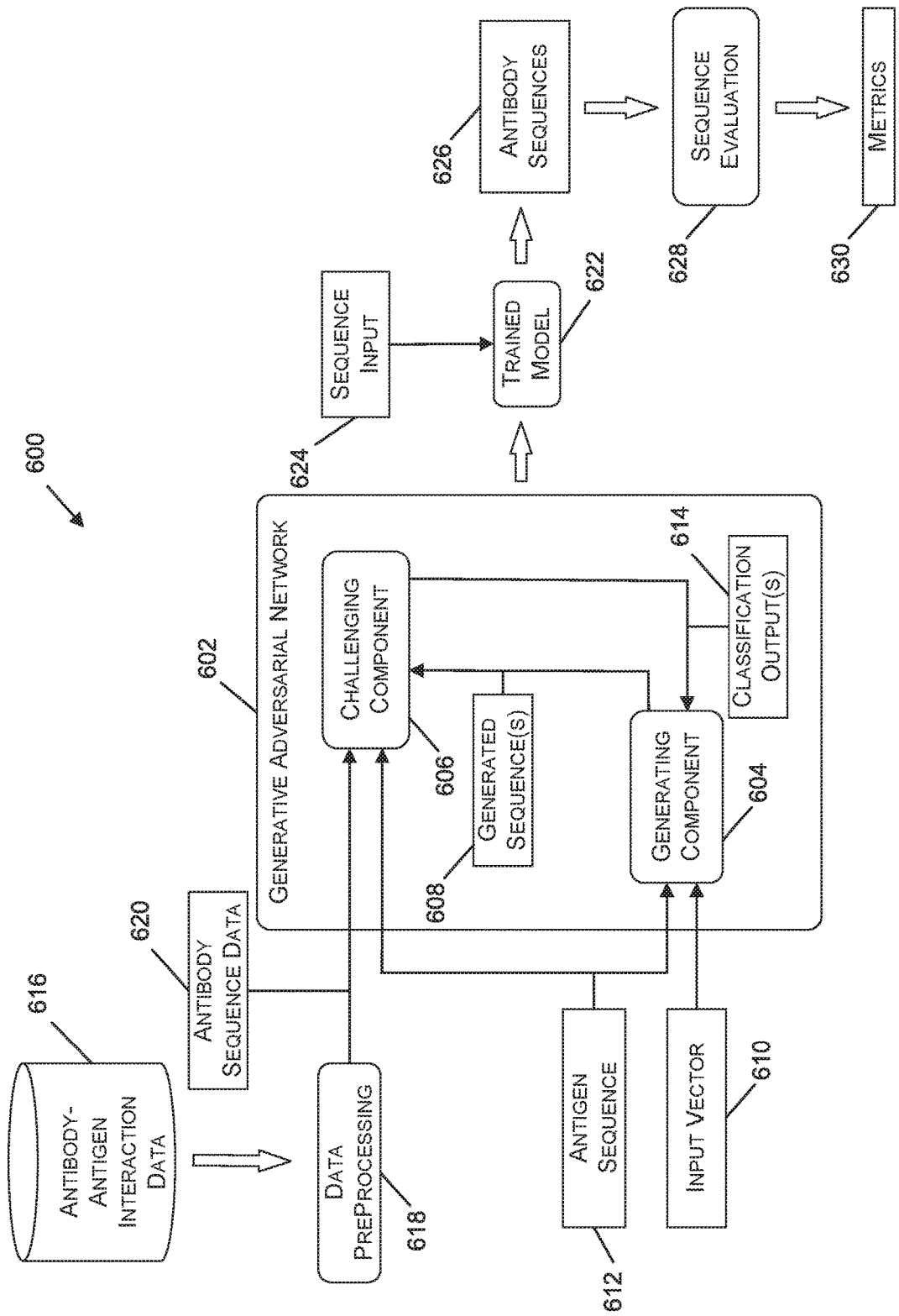
FIG. 6 is a diagram illustrating an example framework to generate amino acid sequences of antibodies that bind to a specified antigen, in accordance with some implementations.

FIG. 6 is a diagram illustrating an example framework 400 to generate amino acid sequences of antibodies that bind to a specified antigen, in accordance with some implementations. The framework 600 can include a generative adversarial network 602 that can include a generating component 604 and a challenging component 606. The generative adversarial network 602 can include a conditional generative adversarial network. The generating component 604 can implement a model to generate amino acid sequences based on input provided to the generating component 604. In various implementations, the model implemented by the generating component 604 can include one or more functions. In implementations, the generating component 604 can utilize a model to produce generated sequence(s) 608.

The generating component 604 can implement a model to generate amino acid sequences based on an input vector 610 provided to the generating component 604 and an antigen sequence 612. The input vector 610 can include a random or pseudo-random sequence of numbers of a specified length. The antigen sequence 612 can be provided to the generating component 604 as a matrix having columns corresponding to different amino acids and rows that correspond to structure-based positions of proteins. For each element in the matrix, a 0 can be used to indicate the absence of an amino acid at the corresponding position and a 1 can be used to indicate the presence of an amino acid at the corresponding position. The matrix can also include an additional column that represents a gap in an amino acid sequence where there is no amino acid at a particular position of the amino acid sequence. Thus, in situations where a position represents a gap in an amino acid sequence, a 1 can be placed in the gap column with respect to the row associated with the position where an amino acid is absent. The antigen sequence 612 can correspond to an antigen to which antibodies having amino acid sequences produced by the generating component 604 can bind. In various examples, the antigen sequence 612 can correspond to an antigen that has one or more epitope regions to which antibodies can bind. In one or more examples, the generative adversarial network 602 can produce amino acid sequences of antibodies to bind to the one or more epitope regions.

The challenging component 606 can generate output indicating whether the amino acid sequences produced by the generating component 604 have various characteristics. In implementations, the challenging component 606 can be a discriminator of the generative adversarial network 602. The challenging component 606 can generate classification output 614 indicating whether the amino acid sequences produced by the generating component 604 satisfy one or more criteria. In illustrative examples, based on similarities and differences between the generated sequence(s) 608 and additional sequences provided to the challenging component 606 as training data, such as amino acid sequences included in the antibody-antigen sequence data 616, the challenging component 606 can generate the classification output 614 to indicate an amount of similarity or an amount of difference between the generated sequence(s) 608 and sequences provided to the challenging component 606 from the antibody-antigen interaction data 616.

The antibody-antigen interaction data 616 can be obtained from one or more databases that store data related to the binding of antibodies to antigens. The antibody-antigen interaction data 616 can store amino acid sequences of antibodies and amino acid sequences of the antigens that are bound by the antibodies. The antibody-antigen interaction data 616 can also include information regarding at least one of secondary structures or tertiary structures of individual antibodies and individual antigens. In various examples, the antibody-antigen interaction data 616 can include information corresponding to at least one of secondary structures or tertiary structures of individual antibodies and individual antigens when they are bound to each other. Additionally, the antibody-antigen interaction data 616 can include amino acid sequences of epitope regions of antigens and amino acid sequences of corresponding binding regions of antibodies and at least one of the binding strength or the probability of binding by the various antibody regions to the respective epitope regions. In illustrative examples, the antibody-antigen interaction data 616 can indicate a number of positions of antigens that bind to one or more positions of the antibodies via non-covalent intermolecular interactions/ atomic interactions/chemical interactions, such as van der Waals forces, hydrogen bonding, electrostatic interactions, hydrophobic forces, combinations thereof, and the like.

In illustrative examples, the portions of the antibody-sequence data 616 provided to the challenging component 606 in relation to the antigen sequence 612 can include amino acid sequences of antibodies that have at least a minimum binding affinity with respect to the antigen sequence 612. A binding affinity of a portion of an amino acid sequence of an antibody with respect to the antigen sequence 612 can be determined based on a binding affinity of the portion of the amino acid sequence of the antibody with respect to antigens that have at least a threshold similarity with respect to the antigen sequence 612. For example, the antigen sequence 612 can be compared to amino acid sequences of antigens stored as part of the antibody-antigen interaction data 616. Antigens having amino acid sequences with at least a threshold amount of identity in relation to the antigen sequence 612 can be determined. Amino acid sequences of antibodies can then be identified that bind to the antigens and these amino acid sequences can be sent as input to the challenging component 606. In additional examples, amino acid sequences of epitope regions of antigens included in the antibody-antigen interaction data 616 can be compared with the antigen sequence 612. In these situations, epitope regions of antigens included in the antibody-antigen interaction data 616 that have at least a threshold amount of identity with one or more portions of the antigen sequence 612 can be determined. Antibodies that bind to these epitope regions can then be identified and sent as input to the challenging component 606.

The challenging component 606 can produce classification output 614 that labels a generated sequence 608 based on an amount of correspondence between the generated sequence 608 and training data provided to the challenging component 606. The training data can include at least a portion of the amino acid sequences included in the antibody-antigen interaction data 616. The classification output 614 can be based on a type of generative adversarial network associated with the generative adversarial network 602. For example, for a first type of generative adversarial network, the challenging component 606 can generate a classification output 614 of 1 for a generated sequence 608 that has at least a threshold amount of correspondence with respect to training data provided to the challenging component 820. Also, for the first type of generative adversarial network, the challenging component 606 can generate a classification output of 0 for a generated sequence 608 that has less than a threshold amount of correspondence with respect to training data provided to the challenging component 606. In various examples, for the first type of generative adversarial network, the challenging component 606 can generate classification output 614 that labels a generated sequence 608 using a numerical scale from 0 to 1 based on an amount of similarity between the generated sequence 608 and amino acid sequences included in training data provided to the challenging component 606.

Additionally, in situations where the generative adversarial network 602 implements a second type of generative adversarial network, such as a Wasserstein GAN, the challenging component 606 can implement a distance function that produces a classification output 614 that indicates an amount of distance between the generated sequences 608 and amino acid sequences included in training data provided to the challenging component 606. For example, the challenging component 606 can produce a classification output 614 that includes a number from $-\infty$ to $\infty$ that indicates a distance between a generated sequence 608 and at least a portion of the amino acid sequences included in the antibody-antigen interaction data 616. In various examples, the training data obtained from the antibody-antigen interaction data 616 can be referred to as ground truth data.

The amino acid sequences obtained from the antibody-antigen interaction data 616 can be subject to data preprocessing at 618. The amino acid sequences obtained from the antibody-antigen interaction data 616 can include at least one of amino acid sequences of antibodies or amino acid sequences of antigens. The amino acid sequences can be mapped onto a classification system as part of the data preprocessing 618 before being provided to the challenging component 606. For example, the classification system can indicate that certain regions of antibodies are to be represented by particular numbers of positions. In illustrative implementations, the classification system can be the same as or similar to the classification system 520 described with respect to FIG. 5. In various examples, the Kabat classification scheme, the Chotia classification scheme, the Martin classification scheme, the Gelfand classification scheme, the IMGT classification scheme, the Aho classification scheme, combinations thereof, and the like can be utilized to classify amino acid sequences of antibodies included in the antibody-antigen interaction data 616. Mapping at least a portion of the amino acid sequences included in the antibody-antigen interaction data 616 onto a classification system can generate a standardized dataset that can be processed by the generative adversarial network 602 and that is independent of the number of amino acids included in individual regions of the antibodies. After amino acid sequences obtained from the antibody-antigen interaction data 616 have been through the preprocessing 618, the antibody sequence data 620 that corresponds to the amino acid sequences can be sent to the challenging component 608.

Subsequent to the generative adversarial network 602 undergoing a training process, a trained model 622 can be generated that can produce sequences of antibodies. In examples, the training process for the generative adversarial network 602 can be complete after the function(s) implemented by the generating component 604 converge. The convergence of a function can be based on the movement of values of model parameters toward particular values as antibody sequences are generated by the generating component 604 and feedback is obtained from the challenging component 606. In various implementations, the training of the generative adversarial network 602 can be complete when the antibody sequences produced by the generating component 604 have particular characteristics. To illustrate, the amino acid sequences generated by the generating component 604 can be analyzed by a software tool that can determine at least one of biophysical properties of the amino acid sequences, structural features of the amino acid sequences, or adherence to amino acid sequences corresponding to one or more genes of at least one antibody germline.

Sequence input 624 can be provided to the trained model 622, and the trained model 622 can produce antibody sequences 626. The sequence input 624 can correspond to a random or pseudo-random series of numbers having a specified length. In illustrative examples, the sequence input 624 can include the antigen sequence 612. In additional examples, the sequence input 624 can include information indicating interactions between at least portions of one or more regions of one or more antibodies and portions of at least one or more regions of one or more antigens. At 628, the antibody sequences 626 can be evaluated to determine whether the antibody sequences 626 have a specified set of characteristics. For example, the sequence evaluation 628 can produce metrics 630 that indicate characteristics of the antibody sequences 626. Additionally, the metrics 630 can indicate an amount of correspondence between the characteristics of the antibody sequences 626 and a specified set of characteristics. The metrics 630 can also indicate characteristics, such as a number of hydrophobic amino acids included in an antibody 626 sequence, a number of positively charged amino acids included in an antibody sequence 626, a number of negatively charged amino acids included in an antibody sequence 626, a measure of a biophysical property of an antibody having an antibody sequence 626, a level of expression of an antibody having an antibody sequence 626, or one or more combinations thereof. In some examples, the metrics 630 can correspond to an amount of binding by an antibody to an antigen, interactions between an antibody and an antigen, an amount of interaction between an antigen and an amino acid sequence of an antibody derived from a germline gene.

Figure 7:
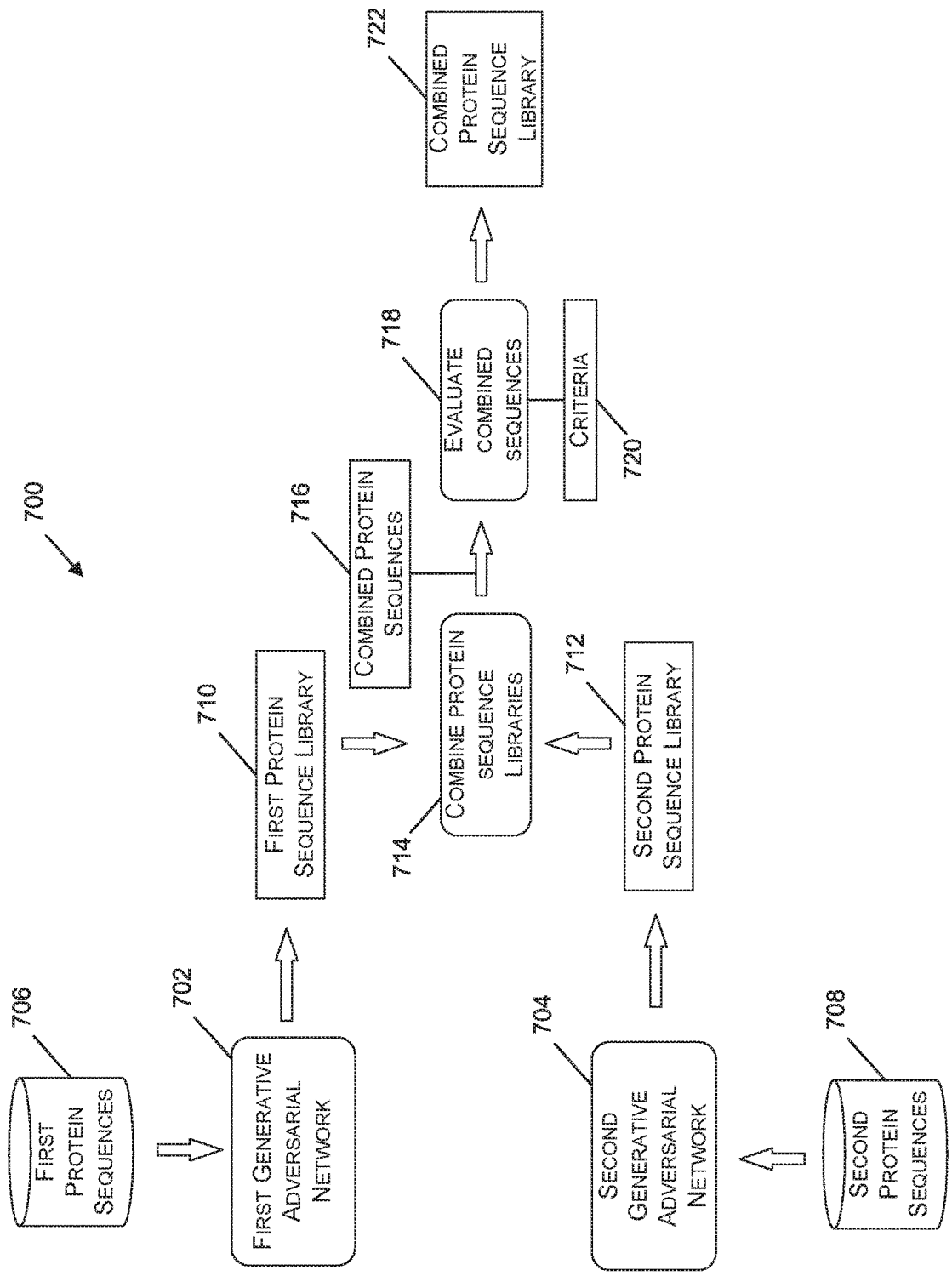
FIG. 7 is a diagram illustrating an example framework to generate multiple libraries of proteins and to combine the protein libraries to generate additional proteins, in accordance with some implementations.

FIG. 7 is a diagram illustrating an example framework 700 to generate multiple libraries of proteins and to combine the protein libraries to generate additional proteins, in accordance with some implementations. The framework 700 can include a first generative adversarial network 702 and a second generative adversarial network 704. The first generative adversarial network 702 can be trained and generate a model based on first protein sequences 706. Additionally, the second generative adversarial network 704 can be trained and generate an additional model based on second protein sequences 708. In various implementations, the first proteins sequences 706 and the second protein sequences 708 can include the same amino acid sequences. In additional implementations, the first protein sequences 706 can include at least one amino acid sequence that is different from the second protein sequences 708.

The first generative adversarial network 702 can produce a number of amino acid sequences of proteins that are included in a first protein sequence library 710. In addition, the second generative adversarial network 704 can produce a number of amino acid sequences that are included in a second protein sequence library 712. At least a portion of the amino acid sequences included in the first protein sequence library 710 can be different from the amino acid sequences included in the second protein sequence library 712. At 714, the first protein sequence library 710 and the second protein sequence library 712 can be combined to produce combined protein sequences 716.

At 718, the combined protein sequences 716 can be evaluated according to one or more criteria 720. For example, the combined protein sequences can be evaluated to determine whether the combined protein sequences 718 have particular regions of amino acid sequences, are associated with amino acid sequences that have specified biophysical properties, and/or are associated with amino acid sequences that have specified tertiary structures. In various implementations, the combined protein sequences 716 can be evaluated based on amino acid sequences of proteins derived from genes of a germline.

After the combined protein sequences 716 have been evaluated at 718, a combined protein sequence library 722 can be produced. The combined protein sequence library 722 can include at least a portion of the combined protein sequences 716. In particular implementations, the combined protein sequences 716 can be filtered according to the criteria 720 such that specified protein sequences included in the combined protein sequences are included in the combined protein sequence library.

In illustrative examples, the first protein sequence library 710 can include amino acid sequences that correspond to heavy chain regions of antibodies and the second protein sequence library 712 can include amino acid sequences that correspond to light chain regions of antibodies. In these situations, the heavy chain regions and the light chain regions can be combined to generate whole antibody amino acid sequences including both heavy chain regions and light chain regions. In various implementations, an additional generative adversarial network can be generated that can combine the amino acid sequences corresponding to the heavy chain regions with the amino acid sequences corresponding to the light chain regions.

Figure 8:
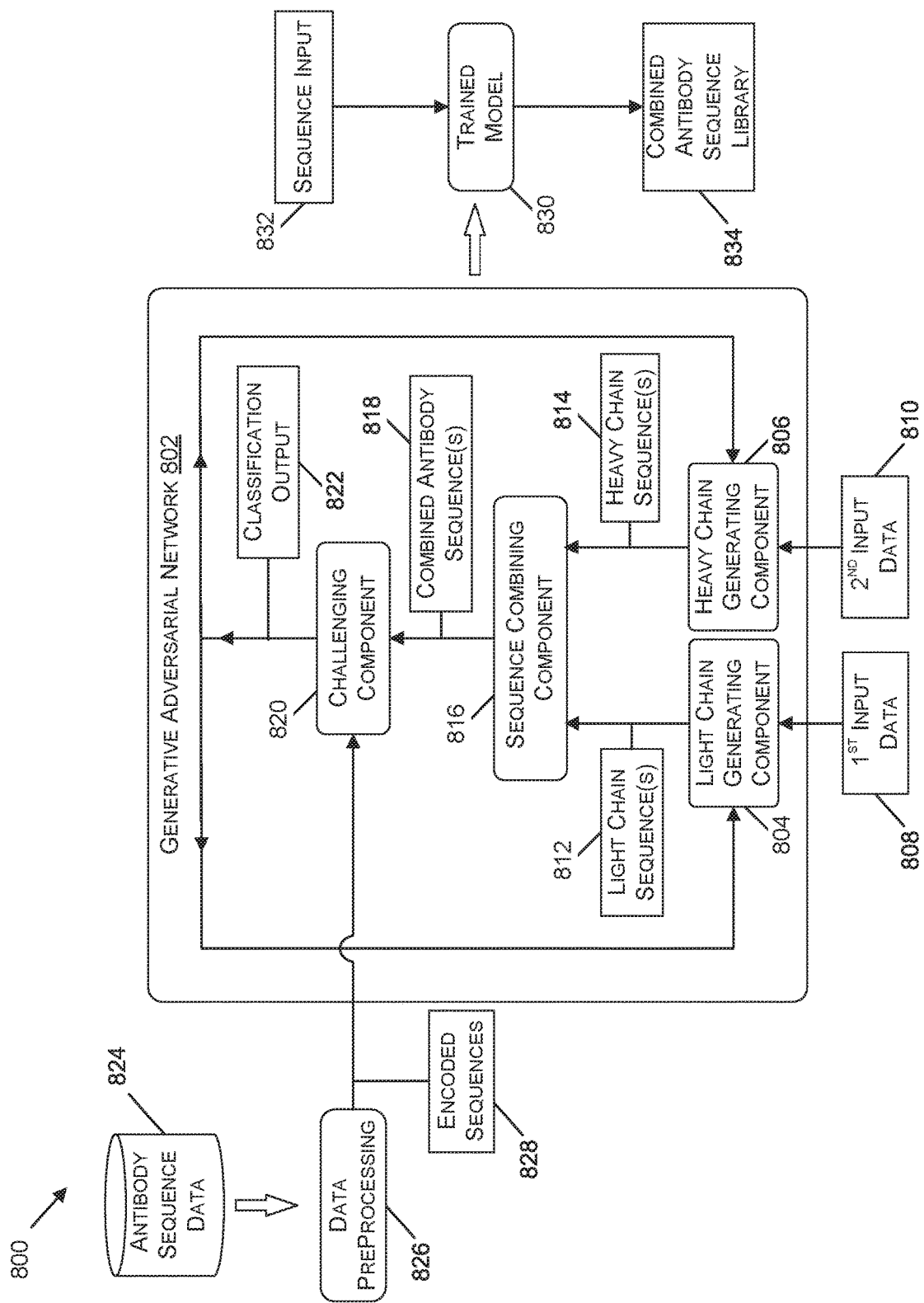
FIG. 8 is a diagram illustrating an additional example framework to generate amino acid sequences of antibodies using paired amino acid sequences of antibody heavy chains and light chains, in accordance with some implementations.

FIG. 8 is a diagram illustrating an additional example framework 800 to generate amino acid sequences of antibodies using separately generated amino acid sequences of paired antibody heavy chains and light chains, in accordance with some implementations. The framework 800 can include a generative adversarial network 802. The generative adversarial network 802 can implement one or more neural network technologies. For example, the generative adversarial network 802 can implement one or more recurrent neural networks. Additionally, the generative adversarial network 802 can implement one or more convolutional neural networks. In certain implementations, the generative adversarial network 802 can implement a combination of recurrent neural networks and convolutional neural networks.

The generative adversarial network 802 can include a light chain generating component 804 and a heavy chain generating component 806. The light chain generating component 804 can implement a first model to generate data corresponding to amino acid sequences of light chains of antibodies. In addition, the heavy chain generating component 806 can implement a second model to generate data corresponding to amino acid sequences of heavy chains of antibodies. The light chain generating component 804 can implement a first model to generate amino acid sequences of light chains of antibodies based on first input data 808 provided to the light chain generating component 804. The heavy chain generating component 806 can implement a second model to generating amino acid sequences of heavy chains of antibodies based on second input data 810. The first input data 808 can include first noise data generated by a random number generator or a pseudo-random number generator. The second input data 810 can include second noise data generated by a random number generator or a pseudo-random number generator. In various implementations, the first model implemented by the light chain generating component 804 can include one or more first functions that each include one or more first variables having respective first weights. The second model implemented by the heavy chain generating component 806 can include one or more second functions that each include one or more second variables having respective second weights.

The light chain generating component 804 can implement a first model to produce light chain sequences 812 based on the first input data 808. The light chain sequences 812 can comprise data corresponding to amino acids that are located at positions of an antibody light chains. The light chain sequences 812 can include sequences of amino acids of antibody light chains that are encoded according to one or more encoding schemes. In various examples, the light chain sequences 812 can include data corresponding to amino acids at individual positions of antibody light chains that is encoded according to a schema. In one or more illustrative examples, the light chain sequences 812 can include amino acid sequences of antibody light chains that are encoded according to a one-hot encoding scheme.

The heavy chain generating component 806 can implement a second model to produce heavy chain sequences 814 based on the second input data 810. The heavy chain sequences 814 can comprise data corresponding to amino acids that are located at positions of antibody heavy chains. The heavy chain sequences 814 can include sequences of amino acids of antibody light chains that are encoded according to one or more encoding schemes. In various examples, the heavy chain sequences 814 can include data corresponding to amino acids at individual positions of antibody heavy chains that is encoded according to a schema. In one or more illustrative examples, the heavy chain sequences 814 can include amino acid sequences of antibody heavy chains that are encoded according to a one-hot encoding scheme.

The light chain sequences 812 and the heavy chain sequences 814 can be provided to a sequence combining component 816. The sequence combining component 816 can combine at least one light chain sequence 812 and at least one heavy chain sequence 814 to generate a combined antibody sequence 818. In various implementations, the sequence combining component 816 can combine a single light chain sequence 812 with a single heavy chain sequence 814. A combined antibody sequence 818 can include data corresponding to amino acids located at positions of one or more light chain sequences 812 and one or more heavy chain sequences 814. In one or more examples, the sequence combining component 816 can generate a combined antibody sequence 818 by concatenating one or more light chain sequences 812 and one or more heavy chain sequences 814. For example, the sequence combining component 816 can add a first string of alphanumeric characters representative of an antibody light chain sequence to a second string of alphanumeric characters representative of an antibody heavy chain sequence to generate a combined antibody sequence 818. The combined antibody sequence 818 can include a first portion that corresponds to a light chain sequence 812 and a second portion that corresponds to a heavy chain sequence 814. For example, a first number of positions of a combined antibody sequence 818 can correspond to amino acids of a light chain sequence 812 and a second number of positions of the combined antibody sequence 818 that are after the first number of positions can correspond to a heavy chain sequence 814. In additional examples, a first number of positions of a combined antibody sequence 818 can correspond to amino acids of a heavy chain sequence 814 and a second number of positions of the combined antibody sequence 818 that are after the first number of positions can correspond to a light chain sequence 812. In various implementations, the combined antibody sequence 818 can correspond to amino acids of one or more light chain sequences 812 and one or more heavy chain sequences 814 arranged according to a schema.

The generative adversarial network 802 can include a challenging component 820. The challenging component 820 can generate output indicating that the combined antibody sequences 818 satisfy or do not satisfy one or more characteristics. The challenging component 820 can produce classification output 822 that can be provided to the light chain generating component 804 and the heavy chain generating component 806. The challenging component 820 can evaluate the combined antibody sequences 818 with respect to training data that comprises the antibody sequence data 824. The challenging component 820 can compare the combined antibody sequences 818 generated by the sequence combining component 816 with at least a portion of the amino acid sequences included in the antibody sequence data 824. The classification output 822 generated based on the comparisons can indicate an amount of correspondence between a combined antibody sequence 818 with respect to at least a portion of the amino acid sequences included in the antibody sequence data 824. For example, based on similarities and differences between a combined antibody sequence 818 and at least a portion of the amino acid sequences included in the antibody sequence data 824, the classification output 822 generated by the challenging component 820 can indicate an amount of similarity or an amount of difference between the combined antibody sequence 818 and at least a portion of the amino acid sequences included in the antibody sequence data 824.

The challenging component 820 can produce classification output 822 that labels a combined antibody sequence 818 based on an amount of correspondence between the combined antibody sequence 818 and training data provided to the challenging component 820. The training data can include at least a portion of the amino acid sequences included in the antibody sequence data 824. The classification output 822 can be based on a type of generative adversarial network associated with the generative adversarial network 802. For example, for a first type of generative adversarial network, the challenging component 820 can generate a classification output 822 of 1 for a combined antibody sequence 818 that has at least a threshold amount of correspondence with respect to training data provided to the challenging component 820. Also, for the first type of generative adversarial network, the challenging component 820 can generate a classification output of 0 for a combined antibody sequence 818 that has less than a threshold amount of correspondence with respect to training data provided to the challenging component 820. In various examples, for the first type of generative adversarial network, the challenging component 820 can generate classification output 822 that labels a combined antibody sequence 818 using a numerical scale from 0 to 1 based on an amount of similarity between the combined antibody sequence 818 and amino acid sequences included in training data provided to the challenging component 820.

Additionally, in situations where the generative adversarial network 802 implements a second type of generative adversarial network, such as a Wasserstein GAN, the challenging component 820 can implement a distance function that produces a classification output 822 that indicates an amount of distance between the combined antibody sequences 818 and amino acid sequences included in training data provided to the challenging component 820. For example, the challenging component 820 can produce a classification output 822 that includes a number from $-\infty$ to $\infty$ that indicates a distance between a combined antibody sequence 818 and at least a portion of the amino acid sequences included in the antibody sequence data 824. In various examples, the training data obtained from the antibody sequence data 824 can be referred to as ground truth data.

The amino acid sequences included in the antibody sequence data 824 can be subject to data preprocessing 826 before being provided to the challenging component 820. In implementations, the data preprocessing 826 can include arranging the antibody sequence data 824 according to a classification system before being provided to the challenging component 820. For example, the data preprocessing 826 can include pairing amino acids included in the amino acid sequences of the antibody sequence data 824 with numerical values that can represent structure-based positions within the antibodies. The numerical values can include a sequence of numbers having a starting point and an ending point. In an illustrative example, a T can be paired with the number 43 indicating that a Threonine molecule is located at a structure-based position 43 of a specified antibody.

The output produced by the data preprocessing 826 can include structured sequences 828. The structured sequences 828 can include a matrix indicating amino acids associated with various positions of an antibody. In examples, the structured sequences 828 can include a matrix having columns corresponding to different amino acids and rows that correspond to structure-based positions of antibodies. For each element in the matrix, a 0 can be used to indicate the absence of an amino acid at the corresponding position and a 1 can be used to indicate the presence of an amino acid at the corresponding position. In situations where a position represents a gap in an amino acid sequence, the row associated with the position can comprise zeroes for each column. The combined antibody sequence(s) 818 can also be represented using a vector according to a same or similar number scheme as used for the structured sequences 828. In some illustrative examples, the structured sequences 828 and the combined antibody sequence(s) 818 can be encoded using a method that may be referred to as a one-hot encoding method. In various implementations, the structured sequences 828 can include an amino acid sequence of an antibody light chain followed by an amino acid sequence of an antibody heavy chain. In additional implementations, the structured sequences 828 can include an amino acid sequence of an antibody heavy chain followed by an amino acid sequence of an antibody light chain. The arrangement of antibody light chains and antibody heavy chains in the structured sequences 828 can correspond to the arrangement of antibody light chains and antibody heavy chains included in the combined antibody sequences 818.

In various examples, training of the light chain generating component 804 and the heavy chain generating component 806 can take place asynchronously. For example, the training of the heavy chain component 806 may cease for a period of time while training of the light chain generating component 804 continues. In one or more examples, the light chain generating component 804 and the heavy chain generating component 806 can train concurrently for a period of time. During this period of time, the training of the heavy chain generating component 806 may progress faster than training of the light chain generating component 804. In these situations, the training of the heavy chain generating component 806 may cease for a period of time that the light chain generating component 804 continues to train. In some examples, sequences generated by the heavy chain generating component 806 may be evaluated at various points in time to determine a metric with regard to quality of the amino acid sequences generated by the heavy chain generating component 806. In various examples, the training of the heavy chain generating component 806 may cease when the metric satisfies one or more threshold metrics. The light chain generating component 804 may continue to train until the sequences produced by the light chain generating component 804 satisfy the one or more threshold metrics. After sequences from both the light chain generating component 804 and the heavy chain generating component 806 satisfy the one or more threshold metrics, the light chain generating component 804 and the heavy chain generating component 806 can continue to train. In one or more examples, training of the light chain generating component 804 and the heavy chain generating component 806 can train until one or more metrics used to evaluate the sequences produced by the light chain generating component 804 and the heavy chain generating component 806 diverge by at least a threshold amount.

In one or more illustrative examples, the training of the heavy chain generating component 806 can implement hobbled weights such that the training of the light chain generating component 804 and the training of the heavy chain generating component 806 proceed at relatively similar rates. Additionally, the training of the heavy chain generating component 806 may proceed with slower gradients such that the training of the light chain generating component 804 and the training of the heavy chain generating component 806 proceed at relatively similar rates.

After the generative adversarial network 802 has undergone a training process, a trained model 830 can be generated that can produce amino acid sequences of antibodies. The trained model 830 can include the light chain generating component 804 and the heavy chain generating component 806 after a training process using the antibody sequence data 824. In examples, the training process for the generative adversarial network 802 can be complete after the classification output 822 indicates at least a threshold amount of correspondence between the combined antibody sequences 818 and the amino acid sequences included in the antibody sequence data 824. In additional implementations, the training of the generative adversarial network 802 can be complete when the combined antibody sequences 818 have particular characteristics. To illustrate, the amino acid sequences generated by the sequence combining component 816 can be analyzed by a software tool that can analyze amino acid sequences to determine at least one of biophysical properties of the amino acid sequences, structural features of the amino acid sequences, or adherence to amino acid sequences corresponding to one or more protein germlines. The characteristics of the combined antibody sequences 818 determined by the analysis of the software tool in relation to specified characteristics can be used to determine whether or not the training of the generative adversarial network 802 is complete.

Sequence input 832 can be provided to the trained model 830, and the trained model 830 can produce a combined antibody sequence library 834. The sequence input 832 can correspond to random or pseudo-random series of numbers that can be used to produce the combined antibody sequence library 834. The combined antibody sequence library 834 can include amino acid sequences of antibodies that include at least one light chain and at least one heavy chain that correspond to the individual antibodies included in the combined antibody sequence library 834. The amino acid sequences included in the combined antibody sequence library 834 that are produced by the trained model 830 can be represented as a matrix structure that is the same as or similar to the matrix structure used to represent the structured sequences 828 and/or the combined antibody sequence(s) 818. In various implementations, the matrices produced by the trained model 830 that comprise the amino acid sequences included in the combined antibody sequence library 834 can be decoded to produce a string of amino acids that correspond to the sequence of an antibody.

In some implementations, the amino acid sequences included in the combined antibody sequence library 834 can be subject to one or more filtering operations. The one or more filtering operations can parse the amino acid sequences included in the combined antibody sequence library for one or more of the sequences that correspond to one or more specified characteristics. For example, the amino acid sequences included in the combined antibody sequence library 834 can be analyzed to identify sequences that have specified amino acids at particular positions. The amino acid sequences included in the combined antibody sequence library 834 can also be analyzed to identify one or more sequences that have one or more particular strings of amino acids at one or more locations. In various implementations, the amino acid sequences included in the combined antibody sequence library 834 can be analyzed to identify one or more sequences that have a set of biophysical properties based on similarities between at least one of the sequences included in the combined antibody sequence library 834 and amino acid sequences of additional antibodies that are known to have the set of biophysical properties.

In one or more implementations, amino acid sequences generated by the trained model 830 and/or amino acid sequences generated during the training of the light chain generating component 804 and the heavy chain generating component 806 may be evaluated according to one or more criteria. For example, amino acid sequence generated the trained model 830 and/or amino acid sequences generated during the training of the light chain generating component 804 and the heavy chain generating component 806 may be evaluated based on at least one of agreement with amino acid sequences produced in relation to one or more germline genes, a measure of immunogenicity of the amino acid sequences, or agreement with CDR H3 amino acid sequences. A PCA model may be used to determine when to stop training at least one of the light chain generating component 804 or the heavy chain generating component 806 in relation to correspondence with CDR H3 regions. In various examples, the measure of immunogenicity can correspond to MHC Class II binding affinity.

Figure 9:
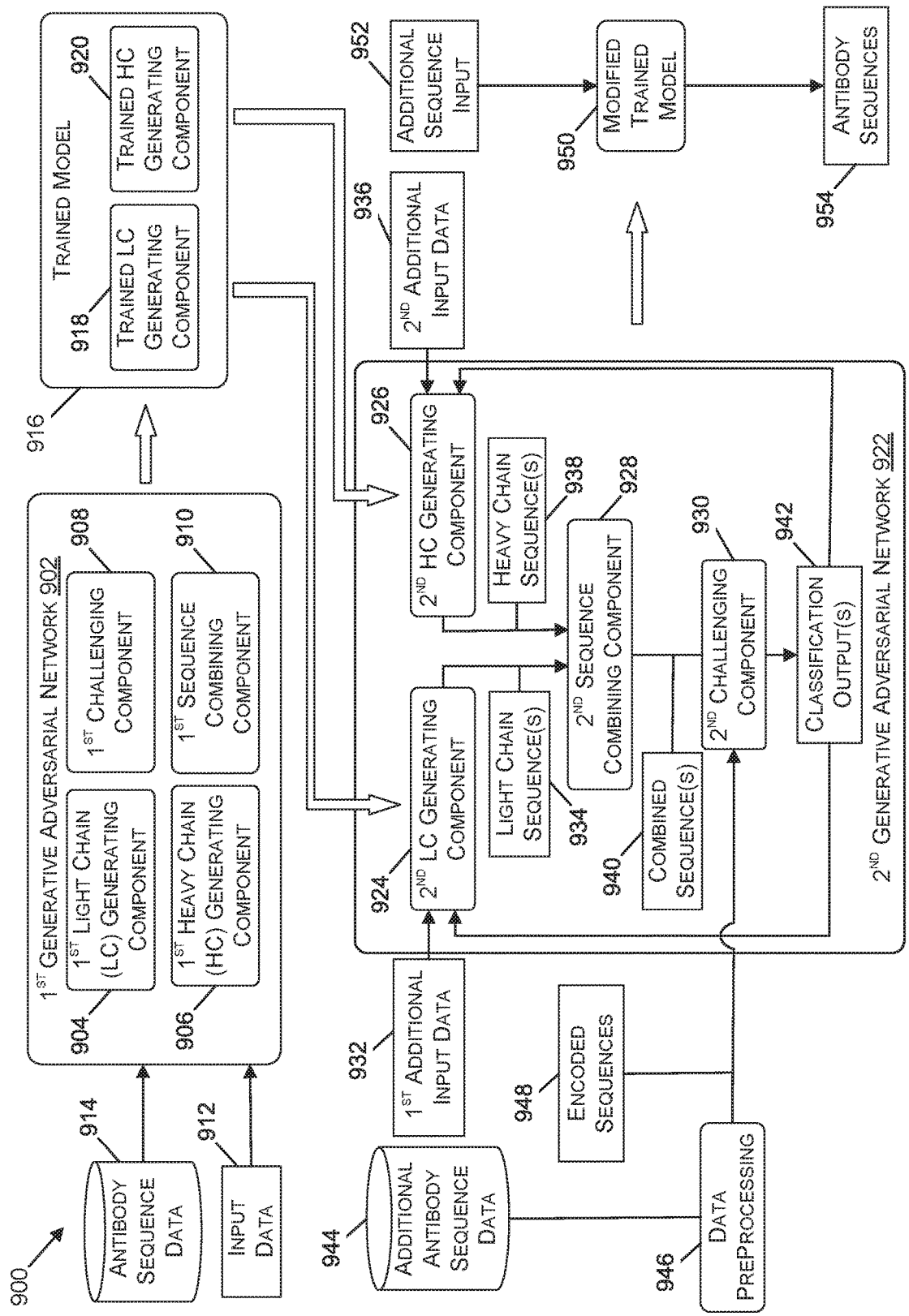
FIG. 9 is a diagram illustrating a framework that implements the use of transfer learning techniques to generate paired amino acid sequences of antibodies from amino acid sequences of antibody heavy chains and light chains, in accordance with some implementations.

FIG. 9 is a diagram illustrating a framework 900 that implements the use of transfer learning techniques to generate amino acid sequences of antibodies from amino acid sequences of paired antibody heavy chains and light chains, in accordance with some implementations. The framework 900 can include a first generative adversarial network 902. The first generative adversarial network 902 can include a first light chain generating component 904, a first heavy chain generating component 906, a first challenging component 908, and a first sequence combining component 910. In various implementations, the first challenging component 908 can be a discriminator. The first light chain generating component 904 can implement a model to generate amino acid sequences of antibody light chains based on input provided to the first light chain generating component 904. The first heavy chain generating component 906 can implement a model to generate amino acid sequences of antibody heavy chains based on input provided to the first heavy chain generating component 906. The first light chain generating component 904 and the first heavy chain generating component 906 can use input data 912 to generate amino acid sequences. The input data 912 can include a vector produced using a random number generator or a pseudo-random number generator. In illustrative examples, the input data 912 can include a noise signal that includes a series of numbers.

The first sequence combining component 910 can combine amino acid sequences generated by the first light chain generating component 904 with amino acid sequences generated by the first heavy chain generating component 906 to produce combined antibody sequences. The first sequence combining component 910 can provide the combined antibody sequences to the first challenging component 908. The first challenging component 908 can then generate output indicating whether the combined antibody sequences satisfy various characteristics. The output produced by the first challenging component 908 can be provided as feedback to at least one of the first light chain generating component 904 and the first heavy chain generating component 906. In this way, one or more models implemented by the first light chain generating component 904 and/or the first heavy chain generating component 906 can be modified based on the feedback provided by the first challenging component 908. In various implementations, the first challenging component 908 can compare the amino acid sequences produced by the first sequence combining component 910 with amino acid sequences of antibodies that correspond to training data for the first generative adversarial network 902 and generate an output indicating an amount of correspondence between the amino acid sequences produced by the first sequence combining component 910 and the amino acid sequences of antibodies included in the training data. The training data can include antibody sequence data 914. The antibody sequence data 914 can correspond to amino acid sequences of a number of antibodies. For a given antibody, the antibody sequence data 914 can include a pairing of an antibody light chain and an antibody heavy chain. In illustrative examples, the antibody sequence data 914 can include amino acid sequences of antibodies produced by one or more mammals. The antibody sequence data 914 can also include amino acid sequences of one or more isotypes of classes of antibodies, such as IgA antibodies, IgD antibodies, IgE antibodies, IgG antibodies, and/or IgM antibodies.

The first generative adversarial network 902 can be trained in a same or similar manner described with respect to the generative adversarial network 802 of FIG. 6. For example, at least a portion of the antibody sequence data 914 can be fed into the first challenging component 908 and compared against output produced by the first sequence combining component 910. The output produced by the first sequence combining component 910 can be based on amino acid sequences of antibody light chains generated by the first light chain generating component 904 and amino acid sequences of antibody heavy chains generated by the first heavy chain generating component 906. A trained model 916 can be produced in response to iteratively determining parameters and/or weights with respect to one or more functions implemented by at least one of the first light chain generating component 904 or the first heavy chain generating component 906. To illustrate, the trained model 916 can include a trained light chain generating component 918 and a trained heavy chain generating component 920.

In various examples, the amino acid sequences generated by the trained model 916 can be refined further. To illustrate, the trained model 916 can be modified by being subjected to another training process using a different set of training data than the training data used in the initial training process. For example, the data used for additional training of the trained model 916 can include a subset of the data used to initially produce the trained model 916. In additional examples, the data used for additional training of the trained model 916 can include a different set of data than the data used to initially produce the trained model 916. In illustrative examples, the trained model 916 can be further refined to generate amino acid sequences of antibodies having one or more specified attributes. The one or more specified attributes can include values of one or more biophysical properties and/or one or more levels of expression. In these scenarios, the trained model 916 can be further trained using a training dataset that includes amino acid sequences of antibodies that have the one or more specified attributes.

In the illustrative example of FIG. 9, the refinement of the trained model 916 can be represented by training a second generative adversarial network 922 that includes the training model 916. For example, the second generative adversarial network 922 can include a second light chain generating component 924 that initially corresponds to the trained light chain generating component 918 and a second heavy chain generating component 926 that initially corresponds to the trained heavy chain generating component 920. In various implementations, the second light chain generating component 924 can include the trained light chain generating component 918 after one or more modifications have been made to the trained light chain generating component 918. Additionally, the second heavy chain generating component 926 can include the trained heavy chain generating component 920 after one or more modifications have been made to the trained heavy chain generating component 920. For example, modifications can be made to the trained light chain generating component 918 in relation to the architecture of the trained light chain generating component 918, such as the addition of one or more hidden layers or changes to one or more network filters. The second generative adversarial network 922 can also include a second sequence combining component 928 and a second challenging component 930. The second challenging component 930 can include a discriminator.

First additional input data 932 can be provided to the second light chain generating component 924 and the second light chain generating component 924 can produce one or more light chain sequences 934. The first additional input data 932 can include a random or pseudo-random sequence of numbers that the second light chain generating component 924 uses to produce the light chain sequences 934. Further, second additional input data 936 can be provided to the second heavy chain generating component 926 and the second heavy chain generating component 926 can produce one or more heavy chain sequences 938. The second additional input data 932 can include a random or pseudo-random sequence of numbers that the second heavy chain generating component 926 uses to produce the heavy chain sequences 938. The second sequence combining component 928 can combine one or more light chain sequences 934 with one or more heavy chain sequences 938 to produce one or more combined sequences 940. The one or more combined sequences 940 can correspond to amino acid sequences of antibodies that include at least one light chain and at least one heavy chain.

The second challenging component 930 can generate classification output 942 indicating that the amino acid sequences included in the combined sequences 940 satisfy various characteristics or that the amino acid sequences included in the combined sequences 940 do not satisfy various characteristics. In illustrative examples, the second challenging component 930 can generate the classification output 942 based on similarities and differences between one or more combined sequences 940 and amino acid sequences provided to the second challenging component 930 as training data. The classification output 942 can indicate an amount of similarity or an amount of difference between the combined sequences 940 and the training data amino acid sequences provided to the second challenging component 930.

The amino acid sequences provided to the second challenging component 930 as training data can be included in additional antibody sequence data 944. The additional antibody sequence data 944 can include amino acid sequences of proteins that have one or more specified characteristics. For example, the additional antibody sequence data 944 can include amino acid sequences of antibodies having a threshold level of expression in humans. In additional examples, the additional antibody sequence data 944 can include amino acid sequences of antibodies having one or more biophysical properties and/or one or more structural properties. To illustrate, the antibodies included in the additional antibody sequence data 944 can have negatively charged regions, hydrophobic regions, a relatively low probability of aggregation, a specified percentage of high molecular weight (HMW), melting temperature, one or more combinations thereof, and the like. In one or more additional examples, the additional antibody sequence data 944 may include binding affinity information that can be used in transfer learning. In one or more illustrative examples, the additional antibody sequence data 944 can correspond to antibodies that have at least a threshold amount of binding affinity with respect to one or more molecules, such as MHC Class II molecules. In various examples, the additional antibody sequence data 944 can include a subset of the antibody sequence data 914 used to produce the trained model 916. By providing amino acid sequences to the second challenging component 930 that have one or more specified characteristics, the second light chain generating component 924 and the second heavy chain generating component 926 can be trained to produce amino acid sequences of antibodies that have at least a threshold probability of having the one or more specified characteristics.

Additionally, in many situations where it is desired to produce amino acid sequences of antibodies having one or more specified characteristics, the number of sequences available to train a generative adversarial network can be limited. In these situations, the accuracy, efficiency, and/or effectiveness of the generative adversarial network to produce amino acid sequences of antibodies having the specified characteristics may be unsatisfactory. Thus, without a sufficient number of amino acid sequences available to train a generative adversarial network, the amino acid sequences produced by the generative adversarial network may not have the desired characteristics. By implementing the techniques and systems described with respect to FIG. 9, a first generative adversarial network 902 can perform part of the process of training a model to produce antibodies having the one or more specified characteristics and the second generative adversarial network 922 can perform additional training to generate amino acid sequences of antibodies having the one or more specified characteristics in an accurate and efficient manner.

Before being provided to the second challenging component 930, the amino acid sequences included in the additional antibody sequence data 944 can be subject to data preprocessing 946 that produces structured sequences 948. For example, the additional protein sequence data 944 can be arranged according to a classification system before being provided to the second challenging component 930. The data preprocessing 946 can include pairing amino acids included in the amino acid sequences of antibodies included in the additional protein sequence data 944 with numerical values that can represent structure-based positions within the antibodies. The combined sequence(s) 940 can also be represented using a vector according to a same or similar number scheme as used for the structured sequences 948.

After the second generative adversarial network 922 has undergone a training process, a modified trained model 950 can be generated that can produce amino acid sequences of antibodies. The modified trained model 950 can represent the trained model 916 after being trained using the additional protein sequence data 944. Additional sequence input 952 can be provided to the modified trained model 950, and the modified trained model 950 can produce antibody sequences 954. The additional sequence input 952 can include a random or pseudo-random series of number. In additional implementations, the antibody sequences 954 can be evaluated to determine whether the antibody sequences 954 have a specified set of characteristics. The evaluation of the antibody sequences 954 can produce metrics that indicate characteristics of the antibody sequences 954, such as biophysical properties of an antibody, biophysical properties of a region of an antibody, and/or the presence or absence of amino acids located at specified positions of an antibody.

While the illustrative example of FIG. 9 illustrates the training of a model using multiple training sets in a framework that includes two generative adversarial networks. in additional implementations, the training of a model using multiple training datasets can also be represented using a single generative adversarial network. Further, while the illustrative example of FIG. 9 illustrates the training of a model using generative adversarial networks with two training datasets, in various implementations, more than two datasets can be used to train models using one or more generative adversarial networks according to implementations described herein.

Additionally, although the illustrative example of FIG. 9 shows that the second generative adversarial network 922 uses the trained model 916 having a light chain generating component 918 that is separate from a trained heavy chain generating component 920, in additional implementations, the trained model 916 used by the second generative adversarial network 922 as the generating component can be a single generating component that can be used to generate amino acid sequences that include both light chains and heavy chains. In these implementations, the second generative adversarial network 922 can include a single generating component instead of both a second light chain generating component 924 and a second heavy chain generating component 926 and the second sequence combining component 928 can be absent from the second generative adversarial network 922. In various implementations, a single generating component can be implemented by the second generative adversarial network 922 instead of a separate light chain generating component and a heavy chain generating component in scenarios where interactions between amino acids of the light chains and the heavy chains introduce one or more complexities that are more efficiently captured using a generative adversarial network having a single generating component. Further, in one or more implementations, additional layers can be added to the second generative adversarial network 922 to generate amino acid sequences of antibodies. In various implementations, one or more additional layers can be added to the second generative adversarial network 922 after, or as part of, the second sequence combining component 928 to generate the combined sequences 940.

Figure 10:
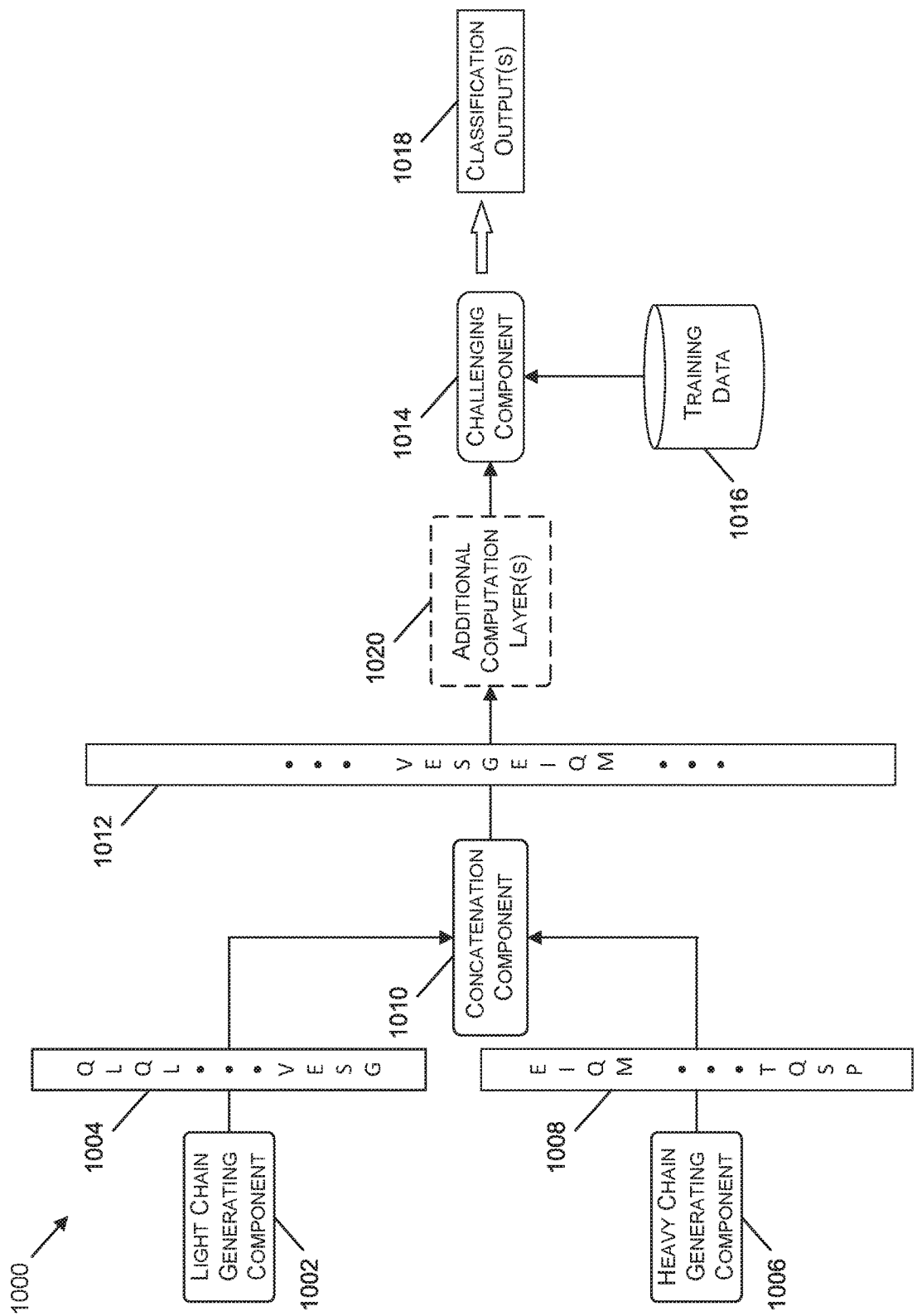
FIG. 10 is a diagram illustrating a framework for the concatenation of amino acid sequences of antibody heavy chains and light chains, in accordance with some implementations.

FIG. 10 is a diagram illustrating a framework 1000 for the concatenation of amino acid sequences of antibody heavy chains and light chains, in accordance with some implementations. The framework 1000 can include a light chain generating component 1002 that generates data corresponding to a first amino acid sequence 1004 of a light chain of an antibody. The light chain generating component 1002 can be part of a generative adversarial network. In addition, the light chain generating component 1002 can implement one or more first models to produce data corresponding to amino acid sequences of antibody light chains. The one or more first models can include one or more functions having one or more variables, one or more parameters, one or more weights, or one or more combinations thereof. The light chain generating component 1002 can produce the data corresponding to amino acid sequences of antibody light chains based on input data obtained by the light chain generating component 1002. The input data can include numerical data produced by a random number generator or a pseudo-random number generator.

The framework 1000 can also include a heavy chain generating component 1006 that generates data corresponding to a second amino acid sequence 1008 of a heavy chain of an antibody. The heavy chain generating component 1006 can be a part of a generative adversarial network. In various implementations, the heavy chain generating component 1006 can implement one or more second models to produce data corresponding to amino acid sequences of antibody heavy chains. The one or more second models can include one or more additional functions having one or more variables, one or more parameters, one or more weights, or one or more combinations thereof. The heavy chain generating component 1006 can produce the data corresponding to amino acid sequences of antibody heavy chains based on additional input data obtained by the heavy chain generating component 1006. The additional input data can include numerical data produced by a random number generator or a pseudo-random number generator.

Additionally, the framework 1000 can include a concatenation component 1010 that combines the first amino acid sequence 1004 and the second amino acid sequence 1008 to produce data corresponding to a third amino acid sequence 1012. The concatenation component 1010 can append the second amino acid sequence 1008 onto the first amino acid sequence 1004. For example, the first amino acid sequence 1004 can include a first string of letters with each letter in the first string indicating an amino acid located at a respective position of a light chain of an antibody. Further, the second amino acid sequence 1008 can include a second string of letters with each letter in the second string indicating an amino acid located at a respective position of a heavy chain of an antibody. The third amino acid sequence 1012 generated by the concatenation component 1010 can include a third string of letters that is produced by adding the second string of letters included in the second amino acid sequence 1008 after a last letter of the first string of letters included in the first amino acid sequence 1004. To illustrate, the first amino acid sequence 1004 terminates in VESG and the second amino acid sequence 1008 begins with EIQM. The concatenation component 1010 can combine the first amino acid sequence 1004 with the second amino acid sequence 1008 by adding the second amino acids sequence 1008 starting with EIQM after the VESG of the first amino acid sequence 1004. In this way, the third amino acid sequence 1012 includes a number of amino acids that corresponds to a combination of a first number of amino acids included in the first amino acid sequence 1004 and a second number of amino acids included in the second amino acid sequence 1008.

The third amino acid sequence 1012 can be provided to a challenging component 1014 that can evaluate the third amino acid sequence 1012 against training data 1016. The challenging component 1014 can be included in a generative adversarial network. In illustrative examples, the challenging component 1014 can be a discriminator of a generative adversarial network. The training data 1016 can include amino acid sequences of antibodies. The amino acid sequences included in the training data 1016 can correspond to antibodies that are produced by various organisms and that have been analyzed to determine the amino acid sequences of the antibodies. In various examples, the training data 1016 can include at least one of amino acid sequences of antibody light chains, amino acid sequences of antibody heavy chains, or amino acid sequences of combinations of antibody light chains with antibody heavy chains. By evaluating the amino acid sequences generated by the concatenation component 1010, such as the third amino acid sequence 1012, in relation to the training data 1016, the challenging component 1014 can generate classification output 1018. The classification output 1018 can correspond to a measure of similarity between the third amino acid sequence 1012 and the amino acid sequences included in the training data 1016.

In various examples, the classification output 1018 can be provided to at least one of the light chain generating component 1002 or the heavy chain generating component 1006. The light chain generating component 1002 and/or the heavy chain generating component 1006 can utilize the classification output 1018 to modify one or more models implemented by the light chain generating component 1002 and/or the heavy chain generating component 1006. In this way, the one or more models implemented by the light chain generating component 1002 and/or the heavy chain generating component 1006 can be modified to generate amino acid sequences of antibody light chains and/or antibody heavy chains that correspond to the amino acid sequences included in the training data 1016.

In one or more scenarios, the framework 1000 can include one or more additional computation layers 1020. The additional computation layers 1020 can modify output from the concatenation component 1016 before the output from the concatenation component 1010 is provided to the challenging component 1014. In various examples, the additional computation layers 1020 can be a part of the concatenation component 1010. The additional computation layers 1020 can be utilized in situations where relationships between amino acid sequences and one or more biophysical properties are not accounted for by the concatenation component 1010. Additionally, the one or more additional computation layers 1020 can be utilized in situations where nonlinear relationships are present between the heavy chain amino acid sequences and the light chain amino acid sequences produced by the light chain generating component 1002 and the heavy chain generating component 1006. Further, the one or more additional computation layers 1020 can be utilized in scenarios where there are various interactions between the first amino acid sequence 1004 and the second amino acid sequence 1008 that can be captured by the one or more additional computation layers 1020.

FIGS. 11-14 illustrate example methods for generating amino acid sequences of proteins using machine learning techniques. The example processes are illustrated as collections of blocks in logical flow graphs, which represent sequences of operations that can be implemented in hardware, software, or a combination thereof. The blocks are referenced by numbers. In the context of software, the blocks represent computer-executable instructions stored on one or more computer-readable media that, when executed by one or more processing units (such as hardware microprocessors), perform the recited operations. Generally, computer-executable instructions include routines, programs, objects, components, data structures, and the like that perform particular functions or implement particular data types. The order in which the operations are described is not intended to be construed as a limitation, and any number of the described blocks can be combined in any order and/or in parallel to implement the process.

Figure 11:
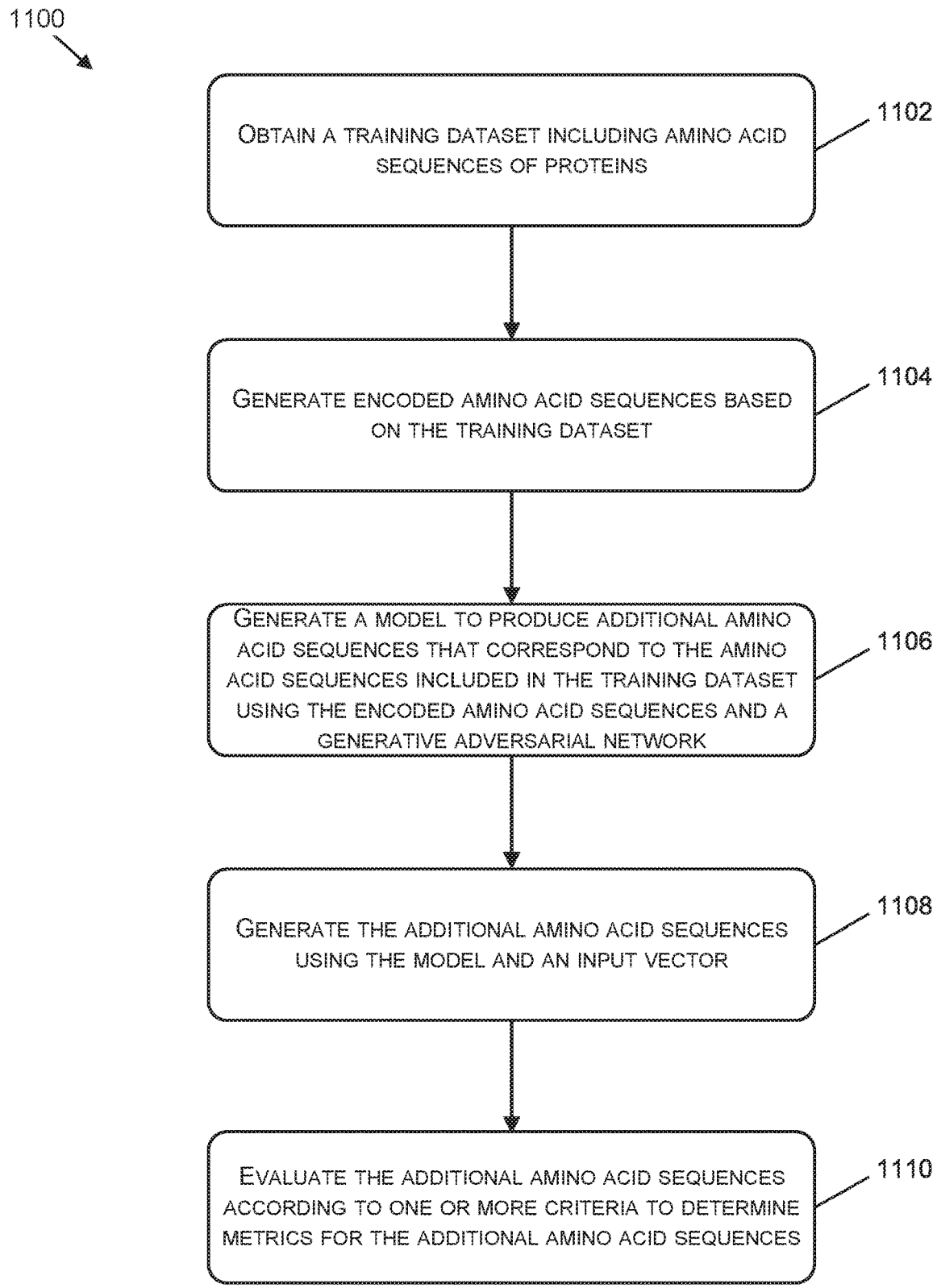
FIG. 11 is a flow diagram illustrating an example method for producing protein sequences, in accordance with some implementations.

FIG. 11 is a flow diagram illustrating another example method 1100 for producing protein sequences, in accordance with some implementations. At 1102, the method 1100 includes obtaining a training dataset that includes amino acid sequences of proteins. The training dataset can be obtained by extracting amino acid sequences of proteins from one or more databases. In various implementations, the amino acid sequences included in the training dataset can correspond to proteins that have one or more characteristics. For example, the amino acid sequences included in the training dataset can have one or more structural features. In additional examples, the amino acid sequences included in the training dataset can have one or more biophysical properties. In further examples, the amino acid sequences included in the training dataset can have one or more regions that include specified amino acid sequences.

At 1104, the method 1100 includes generating encoded amino acid sequences based on the training dataset. In various implementations, the encoded amino acid sequences can be produced by applying a classification system to the amino acid sequences included in the training dataset. In examples, the classification system can identify one or more regions of the amino acid sequences. Additionally, generating the encoded amino acid sequences can include generating a matrix for each amino acid sequence that indicates the amino acids included at the individual positions of the individual amino acid sequences.

At 1106, the method 1100 includes generating a model to produce additional amino acid sequences that correspond to the amino acid sequences included in the training set. The model can be generated using the encoded amino acid sequences produced from the training dataset. In addition, a generative adversarial network can be used to generate the model. In various implementations, the model can be used to produce amino acid sequences of proteins that have one or more characteristics that are the same as or similar to at least one characteristic of the proteins corresponding to the amino acid sequences included in the training dataset.

At 1108, the method 1100 can include generating the additional amino acid sequences using the model and an input vector. In examples, the input vector can include a series of random or pseudo-random numbers. Further, at 1110, the method 1100 can include evaluating the additional amino acid sequences according to one or more criteria to determine metrics for the additional amino acid sequences. The techniques and operations utilized to evaluate the additional amino acid sequences can be different from those utilized by the generative adversarial network to generate the model. In implementations, computer-readable instructions, such as those associated with a software tool or software platform, can be executed to evaluate the additional amino acid sequences. The additional amino acid sequences can be evaluated to determine whether proteins corresponding to the additional amino acid sequences have one or more specified characteristics. In particular implementations, the additional amino acid sequences can be evaluated to determine a number of variations of the individual additional amino acid sequences from amino acid sequences of proteins derived from germline genes.

Figure 12:
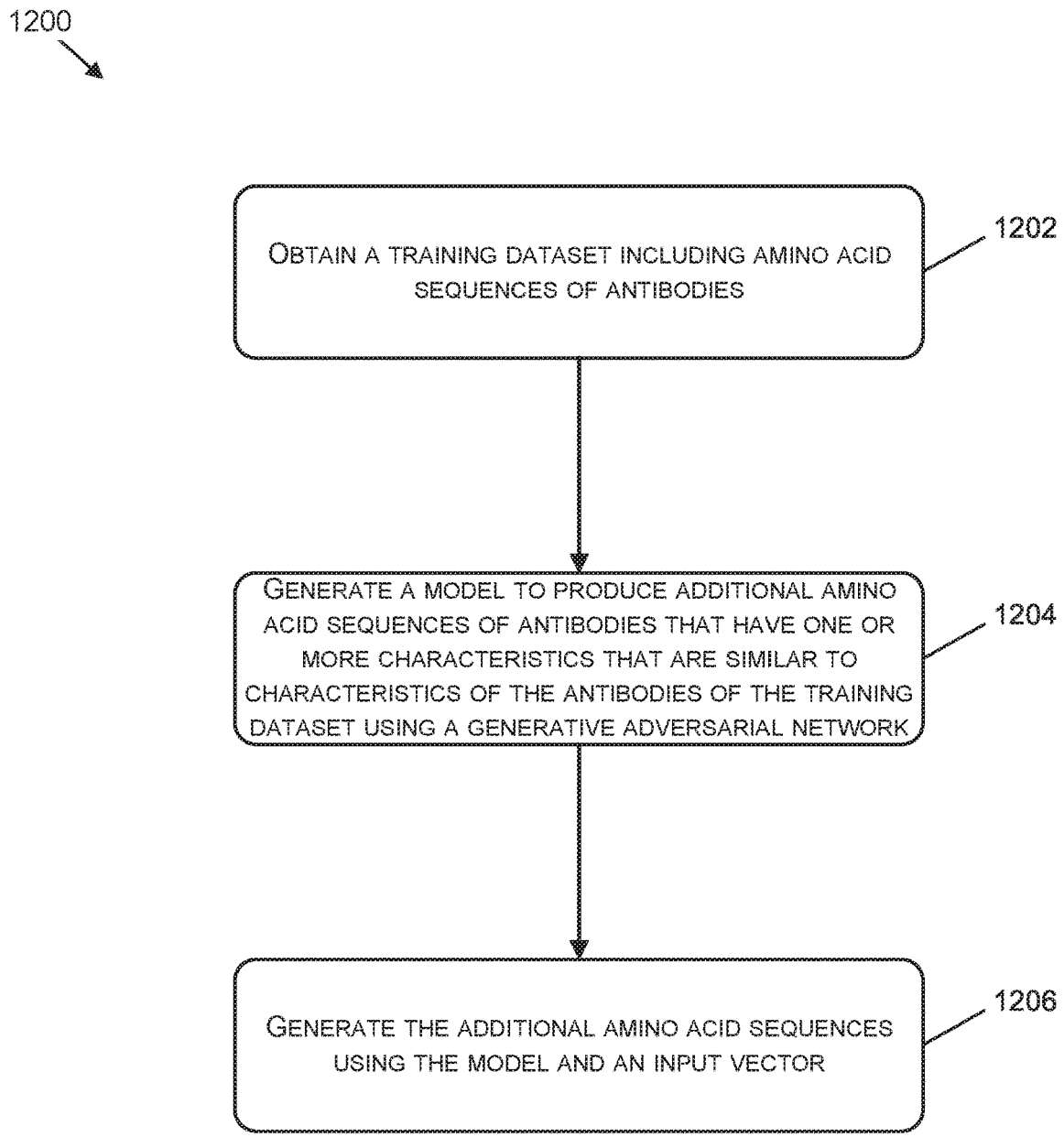
FIG. 12 is a flow diagram illustrating another example method for producing protein sequences, in accordance with some implementations.

FIG. 12 is a flow diagram illustrating another example method 1200 for producing antibody sequences, in accordance with some implementations. At 1202, the method 1200 includes obtaining a training dataset including amino acid sequences of antibodies. The amino acid sequences can be obtained from one or more databases that store amino acid sequences of antibodies.

At 1204, the method 1200 includes generating a model to produce additional amino acid sequences of antibodies that have one or more characteristics that are similar to characteristics of antibodies of the training dataset. The model can be produced using a generative adversarial network. In implementations, the additional amino acid sequences can correspond to antibodies having one or more specified structural features. Further, the additional amino acid sequences can correspond to antibodies having one or more biophysical features. In still additional examples, the additional amino acid sequences can correspond to amino acid sequences of antibodies derived from germline genes.

At 1206, the method 1200 can include generating the additional amino acid sequences using the model and an input vector. In various scenarios, the input vector can include a random or pseudo-random series of numbers having a specified length. The model can obtain the input vector and use the input vector to produce output that corresponds to amino acid sequences of antibodies.

Figure 13:
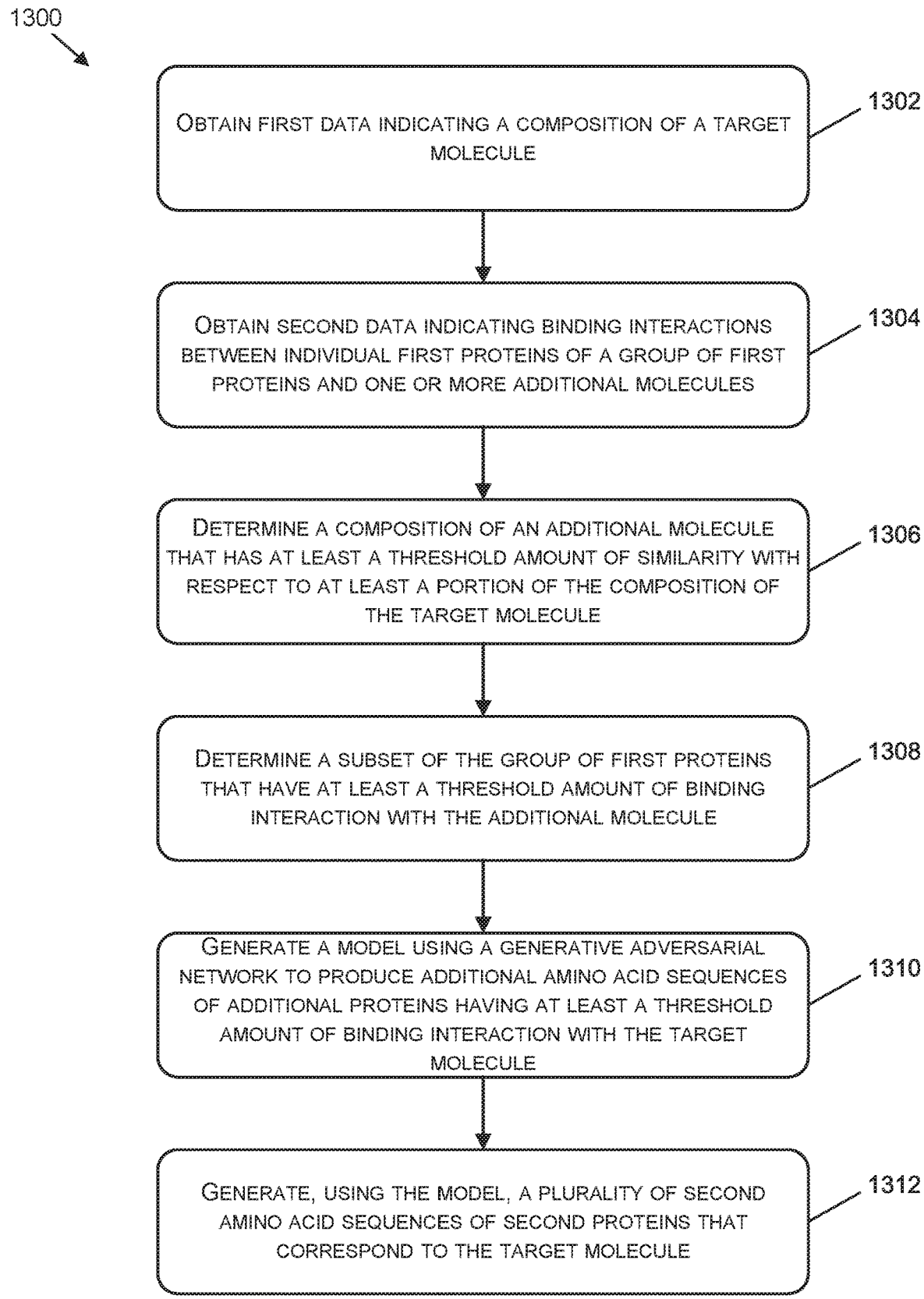
FIG. 13 is a flow diagram illustrating an example method to produce amino acid sequences of proteins that bind to a specified target molecule, in accordance with some implementations.

FIG. 13 is a flow diagram illustrating an example method 1300 to produce amino acid sequences of proteins that bind to a specified target molecule, in accordance with some implementations. The method 1300 can include, at operation 1302, obtaining first data indicating a composition of a target molecule. The target molecule can correspond to a protein for which proteins that bind to the target molecule are being generated. The composition of the target molecule can correspond to an arrangement of atoms that comprise the target molecule. In various examples, the composition of the target molecule can include an arrangement of sub-groups of atoms that comprise the target molecule. For example, the target molecule can comprise a protein and the composition of the target molecule can be comprised of a sequence of amino acids. In illustrative examples, the target molecule can include an antigen and the method 1300 can be directed to generating amino acid sequences of antibodies that bind to the antigen. In additional illustrative examples, the target molecule can include a substrate and the method 1300 can be directed to generating amino acid sequences of enzymes that bind to the substrate.

In addition, at 1304, the method 1300 can include obtaining second data indicating binding interactions between individual first proteins of a group of first proteins and one or more additional molecules. The second data can include data that has been derived experimentally and indicates binding between the first proteins and the one or more additional molecules. In various examples, the second data can be simulated and derived computationally to indicate binding between the first proteins and the one or more additional molecules. The binding interactions can include at least one of a binding affinity or a binding avidity. In various examples, the binding interactions can indicate a sequence of amino acids included in a binding region of an antibody and an additional amino acid sequence of an epitope region of an antigen, where the binding region has at least a threshold amount of binding interaction with the epitope region. Additionally, the binding interactions can indicate couplings between amino acids included in the binding region and additional amino acids located in the epitope region. In illustrative examples, the second data can include equilibrium constants between individual proteins and one or more additional molecules. To illustrate, the second data can include equilibrium dissociation constants between individual first proteins and the one or more additional molecules. The second data can indicate that an individual first protein can bind to a single additional molecule. The second data can also indicate that an individual first protein can bind to multiple additional molecules. Further, the second data can indicate that multiple first proteins can bind to a single additional molecule.

In various implementations, the second data can indicate the portions of the first proteins and the portions of the additional molecules where the binding takes place. For example, the second data can indicate the atoms of the first proteins that participate in binding interactions with atoms of the additional molecules. In situations where the additional molecules comprise proteins, the second data can indicate the amino acids of the first proteins and the amino acids of the additional molecules that participate in binding interactions. Further, in additional implementations, the first proteins can comprise antibodies and the additional molecules can comprise antigens. In these scenarios, the second data can indicate the amino acids included in one or more binding regions of individual first proteins and the amino acids included in one or more epitope regions of individual antigens.

The second data can also indicate structural features of the first proteins and the additional molecules that participate in binding interactions. To illustrate, the second data can indicate functional groups of the first proteins and functional groups of additional molecules that participate in binding interactions. Additionally, in situations where the additional molecules include proteins, the second data can indicate at least one of secondary structures or tertiary structures of the first proteins and the additional molecules that participate in binding interactions. In illustrative examples, the second data can indicate structures that are part of binding interactions, such as sheets, helices, bends, coils, turns, bridges, loops, or one or more combinations thereof.

Further, at 1306, the method 1300 can include determining a composition of an additional molecule that has at least a threshold amount of similarity with respect to at least a portion of the composition of the target molecule. An amount of similarity between the target and an additional molecule can be determined by determining a number of one or more atoms included in the target molecule and the additional molecule and comparing the number of atoms. For example, the number of carbon atoms included in the target molecule and the number of carbon atoms included in the additional molecule can be determined can compared with each other. Continuing with this example, the amount of difference between the number of carbon atoms included in the target molecule and the number of carbon atoms in the additional molecule can correspond to an amount of similarity between the target molecule and the additional molecule.

Additionally, the amount of similarity between the target molecule and the additional molecule can be determined by determining functional groups of the target molecule and the additional molecule and comparing the number and/or location of one or more types of functional groups included in the target molecule and the additional molecule. In these situations, an amount of similarity between the target molecule and the additional molecule can be based on differences between the number of one or more functional groups of the additional molecule and the target molecule. For example, an amount of similarity between the target molecule and the additional molecule can be based on a difference between a number of aldehyde groups included in the target molecule and a number of aldehyde groups included in the additional molecule. In another example, a number of aromatic groups included in the target molecule and a number of aromatic groups included in the additional molecule can be used to determine an amount of similarity between the target molecule and the additional molecule. Differences and/or similarities between locations of functional groups can also be used to determine an amount of similarity between the target molecule and the additional molecule. To illustrate, carboxyl groups located at carbon positions 2 and 10 of the target molecule can be compared with the locations of carboxyl groups of the additional molecule. Continuing with this example, an amount of similarity between the target molecule and the additional molecule can be based on whether or not the carboxyl groups of the additional molecule are also located at positions 2 and 10.

In scenarios where the target molecule and the additional molecule are proteins, an amount of similarity between the target molecule and the additional molecule can be determined by comparing amino acids at individual positions of the amino acid sequence of the target molecule and the amino acid sequence of the additional molecule. In implementations, individual amino acids located at each position of the amino acid sequence of the target molecule can be compared with individual amino acids at each position of the amino acid sequence of the additional molecule. In additional implementations, individual amino acids located at positions of one or more regions of the target molecule can be compared with individual amino acids located at positions of one or more regions of the additional molecule that correspond to the one or more regions of the target molecule. For example, amino acids located in an epitope region of the target molecule can be compared with amino acids located in one or more regions of the additional molecule that can correspond to the epitope region. The number of positions of at least a portion of the amino acid sequence of the target molecule that have amino acids that are the same as at least a corresponding portion of the amino acid sequence of the additional molecule can correspond to an amount of identity between the target molecule and the additional molecule. In these situations, the amount of similarity between the additional molecule and the target molecule can correspond to an amount of identity between the amino acid sequences of one or more portions of the additional molecule and the target molecule.

Although the amount of similarity between the target molecule and the additional molecule have been described with respect to various examples, the amount of similarity between the target molecule and the additional molecule can be determined based on one or more combinations of a number of criteria. For example, an amount of similarity between the target molecule and the additional molecule can be determined by analyzing at least one of a number of one or more atoms included in the target molecule and the additional molecule, a number of bonding arrangements (e.g., single bonds, double bonds, triple bonds) included in the target molecule and the additional molecule, a number of one or more functional groups included in the target molecule and the additional molecule, locations of secondary structural features of the target molecule and the additional molecule, amino acids included in secondary structural features of the target molecule and the additional molecule, tertiary structure of the target molecule and the additional molecule, or identity with respect to one or more regions of the target molecule and the additional molecule.

Threshold amounts of similarity between the additional molecule and the target molecule can be based on a likelihood that a protein that binds to the target molecule also binds to the additional molecule. In implementations where the target molecule and the additional molecule are antigens, a threshold amount of similarity can correspond to a minimum amount of identity between one or more regions of the target molecule and one or more regions of the additional molecule. In illustrative examples, a threshold amount of similarity between the target molecule and the additional molecule can correspond to a minimum amount of identity between an epitope region of the target molecule with respect to one or more regions of the additional molecule.

At 1308, the method 1300 can include determining a subset of the group of first proteins that have at least a threshold amount of binding interaction with the additional molecule. The threshold amount of binding interaction can correspond to a maximum value of an equilibrium dissociation constant. In these situations, determining the subset of the group of first proteins can include determining an equilibrium dissociation constant between individual first proteins and the additional molecule. The equilibrium dissociation constants can then be compared against the threshold equilibrium dissociation constant. In situations where an equilibrium dissociation constant is less than the threshold equilibrium dissociation constant, the corresponding first protein can be added to the subset of the group of first proteins.

Additionally, at 1310, the method 1300 can include generating a model using a generative adversarial network to produce additional amino acid sequences of additional proteins having at least a threshold amount of binding interaction with the target molecule. The generative adversarial network can include a generating component that produces amino acid sequences of antibodies based on an antigen sequence. The generating component can use an input vector that includes noise data produced by a random number generator or a pseudo-random number generator to produce the amino acid sequences. The amino acid sequences produced by the generating component can be evaluated by a challenging component of the generative adversarial network. The challenging component can be a discriminator. The challenging component can evaluate the amino acid sequences produced by the generating component with respect to antibody amino acid sequences that have at least a threshold amount of binding to antigens that have at least a threshold amount of similarity with respect to a target antigen. For example, the challenging component can analyze the amino acid sequence produced by the generating component with respect to the amino acid sequences of subset of the group of first proteins having at least a threshold amount of binding interaction with the additional molecule determined at operation 1308. The model can include one or more functions having one or more variables with individual variables having respective weights.

The process 1300 can also include, at 1312, generating, using the model, a plurality of second amino acid sequences of second proteins that correspond to the target molecule. For example, the target molecule can include an antigen and the model can be used to generate amino acid sequences of antibodies that have at least a threshold probability of having at least a threshold binding interaction with respect to the antigen. In illustrative examples, the model can be used to generate amino acid sequences of antibodies that have at least a threshold equilibrium dissociation constant in relation to the antigen.

Figure 14:
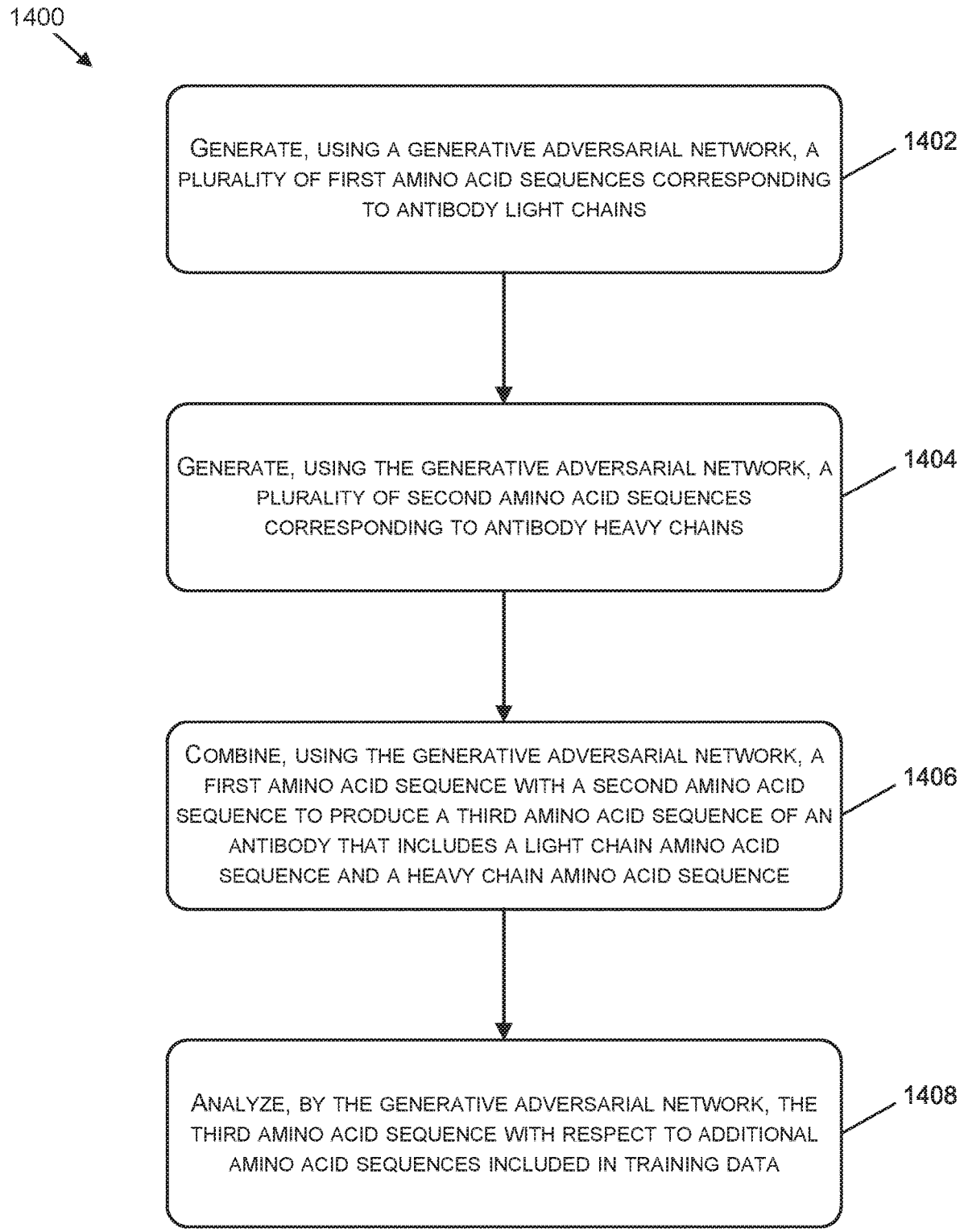
FIG. 14 is a flow diagram illustrating an example method to produce amino acid sequences of antibodies by combining amino acid sequences of antibody heavy chains and amino acid sequences of light chains, in accordance with some implementations.

FIG. 14 is a flow diagram illustrating an example method 1400 to produce amino acid sequences of antibodies by combining separately generated amino acid sequences of antibody heavy chains and light chains, in accordance with some implementations. The method 1400 can include, at 1402, generating, using a generative adversarial network, first data corresponding to a plurality of first amino acid sequences related to antibody light chains. The generative adversarial network can include a first generating component that implements a first model to generate the plurality of first amino acid sequences. The first model can include a first function having one or more first variables and one or more first weights. The antibody light chains can include at least one of variable regions or constant regions of light chains of antibodies. In addition, the antibody light chains can include complentarity-determining regions (CDRs) of light chains of antibodies. The generative adversarial network can use input data to generate the plurality of first amino acid sequences. The input data can include a numerical string produced by a random number generator or a pseudo-random number generator.

At 1404, the method 1400 can include generating, using the generative adversarial network, a plurality of second amino acid sequences corresponding to antibody heavy chains. The generative adversarial network can also include a second generating component that implements a second model to generate the plurality of second amino acid sequences. The second model can include a second function that is different from the first function. The second function can include one or more second variables and one or more second weights. The antibody heavy chains can include at least one of variable regions or constant regions of heavy chains of antibodies. The antibody heavy chains can also include CDRs of heavy chains of antibodies. The generative adversarial network can use additional input data to generate the plurality of second amino acid sequences. The additional input data can include a numerical string produced by a random number generator or a pseudo-random number generator.

At 1406, the method 1400 can include combining, using the generative adversarial network, a first amino acid sequence with a second amino acid sequence to produce a third amino acid sequence of an antibody that includes a light chain amino acid sequence and a heavy chain amino acid sequence. The first amino acid sequence can be combined with the second amino acid sequence by concatenating the second amino acid sequence to the first amino acid sequence. In one or more examples, the first amino acid sequence, the second amino acid sequence, and the third amino acid sequence can be encoded according to a classification system.

At 1408, the method 1400 can include analyzing, by the generative adversarial network, the third amino acid sequence with respect to additional amino acid sequences included in training data. The third amino acid sequence can be analyzed by a discriminator and the output can be provided to at least one of the first generating component or the second generating component. For example, based on the output by the discriminator, the first generating component can modify the first model used to generate the first amino acid sequence. In addition, based on the output by the discriminator, the second generating component can modify the second model used to generate the second amino acid sequence. In this way, the output from the discriminator can be used as feedback by at least one of the first generating component or the second generating component to generate amino acid sequences that are more likely to correspond to the additional amino acid sequences included in the training data.

The output produced by the discriminator over time can be indicative of an amount of progress in the training of the first model and in the training of the second model. After the training of the first model is complete, a first trained model can be used to generate amino acid sequences of antibody light chains and after the training of the second model is complete, a second trained model can be used to generate amino acid sequences of antibody heavy chains. The amino acid sequences produced by the first trained model and the second trained model can be combined and the combined amino acid sequences can be analyzed by a software tool. The software tool can determine one or more metrics with respect to the combined amino acid sequences. To illustrate, the one or more metrics can include at least one of a number of hydrophobic amino acids, a number of positively charged amino acids, a number of negatively charged amino acids, a number of uncharged amino acids, a level of expression, a melting temperature, or a level of self-aggregation.

In addition, the first trained model and the second trained model can undergo further training using additional training data that is different from the initial training data used to produce the first trained model and the second trained model. For example, the additional training data can include amino acid sequences of antibodies having one or more characteristics. To illustrate, the additional training data can include amino acid sequences of antibodies having negatively charged regions, hydrophobic regions, a relatively low probability of aggregation, a specified percentage of high molecular weight (HMW), melting temperature, a threshold level of expression, or one or more combinations thereof. In these implementations, the output from a discriminator of the generative adversarial network that is based on the additional training data can be used to further modify the models implemented by the first generating component and the second generating component such that the amino acid sequences produced by the generative adversarial network can correspond to the amino acid sequences of antibodies included in the additional training data.

Figure 15:
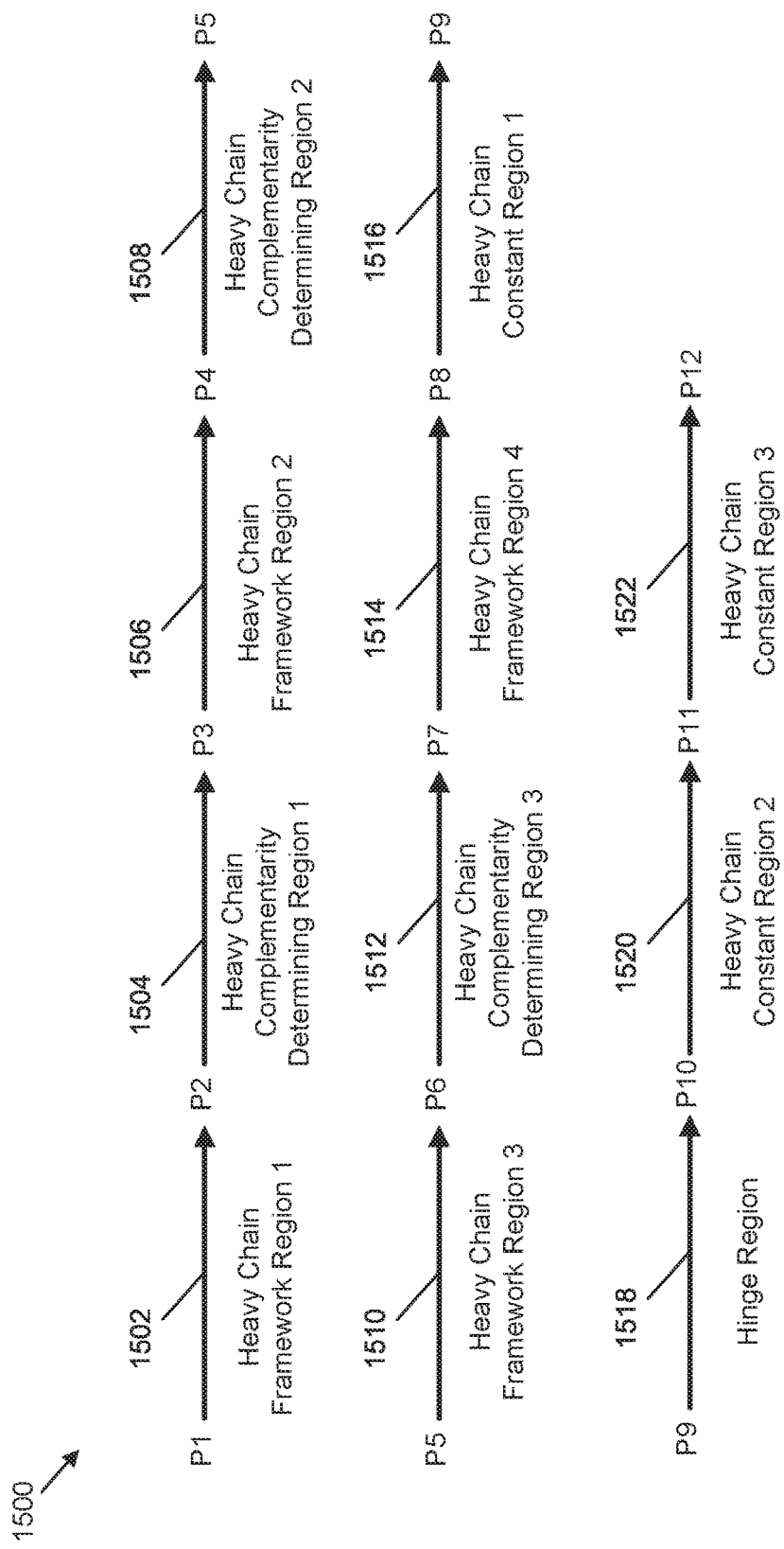
FIG. 15 is an example of a scheme to structurally align amino acid sequences of antibodies before encoding the amino acid sequences of the antibodies for input to a generative adversarial network, in accordance with some implementations.

FIG. 15 is an example of a scheme to structurally align amino acid sequences of antibodies for input to a generative machine learning architecture, in accordance with some implementations. The structure of FIG. 15 corresponds to the application of a classification system to a heavy chain domain of an antibody. In one or more illustrative examples, the classification system can allocate 149 positions to encode the variable region of the heavy chain of an antibody. Additionally, the classification system used to produce the structure 1500 in the illustrative example of FIG. 15 can allocate 123 positions to encode the constant regions of the heavy chain of the antibody. Further, the classification system used to produce the structure 1500 in the illustrative example of FIG. 15 can allocate 123 positions to encode a hinge region of the heavy chain of the antibody.

Amino acids that are associated with individual positions of the amino acid sequence may be represented by letters in the structure 1500. Additionally, positions that are not associated with any amino acid may be represented in the structure 1500. Gaps in the amino acid sequence related to the structure 1500 can indicate structure of the antibody that corresponds to the structure shown in FIG. 15.

In the illustrative example of FIG. 15, the structure 1500 can include a first region 1702 from a first position to a second position that includes amino acids of a first heavy chain framework region and a second region 1704 from the second position to the third position that includes amino acids of a first heavy chain CDR. In addition, the structure 1500 can include a third region 1706 from the third position to a fourth position that includes amino acids of a second heavy chain framework region and a fourth region 1708 from the fourth position to a fifth position that includes amino acids of a second heavy chain CDR. Further, the structure 1500 can include a fifth region 1710 from the fifth position to a sixth position that includes amino acids of a third heavy chain framework region and a sixth region 1712 from the sixth position to a seventh position that includes amino acids of a third CDR. The structure 1500 can also include a seventh region 1714 from the seventh position to an eighth position that includes amino acids of a fourth heavy chain framework region and an eighth region 1716 from the eighth position to a ninth position that includes amino acids of a first heavy chain constant region. Additionally, the structure 1500 may include a ninth region 1718 from the ninth position to a tenth position that includes a hinge region of the heavy chain of the antibody. In various examples, the structure 1500 may include a tenth region 1720 from the tenth position to an eleventh position that includes a second heavy chain constant region and an eleventh region 1722 from the eleventh position to a twelfth position that includes amino acids of a third heavy chain constant region. Each region of the structure may include a predetermined number of locations and at least a portion of the locations may be associated with a particular amino acid.

Figure 16:
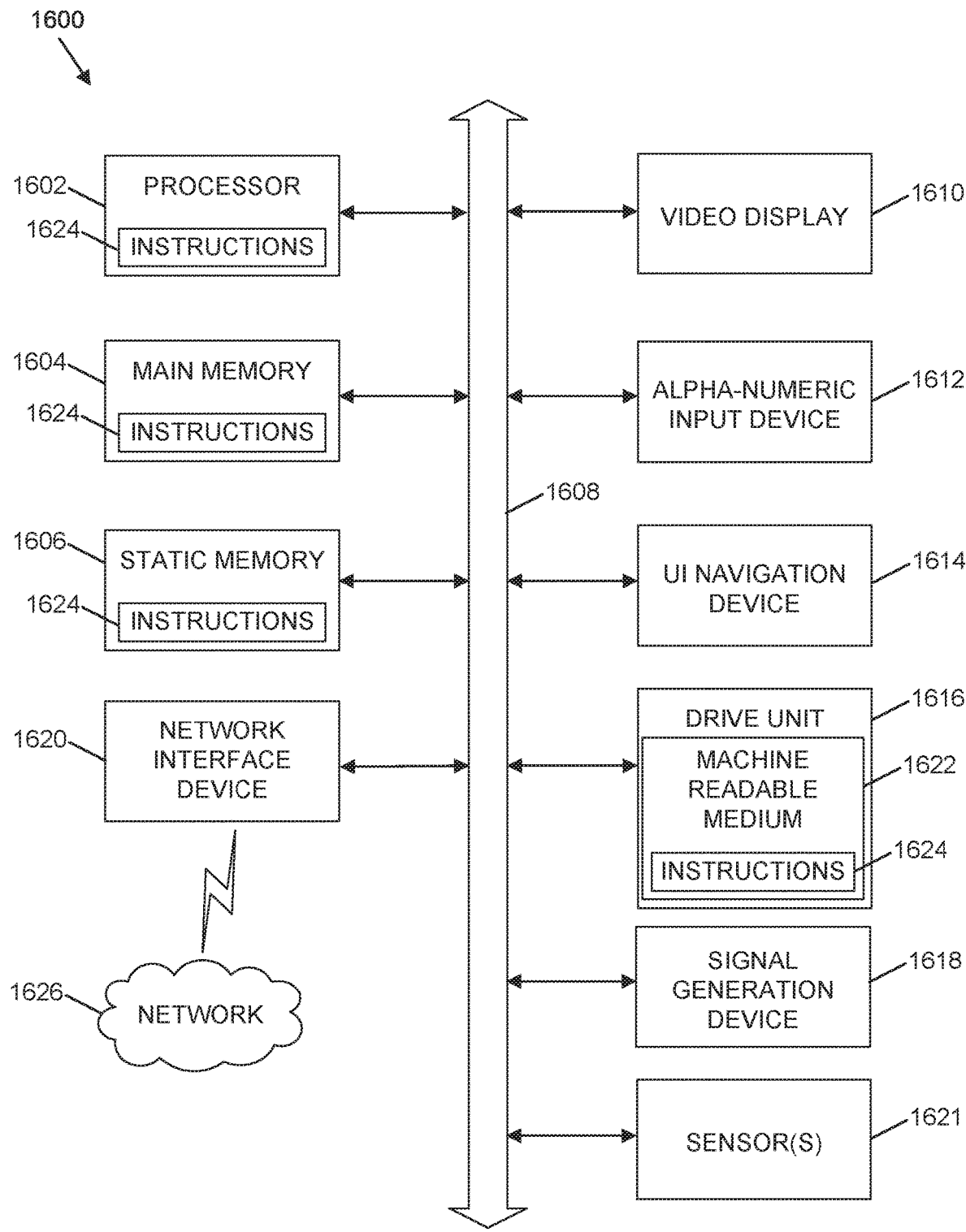
FIG. 16 illustrates a diagrammatic representation of a machine in the form of a computer system within which a set of instructions may be executed for causing the machine to perform any one or more of the methodologies discussed herein, according to an example embodiment.

FIG. 16 illustrates a diagrammatic representation of a machine 1600 in the form of a computer system within which a set of instructions may be executed for causing the machine 1600 to perform any one or more of the methodologies discussed herein, according to an example, according to an example embodiment. Specifically, FIG. 16 shows a diagrammatic representation of the machine 1600 in the example form of a computer system, within which instructions 1624 (e.g., software, a program, an application, an applet, an app, or other executable code) for causing the machine 1600 to perform any one or more of the methodologies discussed herein may be executed. For example, the instructions 1624 may cause the machine 1600 to implement the frameworks 100, 200, 300, 400, 500, 600, 700, 800 described with respect to FIGS. 1, 2, 3, 4, 5, 6, 7, 8, 9, and 10 respectively, and to execute the methods 1100, 1200, 1300, 1400 described with respect to FIGS. 11, 12, 13, and 14 respectively. Additionally, the encoding shown in FIG. 15 can be generated using the machine 1600 using instructions 1824.

The instructions 1824 transform the general, non-programmed machine 1600 into a particular machine 1600 programmed to carry out the described and illustrated functions in the manner described. In alternative embodiments, the machine 1600 operates as a standalone device or may be coupled (e.g., networked) to other machines. In a networked deployment, the machine 1600 may operate in the capacity of a server machine or a client machine in a server-client network environment, or as a peer machine in a peer-to-peer (or distributed) network environment. The machine 1600 may comprise, but not be limited to, a server computer, a client computer, a personal computer (PC), a tablet computer, a laptop computer, a netbook, a set-top box (STB), a personal digital assistant (PDA), an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 1624, sequentially or otherwise, that specify actions to be taken by the machine 1600. Further, while only a single machine 1600 is illustrated, the term "machine" shall also be taken to include a collection of machines 1600 that individually or jointly execute the instructions 1016 to perform any one or more of the methodologies discussed herein.

Examples of computing device 1600 can include logic, one or more components, circuits (e.g., modules), or mechanisms. Circuits are tangible entities configured to perform certain operations. In an example, circuits can be arranged (e.g., internally or with respect to external entities such as other circuits) in a specified manner. In an example, one or more computer systems (e.g., a standalone, client or server computer system) or one or more hardware processors (processors) can be configured by software (e.g., instructions, an application portion, or an application) as a circuit that operates to perform certain operations as described herein. In an example, the software can reside (1) on a non-transitory machine readable medium or (2) in a transmission signal. In an example, the software, when executed by the underlying hardware of the circuit, causes the circuit to perform the certain operations.

In an example, a circuit can be implemented mechanically or electronically. For example, a circuit can comprise dedicated circuitry or logic that is specifically configured to perform one or more techniques such as discussed above, such as including a special-purpose processor, a field programmable gate array (FPGA) or an application-specific integrated circuit (ASIC). In an example, a circuit can comprise programmable logic (e.g., circuitry, as encompassed within a general-purpose processor or other programmable processor) that can be temporarily configured (e.g., by software) to perform the certain operations. It will be appreciated that the decision to implement a circuit mechanically (e.g., in dedicated and permanently configured circuitry), or in temporarily configured circuitry (e.g., configured by software) can be driven by cost and time considerations.

Accordingly, the term "circuit" is understood to encompass a tangible entity, be that an entity that is physically constructed, permanently configured (e.g., hardwired), or temporarily (e.g., transitorily) configured (e.g., programmed) to operate in a specified manner or to perform specified operations. In an example, given a plurality of temporarily configured circuits, each of the circuits need not be configured or instantiated at any one instance in time. For example, where the circuits comprise a general-purpose processor configured via software, the general-purpose processor can be configured as respective different circuits at different times. Software can accordingly configure a processor, for example, to constitute a particular circuit at one instance of time and to constitute a different circuit at a different instance of time.

In an example, circuits can provide information to, and receive information from, other circuits. In this example, the circuits can be regarded as being communicatively coupled to one or more other circuits. Where multiple of such circuits exist contemporaneously, communications can be achieved through signal transmission (e.g., over appropriate circuits and buses) that connect the circuits. In embodiments in which multiple circuits are configured or instantiated at different times, communications between such circuits can be achieved, for example, through the storage and retrieval of information in memory structures to which the multiple circuits have access. For example, one circuit can perform an operation and store the output of that operation in a memory device to which it is communicatively coupled. A further circuit can then, at a later time, access the memory device to retrieve and process the stored output. In an example, circuits can be configured to initiate or receive communications with input or output devices and can operate on a resource (e.g., a collection of information).

The various operations of method examples described herein can be performed, at least partially, by one or more processors that are temporarily configured (e.g., by software) or permanently configured to perform the relevant operations. Whether temporarily or permanently configured, such processors can constitute processor-implemented circuits that operate to perform one or more operations or functions. In an example, the circuits referred to herein can comprise processor-implemented circuits.

Similarly, the methods described herein can be at least partially processor-implemented. For example, at least some of the operations of a method can be performed by one or processors or processor-implemented circuits. The performance of certain of the operations can be distributed among the one or more processors, not only residing within a single machine, but deployed across a number of machines. In an example, the processor or processors can be located in a single location (e.g., within a home environment, an office environment or as a server farm), while in other examples the processors can be distributed across a number of locations.

The one or more processors can also operate to support performance of the relevant operations in a "cloud computing" environment or as a "software as a service" (SaaS). For example, at least some of the operations can be performed by a group of computers (as examples of machines including processors), with these operations being accessible via a network (e.g., the Internet) and via one or more appropriate interfaces (e.g., Application Program Interfaces (APIs).)

Example embodiments (e.g., apparatus, systems, or methods) can be implemented in digital electronic circuitry, in computer hardware, in firmware, in software, or in any combination thereof. Example embodiments can be implemented using a computer program product (e.g., a computer program, tangibly embodied in an information carrier or in a machine readable medium, for execution by, or to control the operation of, data processing apparatus such as a programmable processor, a computer, or multiple computers).

A computer program can be written in any form of programming language, including compiled or interpreted languages, and it can be deployed in any form, including as a stand-alone program or as a software module, subroutine, or other unit suitable for use in a computing environment. A computer program can be deployed to be executed on one computer or on multiple computers at one site or distributed across multiple sites and interconnected by a communication network.

In an example, operations can be performed by one or more programmable processors executing a computer program to perform functions by operating on input data and generating output. Examples of method operations can also be performed by, and example apparatus can be implemented as, special purpose logic circuitry (e.g., a field programmable gate array (FPGA) or an application-specific integrated circuit (ASIC)).

The computing system can include clients and servers. A client and server are generally remote from each other and generally interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware can be a design choice. Below are set out hardware (e.g., computing device 1600) and software architectures that can be deployed in example embodiments.

In an example, the computing device 1600 can operate as a standalone device or the computing device 1600 can be connected (e.g., networked) to other machines.

In a networked deployment, the computing device 1600 can operate in the capacity of either a server or a client machine in server-client network environments. In an example, computing device 1600 can act as a peer machine in peer-to-peer (or other distributed) network environments. The computing device 1600 can be a personal computer (PC), a tablet PC, a set-top box (STB), a Personal Digital Assistant (PDA), a mobile telephone, a web appliance, a network router, switch or bridge, or any machine capable of executing instructions (sequential or otherwise) specifying actions to be taken (e.g., performed) by the computing device 1600. Further, while only a single computing device 1600 is illustrated, the term "computing device" shall also be taken to include any collection of machines that individually or jointly execute a set (or multiple sets) of instructions to perform any one or more of the methodologies discussed herein.

Example computing device 1600 can include a processor 1602 (e.g., a central processing unit CPU), a graphics processing unit (GPU) or both), a main memory 1804 and a static memory 1806, some or all of which can communicate with each other via a bus 1608. The computing device 1600 can further include a display unit 1610, an alphanumeric input device 1612 (e.g., a keyboard), and a user interface (UI) navigation device 1814 (e.g., a mouse). In an example, the display unit 1610, input device 1612 and UI navigation device 1814 can be a touch screen display. The computing device 1600 can additionally include a storage device (e.g., drive unit) 1616, a signal generation device 1618 (e.g., a speaker), a network interface device 1620, and one or more sensors 1621, such as a global positioning system (GPS) sensor, compass, accelerometer, or other sensor.

The storage device 1616 can include a machine readable medium 1622 on which is stored one or more sets of data structures or instructions 1624 (e.g., software) embodying or utilized by any one or more of the methodologies or functions described herein. The instructions 1624 can also reside, completely or at least partially, within the main memory 1604, within static memory 1606, or within the processor 1602 during execution thereof by the computing device 1600. In an example, one or any combination of the processor 1602, the main memory 1604, the static memory 1606, or the storage device 1616 can constitute machine readable media.

While the machine readable medium 1622 is illustrated as a single medium, the term "machine readable medium" can include a single medium or multiple media (e.g., a centralized or distributed database, and/or associated caches and servers) that configured to store the one or more instructions 1624. The term "machine readable medium" can also be taken to include any tangible medium that is capable of storing, encoding, or carrying instructions for execution by the machine and that cause the machine to perform any one or more of the methodologies of the present disclosure or that is capable of storing, encoding or carrying data structures utilized by or associated with such instructions. The term "machine readable medium" can accordingly be taken to include, but not be limited to, solid-state memories, and optical and magnetic media. Specific examples of machine-readable media can include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 1624 can further be transmitted or received over a communications network 1626 using a transmission medium via the network interface device 1820 utilizing any one of a number of transfer protocols (e.g., frame relay, IP, TCP, UDP, HTTP, etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., IEEE 802.11 standards family known as Wi-Fi®, IEEE 802.16 standards family known as WiMax®), peer-to-peer (P2P) networks, among others. The term "transmission medium" shall be taken to include any intangible medium that is capable of storing, encoding or carrying instructions for execution by the machine, and includes digital or analog communications signals or other intangible medium to facilitate communication of such software.

Example Implementations

1. A method comprising: obtaining, by a computing system including one or more computing devices having one or more processors and memory, first data indicating a first amino acid sequence of a first antigen; obtaining, by the computing system, second data indicating binding interactions between individual antibodies of a first plurality of antibodies and one or more antigens; determining, by the computing system, a second amino acid sequence of a second antigen of the one or more antigens that has at least a threshold amount of identity with respect to at least a portion of the first amino acid sequence of the first antigen; determining, by the computing system and based on the second data, a group of the first plurality of antibodies included in the second data that have at least a first threshold amount of binding interaction with the second antigen; generating, by the computing system and using a generative adversarial network, a model to produce additional amino acid sequences of additional antibodies having at least a threshold probability of having at least a second threshold amount of binding interaction with the first antigen, wherein the model is generated based on the first amino acid sequence of the first antigen and the group of the first plurality of antibodies; and generating, by the computing system, and using the model, a second plurality of amino acid sequences of antibodies that correspond to the first antigen.

2. The method of 1, wherein the binding interactions include at least one of a binding affinity or a binding avidity.

3. The method of 1 or 2, wherein: the binding interactions indicate an amino acid sequence of a binding region of an antibody of the first plurality of antibodies and an additional amino acid sequence of an epitope region of an antigen of the one or more antigens, and the binding region binds to the epitope region.

4. The method of 3, wherein the binding interactions indicate couplings between amino acids included in the binding region and additional amino acids included in the epitope region.

5. The method of any one of 1-4, wherein the binding interactions include equilibrium constants between the individual antibodies of a first plurality of antibodies and the one or more antigens.

6. The method of any one of 1-5, further comprising evaluating, by the computing system and using a software tool, one or more metrics with respect to the second plurality of amino acid sequences of antibodies, the one or more metrics including at least one of a number of hydrophobic amino acids included in individual amino acid sequences of the second plurality of amino acid sequences, a number of positively charged amino acids included in individual amino acid sequences of the second plurality of amino acid sequences, a number of negatively charged amino acids included in individual amino acid sequences of the second plurality of amino acid sequences, a number of uncharged amino acids included in individual amino acid sequences of the second plurality of amino acid sequences, a level of expression of individual antibodies, a melting temperature of individual antibodies, or a level of self-aggregation of individual antibodies.

7. A method comprising: obtaining, by a computing system including one or more computing devices having one or more processors and memory, first data indicating a composition of a target molecule; obtaining, by the computing system, second data indicating binding interactions between individual first proteins of a plurality of first proteins and one or more additional molecules; determining, by the computing system, a composition of an additional molecule of the one or more additional molecules that has at least a threshold amount of similarity with respect to at least a portion of the composition of the target molecule; determining, by the computing system and based on the second data, a group of the plurality of first proteins included in the second data that have at least a first threshold amount of binding interaction with the additional molecule; generating, by the computing system and using a generative adversarial network, a model to produce additional amino acid sequences of additional proteins having at least a threshold probability of having at least a second threshold amount of binding interaction with the target molecule, wherein the model is generated based on the composition of the target molecule and the group of the plurality of first proteins; and generating, by the computing system, and using the model, a plurality of second amino acid sequences of second proteins that correspond to the target molecule.

8. The method of 7, wherein the target molecule includes a protein.

9. The method of 8, wherein the protein includes an antigen, the plurality of first proteins include first antibodies, and the plurality of second proteins include second antibodies.

10. A method comprising: generating, by a computing system including one or more computing devices having one or more processors and memory and using a generative adversarial network, a plurality of first amino acid sequences, individual first amino acid sequences of the plurality of first amino acid sequences corresponding to antibody light chains; generating, by the computing system and using the generative adversarial network, a plurality of second amino acid sequences, individual second amino acid sequences of the plurality of second amino acid sequences corresponding to antibody heavy chains; combining, by the computing system and using the generative adversarial network, a first amino acid sequence of the plurality of first amino acid sequences with a second amino acid sequence of the plurality of second amino acid sequences to produce a third amino acid sequence, the third amino acid sequence corresponding to an antibody including a light chain corresponding to the first amino acid sequence and a heavy chain corresponding to the second amino acid sequence; and analyzing, by the computing system and using the generative adversarial network, the third amino acid sequence with respect to an additional plurality of amino acid sequences to produce an output, the additional plurality of amino acid sequences being included in training data for the generative adversarial network and the output indicating a measure of similarity between the third amino acid sequence and at least a portion of the additional plurality of amino acid sequences.

11. The method of 10, wherein combining the first amino acid sequence with the second amino acid sequence includes concatenating the second amino acid sequence to the first amino acid sequence.

12. The method of 10 or 11, wherein: the generative adversarial network includes a first generating component that implements a first model to generate the plurality of first amino acid sequences and a second generating component that implements a second model to generate the plurality of second amino acid sequences; the first model includes a first function having one or more first variables and one or more first weights; and the second model includes a second function different from the first function, the second function including one or more second variables and one or more second weights.

13. The method of 12, wherein the third amino acid sequence is analyzed by a discriminator and the output is provided to at least one of the first generating component or the second generating component.

14. The method of 13, wherein the first generating component modifies the first model based on the output.

15. The method of 13, wherein the second generating component modifies the second model based on the output.

16. The method of any one of 10-15, wherein the first amino sequence includes at least a portion of a first variable region of an antibody light chain and the second amino acid sequence includes at least a portion of a first variable region of an antibody heavy chain.

17. The method of any one of 10-16, wherein the first amino acid sequence includes at least a portion of a first variable region and a first constant region of an antibody light chain and the second amino acid sequence includes at least a portion of a second variable region and a second constant region of an antibody heavy chain.

18. The method of any one of 10-17, comprising: determining, by the computing system and based on the output, that training of the first model is complete such that the first model is a first trained model; determining, by the computing system and based on the output, that training of the second model is complete such that the second model is a second trained model; generating, by the computing system and using the first trained model, a first additional amino acid sequence of an additional light chain of an antibody; generating, by the computing system and using the second trained model, a second additional amino acid sequence of an additional heavy chain of an antibody; and combining, by the computing system, the first additional amino acid sequence and the second additional amino acid sequence to produce a third additional amino acid sequence, the third additional amino acid sequence including a light chain and a heavy chain of an additional antibody.

19. The method of 18, comprising evaluating, by the computing system, the third additional amino acid sequence with respect to one or more metrics, the one or more metrics including at least one of a number of hydrophobic amino acids included in the third additional amino acid sequence, a number of positively charged amino acids included in the third additional amino acid sequence, a number of negatively charged amino acids included in the third additional amino acid sequence, a number of uncharged amino acids included in the third additional amino acid sequence, a level of expression of the third additional amino acid sequence, a melting temperature of the third additional amino acid sequence, or a level of self-aggregation of the third additional amino acid sequence.

20. The method of 18, comprising analyzing, by the computing system and using the generative adversarial network, the third additional amino acid sequence with respect to a further plurality of amino acid sequences to produce an additional output, wherein: the further plurality of amino acid sequences is included in additional training data for the generative adversarial network; the additional training data includes different amino acid sequences of antibodies than the amino acid sequences included in the training data; and the additional output indicates an additional measure of similarity between the third additional amino acid sequence and at least a portion of the further plurality of amino acid sequences.

21. A system comprising: one or more hardware processors; and one or more non-transitory computer readable media storing computer-executable instructions that, when executed by the one or more hardware processors, cause the one or more processor to perform operations comprising: obtaining first data indicating a first amino acid sequence of a first antigen; obtaining second data indicating binding interactions between individual antibodies of a first plurality of antibodies and one or more antigens; determining a second amino acid sequence of a second antigen of the one or more antigens that has at least a threshold amount of identity with respect to at least a portion of the first amino acid sequence of the first antigen; determining, based on the second data, a group of the first plurality of antibodies included in the second data that have at least a first threshold amount of binding interaction with the second antigen; generating, using a generative adversarial network, a model to produce additional amino acid sequences of additional antibodies having at least a threshold probability of having at least a second threshold amount of binding interaction with the first antigen, wherein the model is generated based on the first amino acid sequence of the first antigen and the group of the first plurality of antibodies; and generating, using the model, a second plurality of amino acid sequences of antibodies that correspond to the first antigen.

22. The system of 21, wherein the binding interactions include at least one of a binding affinity or a binding avidity.

23. The system of 21 or 22, wherein: the binding interactions indicate an amino acid sequence of a binding region of an antibody of the first plurality of antibodies and an additional amino acid sequence of an epitope region of an antigen of the one or more antigens, and the binding region binds to the epitope region.

24. The system of 23, wherein the binding interactions indicate couplings between amino acids included in the binding region and additional amino acids included in the epitope region.

25. The system of any one of 21-24, wherein the binding interactions include equilibrium constants between the individual antibodies of a first plurality of antibodies and the one or more antigens.

26. The system of any one of 21-25, wherein the operations comprise evaluating, using a software tool, one or more metrics with respect to the second plurality of amino acid sequences of antibodies, the one or more metrics including at least one of a number of hydrophobic amino acids included in individual amino acid sequences of the second plurality of amino acid sequences, a number of positively charged amino acids included in individual amino acid sequences of the second plurality of amino acid sequences, a number of negatively charged amino acids included in individual amino acid sequences of the second plurality of amino acid sequences, a number of uncharged amino acids included in individual amino acid sequences of the second plurality of amino acid sequences, a level of expression of individual antibodies, a melting temperature of individual antibodies, or a level of self-aggregation of individual antibodies.

27. A system comprising: one or more hardware processors; and one or more non-transitory computer readable media storing computer-executable instructions that, when executed by the one or more hardware processors, cause the one or more processor to perform operations comprising: obtaining first data indicating a composition of a target molecule; obtaining second data indicating binding interactions between individual first proteins of a plurality of first proteins and one or more additional molecules; determining a composition of an additional molecule of the one or more additional molecules that has at least a threshold amount of similarity with respect to at least a portion of the composition of the target molecule; determining, based on the second data, a group of the plurality of first proteins included in the second data that have at least a first threshold amount of binding interaction with the additional molecule; generating, using a generative adversarial network, a model to produce additional amino acid sequences of additional proteins having at least a threshold probability of having at least a second threshold amount of binding interaction with the target molecule, wherein the model is generated based on the composition of the target molecule and the group of the plurality of first proteins; and generating, using the model, a plurality of second amino acid sequences of second proteins that correspond to the target molecule.

28. The system of 27, wherein the target molecule includes a protein.

29. The system of 28, wherein the protein includes an antigen, the plurality of first proteins include first antibodies, and the plurality of second proteins include second antibodies.

30. A system comprising: one or more hardware processors; and one or more non-transitory computer readable media storing computer-executable instructions that, when executed by the one or more hardware processors, cause the one or more processor to perform operations comprising: generating, using a generative adversarial network, a plurality of first amino acid sequences, individual first amino acid sequences of the plurality of first amino acid sequences corresponding to antibody light chains; generating, using the generative adversarial network, a plurality of second amino acid sequences, individual second amino acid sequences of the plurality of second amino acid sequences corresponding to antibody heavy chains; combining, using the generative adversarial network, a first amino acid sequence of the plurality of first amino acid sequences with a second amino acid sequence of the plurality of second amino acid sequences to produce a third amino acid sequence, the third amino acid sequence corresponding to an antibody including a light chain corresponding to the first amino acid sequence and a heavy chain corresponding to the second amino acid sequence; and analyzing, using the generative adversarial network, the third amino acid sequence with respect to an additional plurality of amino acid sequences to produce an output, the additional plurality of amino acid sequences being included in training data for the generative adversarial network and the output indicating a measure of similarity between the third amino acid sequence and at least a portion of the additional plurality of amino acid sequences.

31. The system of 30, wherein combining the first amino acid sequence with the second amino acid sequence includes concatenating the second amino acid sequence to the first amino acid sequence.

32. The system of 30 or 31, wherein: the generative adversarial network includes a first generating component that implements a first model to generate the plurality of first amino acid sequences and a second generating component that implements a second model to generate the plurality of second amino acid sequences; the first model includes a first function having one or more first variables and one or more first weights; and the second model includes a second function different from the first function, the second function including one or more second variables and one or more second weights.

33. The system of 32, wherein the third amino acid sequence is analyzed by a discriminator and the output is provided to at least one of the first generating component or the second generating component.

34. The system of 33, wherein the first generating component modifies the first model based on the output.

35. The system of 33, wherein the second generating component modifies the second model based on the output.

36. The system of any one of 30-35, wherein the first amino sequence includes at least a portion of a first variable region of an antibody light chain and the second amino acid sequence includes at least a portion of a first variable region of an antibody heavy chain.

37. The system of any one of 30-36, wherein the first amino acid sequence includes at least a portion of a first variable region and a first constant region of an antibody light chain and the second amino acid sequence includes at least a portion of a second variable region and a second constant region of an antibody heavy chain.

38. The system of any one of 30-37, wherein the operations comprise: determining, based on the output, that training of the first model is complete such that the first model is a first trained model; determining, based on the output, that training of the second model is complete such that the second model is a second trained model; generating, using the first trained model, a first additional amino acid sequence of an additional light chain of an antibody; generating, using the second trained model, a second additional amino acid sequence of an additional heavy chain of an antibody; and combining the first additional amino acid sequence and the second additional amino acid sequence to produce a third additional amino acid sequence, the third additional amino acid sequence including a light chain and a heavy chain of an additional antibody.

39. The system of 38, wherein the operations comprise evaluating the third additional amino acid sequence with respect to one or more metrics, the one or more metrics including at least one of a number of hydrophobic amino acids included in the third additional amino acid sequence, a number of positively charged amino acids included in the third additional amino acid sequence, a number of negatively charged amino acids included in the third additional amino acid sequence, a number of uncharged amino acids included in the third additional amino acid sequence, a level of expression of the third additional amino acid sequence, a melting temperature of the third additional amino acid sequence, or a level of self-aggregation of the third additional amino acid sequence.

40. The system of 38, the operations comprising analyzing, using the generative adversarial network, the third additional amino acid sequence with respect to a further plurality of amino acid sequences to produce an additional output, wherein: the further plurality of amino acid sequences is included in additional training data for the generative adversarial network; the additional training data includes different amino acid sequences of antibodies than the amino acid sequences included in the training data; and the additional output indicates an additional measure of similarity between the third additional amino acid sequence and at least a portion of the further plurality of amino acid sequences.

41. A method comprising: obtaining a training dataset including amino acid sequences of proteins; generating structured amino acid sequences based on the training dataset; generating a model to produce additional amino acid sequences that correspond to the amino acid sequences included in the training dataset using the structured amino acid sequences and a generative adversarial network; generating the additional amino acid sequences using the model and an input vector; and evaluating the additional amino acid sequences according to one or more criteria to determine metrics for the additional amino acid sequences.

42. The method of 41, further comprising determining a number of variations of an amino acid sequence included in the additional amino acid sequences with respect to a protein derived from a gene of a germline.

43. The method of 41 or 42, wherein the generative adversarial network includes a Wasserstein generative adversarial network.

44. The method of any one of 41-43, wherein the structured amino acid sequences are represented in a matrix that includes a first number of rows and a second number of columns, individual rows of the first number of rows corresponding to a position of a sequence, and individual columns of the second number of columns corresponding to individual amino acids.

45. The method of any one of 41-44, wherein one or more characteristics of proteins corresponding to the additional amino acid sequences have at least a threshold similarity to one or more characteristics of the proteins included in the training dataset.

46. The method of any one of 41-45, wherein the one or more characteristics include at least one of structural position features, tertiary structure features, or biophysical properties.

47. The method of any one of 41-46, wherein the proteins include antibodies, affibodies, affilins, affimers, affitins, alphabodies, anticalins, avimers, monobodies, designed ankyrin repeat proteins (DARPins), nanoCLAMP (clostridal antibody mimetic proteins), antibody fragments, or combinations thereof.

48. A method comprising: obtaining a training dataset including amino acid sequences of antibodies; generating a model to produce additional amino acid sequences of antibodies that have one or more characteristics that are similar to characteristics of the antibodies of the training dataset using a generative adversarial network; and generating the additional amino acid sequences using the model and an input vector.

49. The method of 48, further comprising applying a classification system to the amino acid sequences of the training dataset, the classification system indicating a first number of positions to associate with heavy chain regions of the antibodies and a second number of positions to associate with light chain regions of the antibodies.

50. The method of 48 or 49, further comprising: using a first generative adversarial network and a first training dataset to generate a first model to produce a plurality of heavy chain regions of antibodies; using a second generative adversarial network and a second training dataset to generate a second model to produce a plurality of light chain regions of antibodies; and generating antibody sequences by combining at least portions of the plurality of heavy chain regions and with at least portions of the light chain regions.

51. A method comprising: training a first model of a first generating component of a generative adversarial network using a first training dataset including a first number of amino acid sequences of light chains of antibodies to produce a first trained model; training a second model of a second generating component of the generative adversarial network using a second training dataset including a second number of amino acid sequences of heavy chains of antibodies to produce a second trained model, wherein training the second generating component proceeds at a first rate that is different from a second rate of training the first generating component; generating, using the first generating component, a first additional number of first additional amino acid sequences corresponding to antibody light chains; generating, using the second generating component, a second additional number of second additional acid sequences corresponding to antibody heavy chains; and combining, using the generative adversarial network, a first amino acid sequence of the first additional number of first additional amino acid sequences with a second amino acid sequence of the second additional number of second additional amino acid sequences to produce a third amino acid sequence, the third amino acid sequence corresponding to an antibody including a light chain corresponding to the first amino acid sequence and a heavy chain corresponding to the second amino acid sequence.

52. The method of 51, wherein the second generating component is trained using a number of hobbled weights to decrease a rate of training the second generating component relative to an additional rate of training the second generating component without the number of hobbled weights.

53. The method of 51 or 52, wherein the second generating component is trained by slowing a gradient of the second generating component.

54. The method of any one of 51-53, comprising: training the second generating component during a first period of time; determining that a first plurality of amino acid sequences produced during an end portion of the first period of time have a first level of quality; training the first generating component for a second period of time that includes the first period of time and is longer than the first period of time; determining that a second plurality of amino acid sequences produced during an end portion of the second period of time have the first level of quality; training the second generating component during a third period of time that is subsequent to the second period of time; determining that a third plurality of amino acid sequences produced during an end portion of the third period of time have a second level of quality; training the first generating component for a fourth period of time that includes the third period of time and is longer than the third period of time; and determining that a fourth plurality of amino acid sequences produced during an end portion of the fourth period of time has the second level of quality.

55. The method of 54, wherein a total amount of time elapsed to train the second generating component is less than a total amount of time elapsed to train the first generating component.

56. A method comprising: obtaining a training dataset including amino acid sequences of proteins; generating structured amino acid sequences based on the training dataset; generating a model to produce additional amino acid sequences that correspond to the amino acid sequences included in the training dataset using the structured amino acid sequences and a generative adversarial network; generating the additional amino acid sequences using the model and an input vector; determining an amount of similarity between individual additional amino acid sequences and an amino acid sequence of an antibody produced in relation to expression of a germline gene; determining a length of respective complementarity-determining region (CDR) H3 regions of the individual amino acid sequences; and evaluating the additional amino acid sequences based on the respective amounts of similarity and the respective lengths of the CDR H3 regions of the additional amino acid sequences.

57. The method of 56, comprising evaluating the additional amino acid sequences based on a measure of immunogenicity of the additional amino acid sequences.

58. The method of 57, wherein the measure of immunogenicity corresponds to a measure of major histocompatibility complex (MHC) Class II binding.

59. A system comprising: one or more hardware processors; and one or more non-transitory computer readable media storing computer-executable instructions that, when executed by the one or more hardware processors, cause the one or more processor to perform operations comprising: training a first model of a first generating component of a generative adversarial network using a first training dataset including a first number of amino acid sequences of light chains of antibodies to produce a first trained model; training a second model of a second generating component of the generative adversarial network using a second training dataset including a second number of amino acid sequences of heavy chains of antibodies to produce a second trained model, wherein training the second generating component proceeds at a first rate that is different from a second rate of training the first generating component; generating, using the first generating component, a first additional number of first additional amino acid sequences corresponding to antibody light chains; generating, using the second generating component, a second additional number of second additional acid sequences corresponding to antibody heavy chains; and combining, using the generative adversarial network, a first amino acid sequence of the first additional number of first additional amino acid sequences with a second amino acid sequence of the second additional number of second additional amino acid sequences to produce a third amino acid sequence, the third amino acid sequence corresponding to an antibody including a light chain corresponding to the first amino acid sequence and a heavy chain corresponding to the second amino acid sequence.

60. The system of 59, wherein the second generating component is trained using a number of hobbled weights to decrease a rate of training the second generating component relative to an additional rate of training the second generating component without the number of hobbled weights.

61. The system of 59 or 60, wherein the second generating component is trained by slowing a gradient of the second generating component.

62. The system of any one of 59-61, wherein the operations comprise: training the second generating component during a first period of time; determining that a first plurality of amino acid sequences produced during an end portion of the first period of time have a first level of quality; training the first generating component for a second period of time that includes the first period of time and is longer than the first period of time; determining that a second plurality of amino acid sequences produced during an end portion of the second period of time have the first level of quality; training the second generating component during a third period of time that is subsequent to the second period of time; determining that a third plurality of amino acid sequences produced during an end portion of the third period of time have a second level of quality; training the first generating component for a fourth period of time that includes the third period of time and is longer than the third period of time; and determining that a fourth plurality of amino acid sequences produced during an end portion of the fourth period of time has the second level of quality.

63. The system of 62, wherein a total amount of time elapsed to train the second generating component is less than a total amount of time elapsed to train the first generating component.

64. A system comprising: one or more hardware processors; and one or more non-transitory computer readable media storing computer-executable instructions that, when executed by the one or more hardware processors, cause the one or more processor to perform operations comprising:

obtaining a training dataset including amino acid sequences of proteins; generating encoded amino acid sequences based on the training dataset; generating a model to produce additional amino acid sequences that correspond to the amino acid sequences included in the training dataset using the encoded amino acid sequences and a generative adversarial network; generating the additional amino acid sequences using the model and an input vector; determining an amount of similarity between individual additional amino acid sequences and an amino acid sequence of an antibody produced in relation to expression of a germline gene; determining a length of respective complementarity-determining region (CDR) H3 regions of the individual amino acid sequences; and evaluating the additional amino acid sequences based on the respective amounts of similarity and the respective lengths of the CDR H3 regions of the additional amino acid sequences.

65. The system of 64, wherein the operations comprise evaluating the additional amino acid sequences based on a measure of immunogenicity of the additional amino acid sequences.

66. The system of 65, wherein the measure of immunogenicity corresponds to a measure of major histocompatibility complex (MHC) Class II binding.

EXAMPLES

We demonstrate the use of a Generative Adversarial Network (GAN), trained from a set of over 400,000 light and heavy chain human antibody sequences, to learn the rules of human antibody formation. The resulting model surpasses common in silico techniques by capturing residue diversity throughout the variable region, and is capable of generating extremely large, diverse libraries of novel antibodies that mimic somatically hypermutated human repertoire response. This method permits us to rationally design de novo humanoid antibody libraries with explicit control over various properties of our discovery library. Through transfer learning, we are able to bias the GAN to generate molecules with key properties of interest such as improved stability and developability, lower predicted MHC Class II binding, and specific complementarity-determining region (CDR) characteristics. These approaches also provide a mechanism to better study the complex relationships between antibody sequence and molecular behavior, both in vitro and in vivo. We validate our method by successfully expressing a proof-of-concept library of nearly 100,000 GAN-generated antibodies via phage display. We present the sequences and homology-model structures of example generated antibodies expressed in stable CHO pools and evaluated across multiple biophysical properties. The creation of discovery libraries using our in silico approach allows for the control of pharmaceutical properties such that these therapeutic antibodies can provide a more rapid and cost-effective response to biological threats.

Antibodies are an important class of biologics-based therapeutics with clear advantages of specificity and efficacy. The high cost and long development times, however, present key challenges in the accessibility of monoclonal antibody therapeutics. To quickly respond to known and new pathogens and disease, and to provide affordable, high quality treatment to patients around the globe, a molecule must be designed for activity; but it must also be made developable and safe for patients. Adding to their overall cost and process time, many antibodies suffer from poor yields or require individually customized processing protocols or formulations because their biophysical properties cause them to aggregate, unfold, precipitate, or undergo other physical modification during processing into a drug product. Even with the significant amounts of research being put into discovering pharmacologically-active antibodies and understanding their physical and biological behavior, they remain challenging to identify for given diseases or pathogens and to optimize for developability.

Discovery of therapeutic antibodies frequently involves either display methodologies or B-cells isolated from humans or animals that have been exposed to an antigen or a disease target of interest. Although B-cell isolation and deep sequencing workflows have improved over the years in regards to cost, labor, and speed, there are still inherent limitations when considering the process as an antibody discovery platform. A sufficient immunological response is required from the specific subjects being used, and due to the low number and diversity of the subjects being used, there can be insufficient antibody sequence diversity that is expressed. There is also the challenge of overcoming B-cell-driven survival against specific epitopes in which therapeutically viable epitopes are not utilized by an immune response when they are out-competed by a dominant binding epitope, leading to an antibody panel focused on a limited epitope. The library approach can provide a search across a wider range of sequence space, but most examples of synthetic libraries result in a sequence profile which is quite different from those expressed by the human immune system. In both cases, there is little to no ability to control the chemical, biophysical, or biological characteristics of the identified candidates. As a result, discovered antibodies frequently have the aforementioned features seriously complicating their developability and stability.

A recent synthetic library approach implements random mutagenesis in which specific residues are allowed to vary in type following statistical rules for frequency of appearance by location in the antibody (commonly known as positional frequency analysis, PFA). PFA and other related methods do not take into account any interactions between residues except to the extent that such interactions limit the expressibility of the protein. While this widely explores the sequence space, it ignores how residue types interact to form stabilizing features such as hydrogen or ionic bonds. Random assignment is also done without consideration of the characteristics of the final antibody entity, leading to some that have unusual and potentially problematic protein surface features.

Another drawback to most synthetic library approaches is that they focus solely on the complementary-determining regions (CDRs) of the antibodies. While the CDRs are the most critical portion of the antibody variable region in determining binding interactions, many Kabat-defined CDR positions are part of the core immunoglobulin (Ig) fold, and many of the framework residues can also play an important role in direct antigen binding, stability of the molecule, and CDR orientation.[6] By limiting mutations to the CDRs, existing libraries neglect the possibility of improved bioactivity and developability afforded by some framework mutations.

Even with an identified therapeutic antibody, improving that antibody's production and purification behavior through sequence modification can be challenging. While many papers have been published trying to develop a predictable connection between an antibody's sequence and/or computed molecular structure and the molecule's various physical characteristics, the connection is elusive as it involves complex nonlinear interactions between the constituent amino acid residues. Frequently, such work involves an exceptionally small number of molecules, frequently under 200 and often under 50, from a non-diverse set of sequences—a small number of parental sequences, several parents with a small number of highly-related sequence variants, or a single antibody with mutational scanning. Such approaches give information on an individual antibody or small group, but are highly unlikely to generalize the complexity of residue interactions to other antibodies. Such understanding requires exploration of the wider hyperdimensional space of antibody sequences. Computational approaches used to optimize molecular behavior also frequently ignore whether the revised molecule remains similar to human antibodies. That assessment is left to expensive in vitro studies.

Deep learning offers one route to better capture the complex relationships between sequence and protein behavior and has been the focus of many recent publications. Within the context of discovery and libraries, the generative models such as Generative Adversarial Networks (GANs) and autoencoder networks (AEs) are of particular interest as they have been shown to be viable for generating unique sequences of proteins and nanobodies and antibody CDRs. But these efforts focus on short sequences of proteins or portions of antibodies. Use of these approaches in the full antibody sequence space entails a unique set of challenges for machine learning models.

Antibodies derive from different germline backgrounds, are much larger in size, and are composed of multiple chains, leading to a more complex sequence and structural space. More complexity in a machine learning setting generally requires more data to resolve. However, sequence data, with associated experimental data, is more limited for antibodies and is far more costly to come by than small molecules.

Here, we present the Antibody-GAN, a new synthetic approach to designing a novel class of antibody therapeutics which we term "humanoid" antibodies. The Antibody-GAN uses modified Wasserstein-GANs for both single-chain (light or heavy chain) and paired-chain (light and heavy chain) antibody sequence generation. These GANs allow us to encode key properties of interest into our libraries for a feature-biased discovery platform. Our Antibody-GAN architecture (1) captures the complexity of the variable region of the standard human antibody sequence space, (2) provides a basis for generating novel antibodies that span a larger sequence diversity than is explored by standard in silico generative approaches, and (3) provides, through transfer learning (continued training of a model with a subset of data with specific desirable characteristics), an inherent method to bias the physical properties of the generated antibodies toward improved developability and chemical and biophysical properties.

We demonstrate the GAN library biasing on such properties as a reduction of negative surface area patches, identified as a potential source of aggregation, thermal instability, and possible half-life reductions, and away from MHC class II binding, which may reduce the immunogenicity of the generated antibodies. We show, additionally, library biasing to a higher isoelectric point (pI) to reduce aggregation and prevent precipitation in therapeutic formulations, and towards longer CDR3 lengths which can increase diversity and has been known to create more effective therapeutics for a class of targets.

To demonstrate the viability of the Antibody-GAN to generate humanoid antibody sequences, the GAN was used to generate a proof-of-concept validation library of 100k sequences from 4 germline subgroups. These sequences were generated using two single-chain GANs (each trained on a set of 400,000 heavy or light chain sequences from human-repertoire antibodies). The GAN sequences were expressed as antibody antigen binding fragments (Fabs) in phage. Two of the less-represented germline subgroups were optimized for germline agreement using transfer learning. From this initial library, we present the sequences, structure, and biophysical properties of two antibodies with divergent surface patch features which were expressed in stable Chinese hamster ovary (CHO) cells.

Generative Adversarial Networks for Antibody Design

The general Antibody-GAN architecture in which a set of real training variable-region (Fv) antibody sequences are fed to a discriminator of the GAN along with the output of the generator. The generator takes a vector of random seeds as input, and outputs a random synthetic antibody sequence. During training, the discriminator is progressively trained to attempt to accurately distinguish between the real and the synthetic sequences and the generator is progressively trained to produce synthetic sequences that cannot be distinguished from the real human repertoire sequences in the training set. After initial training of the Antibody-GAN from the entire training set, transfer learning can be used to bias the GAN towards generating molecules with desired properties.

As a demonstration of the general architecture and training approach, an Antibody-GAN was trained using a set of 400,000 human-repertoire sequences, per chain, randomly selected from the Observed Antibody Space project (OAS). Prior to training, the sequences were all structurally aligned using the AHo numbering system which enables direct comparison of residues at the same structural position across the dataset. This greatly simplifies the relationships that the GAN must capture both for generation and discrimination. Additional training details are provided in the methods section.

Sequences from the Antibody-GAN (GAN), the OAS training set, and a set of sequences with 100% germline framework and PFA-generated CDRs (PFA) were compared by selecting a random set of 10,000 sequences, all classified as germline HV3-30, from the training set and all three synthetic sets. These were evaluated on the distribution of percent germline agreement of the framework residues. Within the human repertoire, deviations from framework germline agreement arise from the sequences having undergone somatic hypermutation during B-cell maturation. Molecules from the Antibody-GAN model (GAN) deviate from germline much like the OAS. Note that the PFA set uses an exact germline framework; as such, the germline agreement is always 100%.

The diversity of the heavy variable (HV) CDR3 was used as an indicator of the diversity of binding paratopes within a given set and was assessed using (1) pairwise Levenshtein distances calculated from only the HV CDR3 residues in all three sets, and (2) the scores from the first two components of a principal component analysis (PCA) model on the aligned HV CDR3 sequences from the OAS, GAN, and PFA data. The OAS set in general shows the greatest diversity in HV, however, the GAN and PFA sets have similar diversity to the main peak in OAS, with the GAN exhibiting slightly larger diversity than PFA.

The distribution of sequence variability in the OAS human repertoire set is more similar to those seen in the GAN set, than the distribution in the PFA set, which diverges significantly from the other two sets, particularly in the high-density regions of the plots. The explained variance of PCA components 1 and 2 are 10% and 4%, respectively.

While these are only small portions of the overall variance in the HV CDR3, they do represent the largest covarying relationships between the HV CDR3 residues and indicate that the Antibody-GAN approach captures significant relationships in human repertoire HV CDR3 that the PFA approach does not. The KL-divergence is a measure of how different two distributions are from each other, with a value of 0 indicating identical distributions and values tending away from 0 indicating more divergent distributions. The KL-divergence of the distribution over PC1, the component that captures most of the variance in CDR3, for the OAS and GAN sets is 0.57. The KL-divergence of PC1 for the OAS and PFA sets is 1.45. These distributions for PC1 and PC2 for both the GAN and the PFA sets, relative to OAS can be determined. The PFA set shows notably more divergence from the OAS and GAN sets and raises the question of how well the PFA approach reproduces human paratopes, as well as the diversity of these paratopes.

Bias and Control of Antibody Discovery Libraries

Our generative, deep-learning approach to humanoid antibody library generation not only results in antibody libraries that are more human-like than existing synthetic library approaches, but it also allows us to control the features of our libraries. A subset of these libraries were generated using a deep-learning technique known as transfer learning, which biases networks from the general Antibody-GAN-learned properties towards specific features of interest. The corresponding heatmap shows the difference, in percent of sequences in a given bin, between each library and OAS.

Biasing on the length of the primary binding paratope, CDR H3, of an antibody sequence can be determined. We compare 4 libraries to OAS: the baseline Antibody-GAN (GAN) from above, Antibody-GANs transfer learned to small (GAN −C) and to large (GAN +C) CDR H3 lengths, and the PFA-generated library (PFA) from above. The baseline Antibody-GAN library shows a total 27% difference from OAS in its CDR H3 distribution. Though still significantly different, it more closely reproduces the OAS distribution over CDR H3 than PFA (38% difference) or the other two intentionally biased libraries. The GAN −C library was generated by a model transfer-learned on a small subset of about 1,000 sequences from the GAN library which had CDR H3 lengths of less than 12 and resulted in a library with 68% shift to shorter CDR H3 sequences. The GAN +C was similarly transfer-learned on approximately 1,000 sequences from the GAN library which had CDR H3 lengths of >22, creating a very significant 89% bias towards longer CDR H3 sequences. By creating antibodies with longer CDRs, and therefore more residues to vary, the GAN +C library also inherently biases towards diversity. Antibodies with long CDR H3s have also been shown to have better success as therapeutics for diseases such as human immunodeficiency virus (HIV),[57] and may be useful as a discovery sub-library for targets that may require such long, exposed paratopes.

Biasing on immunogenicity of the heavy chain using a major histocompatibility class II (MHCII) binding score derived from in silico peptide fragment-MHCII binding affinity predictions can be determined. We use an in-house machine learning predictor for peptide-MHCII binding similar in effect to the binding prediction tools provided by the Immune Epitope DataBase (IEDB). Peptide-MHCII binding is the first step in the T-cell-mediated immune response and the clearest handle available for practically mitigating immunogenicity risk. The GAN library, with only a 2% difference from OAS in predicted immunogenicity, is statistically indistinguishable (at $p<0.0001$) from the human repertoire training set, whereas PFA shows a statistically significant 11% shift towards higher immunogenicity. The GAN −I library, using a similar transfer learning approach to the one described above, shows a total 76% shift to lower predicted MHCII binding than human repertoire. Reduced MHCII binding is presumed to reduce the likelihood of immunogenic response as the binding is a necessary first step in that response. The resulting biased GAN −I should generate molecules with lower chance of immunogenic response. This large bias to sequences of lower immunogenicity is a significant bias towards higher quality antibody therapeutics, and could result in a library of safer treatments for patients.

The extent to which this biasing corresponds to lower immunogenicity will largely depend on the quality of the model used to choose the transfer samples. As a control condition, the GAN +I library shows 49% bias towards increased MHCII binding. While such a higher-immunogenicity biased model would not usually be of interest in developing a library, it could provide a means to generate molecules to help validate the underlying MHCII binding model, yet again highlighting the utility of a GAN method as a tool to explore molecular and therapeutic space.

For antibody therapeutics, the isoelectric point (pI, the pH at which the molecule is neutral) is a key measure of developability since a pI near the formulation pH may lead to high viscosity and aggregation or precipitation. A slightly acidic pH generally results in a higher overall charge leading to more recent formulations centered around pH 5.5. To remain stable in solution, therapeutic antibodies would ideally need to have a pI of greater than 8.5 for the overall molecule. The GAN library provides a distribution of pI for the Fv portion of the antibody that is statistically indistinguishable from OAS, and the PFA library creates a small 11% bias towards higher Fv pI. We show, with the GAN −P library, that we can bias the library with a 79% shift to lower Fv pI via transfer learning. The GAN +P library, however, shows a 43% increase in sequences with a calculated Fv pI greater than 9, resulting in likely a significant bias towards developability.

Large surface patches in antibody therapeutics have been linked to developability issues such as aggregation, thermal instability, elevated viscosity, and increased clearance rate, but also to improvement of specificity, particularly when the patches are related to charge. As such, biasing a library towards larger or smaller patches might have beneficial effects. They also serve as an example of generic biasing models towards desired structural properties. Biasing on the maximum negative surface patch area of a molecule, calculated using structure-based homology modeling can be determined. Large negative patches have been shown to increase antibody viscosity at high therapeutic concentrations. Once again, the GAN library is statistically equivalent to OAS in maximum negative patch size with only a 3% difference, demonstrating the model's ability to capture human repertoire. The PFA library maintains a small but significant 7% shift to lower negative surface patch area. The GAN −N library shows that we can intentionally shift our library towards smaller negative surface patches and away from known developability issues with a 31% bias, as shown in GAN −N. The GAN +N library shows that we can also shift in the other direction with a 36% bias towards larger negative patches. Structure-based properties like surface patch can be more difficult to bias than sequence-based ones due to (1) the non-Gaussian distribution of the property and (2) the added layer of abstraction and complexity away from sequence. These issues can likely be resolved by increasing the number of sequences in the transfer learning training set by, for example, iteratively training and sampling. For more complex properties, layers can be added to the model itself during transfer-learning.

Combinatorial Library Design and Expression of Diverse Germlines

The synthesis of a diverse, de novo antibody discovery library comprising specific sequences can be costly. Such specific sequence targeting cannot be done with standard codon degeneracy approaches. To greatly reduce this cost, we used a chain-oriented approach to our library design, combinatorially combining heavy and light chains that are created with specific amino-acid sequences designed by the Antibody-GAN rather than designing each Fv individually. The Antibody-GAN architecture is designed to be modular. After training with paired-chain Fv sequences, the heavy chain generator and light chain generator can be separately used to generate single-chain sequences, such that any independently generated heavy chain should pair with any independently generated light chain to create a full Fv which maintains the library's intended features. All Antibody-GAN and transfer-learned Antibody-GAN libraries were generated from models trained in this manner.

It is also possible to split apart the Antibody-GAN model, initially, into single chain models. These must be trained on single chain sequences and may be useful when creating diverse libraries of varying germlines, when there is no property of interest associated with the full Fv for which we want to bias. Because there are few public data sets providing developability, expression, stability, and other properties on paired-chain sequences, we choose to synthesize a naive, unbiased initial discovery library to express in phage. Our goal for this first library is to reproduce human repertoire. In doing this, we will also create a data set which can greatly inform biasing of future libraries. As such, the subsequent GAN libraries and molecules were generated using the single chain version of the Antibody-GAN.

For our initial library, we selected heavy chain germlines IGHV3-30 and IGHV1-2 to pair combinatorially with light chain germlines IGKV3-20 and IGKV1-39. The number of training set examples for IGHV1-2 and IGKV1-39 is lower than for the other two germlines, such that there are not enough examples to train a model of sufficient quality. The problem is compounded for other germlines with even fewer training examples. This can be remedied again by using transfer learning.

Because the HV3-30 and KV3-20 germlines are well-represented in the OAS training set, the models generate sequences of sufficient framework quality. More divergence from OAS in framework quality for the less-represented HV1-2 and KV1-39 germlines, respectively, was determined when generated by a base model without transfer learning. Only when the model is transfer-learned, allowed to continue training on only the germline subgroup of interest, is it then able to generate sequences with framework quality more closely matching OAS for HV1-2 and KV1-39.

While a full-scale production library might contain 10,000 or more individual single-chain sequences from each germline combined combinatorially to form billions of molecules, a proof-of-concept miniature library was created by selecting 158 sequences from each of these four germlines and combining them combinatorially to assemble a library of around 100,000 total sequences.

Fab fragment display levels for our 4 germline-paired sub-libraries were determined, each containing ~25,000 GAN-generated sequences. Display levels were estimated by capturing serial dilutions of purified phage on ELISA plates coated with anti-human Fab and detecting with anti-M13 antibodies conjugated to HRP. Average display levels, normalized for total phage concentration, of IgG Fab from each of the sub-libraries in polyclonal phage were determined. A slight bias for higher expression can be seen at higher concentrations for those germline sub-libraries which contain the KV1-39 sub-library. Whether or not this difference is actually significant and related to higher tolerability of KV1-39 sequences, or represents differential binding of the anti-human Fab capture antibody used in the ELISA, is an area of future studies.

To confirm the expressed Fab are indeed the designed, de novo sequences, we selected and sequenced ~30 colonies expressed in monoclonal phage from each of the 4 sub-libraries. Variable-region cladding of the selected sequences from the two sub-libraries expressing KV3-20 light chain to the 158 GAN-designed KV3-20 sequences shows primarily 1) our selection of colonies was random and provides good coverage of the space of designed sequences and 2) only a small fraction of the expressed sequences contained any amino acid mutations relative to the GAN-designed sequences; most matched our synthetic designs exactly.

Similar cladding of the selected sequences from the two sub-libraries expressing HV3-30 heavy chain was determined. The same observations can be made with this set. The selected sequences span the design space well, and show even fewer amino acid mutations and more exact matches to the de novo GAN-designed sequences than the KV3-20 set. Again, expression is shown for the sampled colonies and it is noted whether those sequences were paired with the KV3-20 light chain. Phage library sequences that are not marked as being paired with a light chain from the KV3-20 library were paired with a light chain sequence from the KV1-39 library.

A further subset of antibodies were selected from the HV3-30/KV3-20 sub-library to be expressed in stable CHO pools for biophysical analysis. The molecule mAb GAN-1285 was selected for its very large negative surface patch of ~600 Å$^2$, shown in red. Molecules with such a large maximum negative patch are relatively uncommon in the base Antibody-GAN distribution, but are interesting to investigate for developability purposes. The molecule mAb GAN-1528, by contrast, has a maximum negative surface patch of ~140 Å$^2$.

Biophysical Validation of CHO-Expressed GAN Antibodies

For the purpose of validation of our GAN approach and to interrogate the interesting property of maximum negative surface patch, we present the biophysical data of mAb GAN-1285 and mAb GAN-1528 after stable CHO expression and purification. Four key assays in our platform include: differential scanning fluorimetry (DSF), self-interaction nanoparticle spectroscopy (SINS), polyethylene glycol (PEG) solubility, and size-exclusion chromatography (SEC). These assays are commonly used to assess the stability and developability of therapeutic antibodies DSF results for mAb GAN-1285 and mAb GAN-1528, as well as a platform control antibody, MS-43 were determined. DSF assesses the temperature at which certain regions of the antibody begin to unfold. More stable, and thus more developable antibodies tend to have one or more regions unfold at higher temperatures and have a higher first-unfolding transition temperature. The identical constant regions of these three molecules all show an unfolding event at around 72° C., presumed to be the IgG CH2 region. The molecule with a very large negative surface patch, mAb GAN-1285, shows much lower thermal stability, with an initial unfolding event near 60° C. This is consistent with the notion that negative surface patches are known to be related to thermal instability.

The SINS assay is commonly used to interrogate whether a molecule will self interact, leading to issues in the manufacturing process as well as possible viscosity and filterability issues. Interestingly, the two GAN molecules exhibited the same SINS profile as the PBS negative control, indicating a low propensity to self interact, particularly compared to the positive control molecule, MS-63, known to have high self-interaction behavior.

The remaining assays, PEG solubility and SEC, show that both antibodies are reasonably soluble, and display relatively low amounts of high molecular weight (HMW) formation, although there are potentially significant differences between the two antibodies in both assays.

DISCUSSION

We describe here a new class of de novo human antibodies derived in silico, which we refer to as "humanoid", owing to their explicit requirement that generated sequences must mimic human antibody sequence patterns. While antibodies have excellent antigen specificity and have often been adapted as scaffolds for therapeutic applications, B-cells do not undergo selective pressure in vivo to produce antibodies which have ideal biotherapeutic characteristics. To reduce the cost of development and greatly increase the time-to-response for known or new diseases and pathogens, a discovery library must contain therapeutic antibodies with desirable features such as: expressibility in a host system, suitability for common protein manufacturing processes while achieving high product purity and yield, and exhibiting high stability during long-term storage conditions. In addition, these therapeutic libraries must also contain antibodies exhibiting in-use characteristics such as low viscosity for injectability at high concentration, long elimination half-lives to reduce dosing frequency, and high bioavailability for conservation of the injected dose. Here, we have described an Antibody-GAN approach to the in silico design of monoclonal antibodies which retain typical human repertoire characteristics such as diversity and immunogenicity, while raising the possibility of biasing the libraries in silico to achieve other desirable biotherapeutic features.

We experimentally validate our in silico approach via phage Fab-display of an initial library of ~100,000 GAN sequences and present the biophysical properties of two example GAN antibodies expressed in CHO. While the biophysical data of the CHO-expressed molecules are not sufficient to indicate any causal effect of the structural differences on the biophysical properties, they show that the molecules are folding appropriately and that they exhibit expected biophysical properties. These results show that the Antibody-GAN is capable of enabling study of large, truly diverse sets of thousands of full-length secreted antibodies, and hundreds of millions of antibody Fabs on phage for biophysical properties. These will provide a real basis to identify causal effect, or lack thereof, of structural properties and sequence on biophysical properties—and that data has the potential to feed in silico predictive models that are truly generalized across antibodies.

Ongoing research will be needed to determine precisely which antibody sequence, structure, or biophysical features will bias antibody libraries for developability, quality, and efficacy, as there are many nonlinear pathways for antibody optimization. Existing data sets which interrogate antibody therapeutic developability consist of, in a few cases, hundreds of molecules, but more commonly on the order of tens of antibodies. Deriving from sequence, or even structure, such complex properties as the viscosity or the chemical or thermal stability of an antibody will require far more than hundreds of example molecules. Until now, protein scientists have had to rely on previously-discovered antibodies and their nearby variants, which provide a very small random sampling of the true antibody space. The Antibody-GAN allows us to explore the human antibody space in a rational way. Using transfer learning to bias GANs for given properties, either those calculated on structures from homology modeling, or measured on physically expressed antibodies, we can now begin to understand such questions as how engineering for developability affects key properties like affinity and bio-availability. This provides a mechanism for in silico and in vitro generation of a much wider range of sequences with intentional biases forming deep, rich training sets for human antibody research.

Recent advances in the protein assay space now provide ultra high-throughput methods in phage or yeast to express and interrogate, for example, the stability of molecules,[68] and many more will come. We can now rationally design and create vast experimental antibody data sets for those and future methods, and begin to understand the properties of a developable and effective therapeutic drug.

Our Antibody-GAN approach, as a training-set generation tool, will greatly expand our knowledge of antibody design and behavior. It will also change the way we create therapeutics, by better reproducing properties of in vivo-derived antibodies with characteristics that can be tuned to make them better suited as biologics, for production and treatment. Humanoid discovery libraries generated in this way, will provide higher quality treatment and a more rapid and cost-effective response to biological threats and disease targets.

Methods

Training Set Data Sources

Data for the training sets was derived from the Observed Antibody Space (OAS) repository. Raw nucleotide sequences were automatically translated, classified, and structurally aligned using in-house software (Abacus™). The AHo structure numbering system was used for structural alignments of the variable regions.

To create the training sets, variable regions were first filtered to remove any sequences which were not classified as human variable regions, by our in-house software Abacus™, and then further cleaned to remove those sequences which contained stop codons, truncations, or insertions. Any sequence which had less than 85% agreement to its closest germline was also removed.

For any paired-chain model, the distinct sequences whose closest germline belonged to the heavy and light germline frameworks of interest were then extracted. These two subsets were randomly sampled and combined during training to create paired sequences.

For any single-chain model, the initial training set contained all represented germlines. If transfer learning was necessary, it was done on an extracted set of sequences whose closest germline belonged to the specific germline of interest.

Antibody-GAN Development and Training

The Antibody-GAN code was developed in Python. The Keras and Tensorflow deep-learning libraries were primarily used to build and train the Antibody-GAN. The Pandas and Numpy libraries were used to handle any data and training set construction. Other public libraries that were used in the development and analysis of the Antibody-GAN include: Sklearn, Scipy, and Seaborn.

The architecture of the Antibody-GAN is based on the Wasserstein-GAN (WGAN) (with gradient penalty) architecture, and therefore consists of a generator and a discriminator, which in the WGAN architecture is commonly referred to as a critic. The single-chain network generator takes as input a noise vector of size 296. This vector is fed into a dense layer, followed by 3 up-sampling and 2D convolutional transpose layers, and a final SoftMax layer to produce a 2D array of size 148×22. This 2D array corresponds to a one-hot-encoded representation of 148 residues and 22 possible amino acids (including deletions and Xs) of a light or heavy chain in an antibody sequence. Antibody sequences aligned by AHo numbering have 149 residues in either chain; to make the network structure simpler, we chose to remove one residue, which appears relatively constant in human repertoire, from each chain during encoding. When decoding, we add this constant residue back in. The discriminator, or critic, takes as input the same 148×22 encoding of an antibody chain and passes it through two 2D convolutional layers, followed by a flattening, dense layer and a single-node linear output.

The paired Antibody-GAN architecture is similar to the single-chain version, except that there are two generators with the same architecture (one per chain). The outputs of each independent-chain generator are concatenated into a 296×22 one-hot-encoded representation of an antibody sequence with both heavy and light chains. It is possible to extend the architecture when training or transfer learning to complex properties that require nonlinear interaction between the two chains. The paired-GAN critic takes as input a 296×22 one-hot-encoded representation of a paired-chain antibody sequence and maintains a similar architecture to the one described above.

The loss of the generator as well as the discriminator (critic) on fake (generated) and real (training set examples) were determined, during training of the single-chain HV3-30 GAN (using a batch size of 128). Quality was assessed by germline framework agreement over training epochs for this model. Training ends when the generated sequences begin showing sufficient quality.

Human monoclonal antibodies have been shown to have higher variability in the heavy chain than the light chain. This may lead to asynchronous optimization of the light chain generator and the heavy chain generator during training in the paired Antibody-GAN, leading to generated heavy chains of higher quality than the light chain. This can be resolved by freezing the layers of the heavy chain generator, once it has reached a state of creating sequences of sufficient quality, and continuing training on the network until the light chain generator has reached a desired quality.

PFA Set Creation and OAS Set Selection

The IGHV3-30/IGKV3-20 PFA-based sets used above were created using the IGHV3-30 and IGKV3-20 training sets extracted from the OAS, which consisted of ~250,000 and ~150,000 sequences respectively. The 100% germline framework for IGHV3-30 was used as a constant framework for all heavy chain PFA sequences, and the 100% IGKV3-20 germline framework was used for all light chains. Each residue in the CDRs (CDR1, CDR2, and CDR3) were then generated using positional frequency analysis; sampling randomly from a distribution representing the frequency of amino acids in the training set, for any given position.

10,000 heavy-chain sequences and 10,000 light chain sequences were created in this manner and then randomly paired together to create a set of 10,000 sequences with full variable regions.

The OAS sets from above were created by randomly downsampling 10,000 sequences from each of the IGHV3-30 and IGKV3-30 training sets and then pairing together to create a set of 10,000 sequences with full variable regions.

DR3 PCA

To perform the PCA analysis, the aligned CDR3 of a given antibody was one-hot encoded into a vector representation. A 2-component PCA model was built, using the sklearn library, on those one-hot encoded vectors from all sequences of the OAS set, the PFA set, and the base GAN set (totaling 30,000 samples). Heavy chain and light chain models were built and trained separately.

Antibody-GAN Biasing Sources

CDR H3

Our in-house software, Abacus™, was used to assess the length of the CDR H3 from any training set, GAN-generated set, or PFA-generated set.

Calculated Immunogenicity

MHCII is a polymorphic transmembrane protein that binds and presents fragments of foreign, extracellular proteins to T-cell receptors (TCRs) to initiate an adaptive immune response. The MHCII binding score is a composite metric intended to quantify the immunogenicity risk in a sequence based on whether its constituent peptides are predicted to bind strongly and promiscuously to MHCII proteins. The quality of this metric depends on the selection of an accurate peptide-MHCII binding predictor and a reasonable method for aggregating predictions across the peptide fragments in a sequence and across allelic variants of MHCII.

We developed a machine learning algorithm for peptide-MHCII binding affinity prediction, trained on the peptide-MHCII binding affinity data set used to train NetMHCIIpan-3.2 and reported by Jensen et al. Several machine learning algorithms have been developed that outperform traditional matrix-based approaches to peptide-MHCII binding affinity prediction, including NetMHCII-pan and, more recently, MARIA.[40,54] We use our in-house MHCII binding predictor for ease of integration with our other sequence analysis tools and based on favorable accuracy comparisons with published benchmarks (not shown in the present report). Predictions from our models are generally correlated with the "IEDB recommended" algorithm for peptide-MHCII binding prediction.[60]

To calculate a sequence MHCII binding score, we first break the sequence into each of its constituent 15mer peptide fragments (sliding window of 15, stride of 1). For each 15mer, we use allele-specific models to predict the binding affinity to 8 common allelic variants of MHCII (those encoded by HLA alleles DRB1*0101, DRB1*0301, DRB1*0401, DRB1*0701, DRB1*0801, DRB1*1101, DRB1*1301, and DRB1*1501). This set of alleles was also used in the pioneering MHCII binding risk-reduction work of de Groot and Martin. We convert the binding affinities into z-scores for each allele using the mean and standard deviation of affinities predicted for a large reference set of 15mers randomly selected from the human protein sequences stored in UniProt.

We take the median z-score across alleles for each 15mer, and sum the positive median z-scores across the sequence to get the final MHCII binding score. The median is an appropriate aggregation because a peptide fragment that binds several MHCII variants poses an immunogenic risk to a larger population of patients than a fragment that binds to only one. Dhanda et al., creators of the protein deimmunization engine on the IEDB website, also aggregate MHCII binding scores across alleles using the median. We ignore negative scores in our sum across the sequence because peptides that certainly don't bind to MHCII (large negative scores) should not offset peptides that bind MHCII tightly (large positive score). The fraction of putative MHC binding peptides for all unique 15mers in each sequence were determined. The low-immunogenicity set (GAN −I) has fewer MHCII-binding peptides than other sets, suggesting the GAN learns which 15mers to avoid regardless of our sequence-score abstraction.

Structure Modeling, Calculated Isoelectric Point (pI), and Negative Patch Surface Area Structure models were calculated as Fab structures using the antibody modeling tool within the Molecular Operating Environment (MOE, Chemical Computing Group, Montreal, Canada). Fab structures were used rather than Fvs in order to generate more accurate Fv surface patches in the presence of constant domains. The pIs were calculated using the Ensemble Isoelectric Point method in the Protein Properties tool within MOE called as an SVL method. The electronegative patch sizes were calculated using the Protein Patches method as an SVL call within MOE with the Hydrophobic Min Area (p_hminarea) changed from the default setting of 50 to 30 $Å^2$ and the Charge Cutoff (p_qcutoff) changed from the default setting of 40 to 20 $Å^2$.

GAN-Library Sequence Selection

Human repertoire contains a small subset of sequences which have missing residues, non-standard cystines, non-standard N-linked glycosylation sites, or potential N-linked glycosylation sites. Sequences with these properties were not pulled from the training set and are therefore also represented by a small subset in the GAN libraries. For our phage library, we filtered out any sequences generated by the GAN which had any of these properties, before selecting final sequences.

Phage Expression of GAN-Library

Bacterial Strains

Escherichia coli One Shot™ TOP10 cells (F-mcrA Δ(mrr-hsdRMS-mcrBC) Φ80lacZΔM15 Δ lacX74 recA1 araD139 Δ(araleu)7697 galU galK rpsL (StrR) endA1 nupG) were purchased from Thermo Fisher Scientific and used for phagemid DNA cloning. E. Cloni® 10G electrocompetent cells (F-mcrA Δ(mrr-hsdRMS-mcrBC) endA1 recA1 Φ80dlacZΔM15 ΔlacX74 araD139 Δ(ara,leu)7697galU galK rpsL nupG λ– tonA (StrR)) were purchased from Lucigen Corporation and were also used for phagemid DNA cloning. E. coli SS520 electrocompetent cells (F'[proAB lacI$^q$Z ΔM15 Tn10 (Tet$^R$)] araD139 Δ(ara-leu)7696 galE15 galK16 Δ(lac)X74 rpsL (Str$^R$) hsdR2 ($r_K$–$m_K$+) mcrA merB1) were purchased from Lucigen Corporation and used as the host for phage library production.

Cloning

The phagemid pADL-20c (Antibody Design Labs) was used for construction of the GAN sub-libraries and was modified for expression of Fab antibody fragments as N-terminal pIII fusion proteins in E. coli. This vector utilizes the bacterial pectate lysate (pelB) signal sequences for periplasmic translocation of fusion proteins, along with an ampicillin resistance gene for growth and selection in transformed E. coli. A hexahistidine tag and a FLAG tag was added to the C-terminus of the CH1 and kappa constant domains, respectively, and the amber stop codon upstream of gIII was removed to allow expression of the fusion protein in SS520 host cells.

Synthetic gene fragments encoding variable heavy and light chains were first amplified individually using PCR primers containing 22 base pairs of sequence complementary to the phagemid backbone. Next, PCRs were pooled by germline and assembled sequentially into the phagemid using NEBuilder® HiFi DNA Assembly Master Mix (New England Biolabs). Transformations were performed using One Shot™ TOP10 or E. cloni 10G® cells, and the resulting phagemid DNA was purified using ZymoPURE™ II Plasmid Midiprep Kit (Zymo Research).

Phage Library Production

E. coli SS520 host cells were electroporated as described by the manufacturer using 250 ng of each sub-library DNA. An aliquot of each transformation was plated on 2×YT agar plates supplemented with 100 µg/mL carbenicillin and 2% glucose and incubated overnight at 30° C. The resulting colonies were used for estimating library size and for sequencing the variable heavy and light chains using colony PCR. The remainder of the transformation was used to inoculate 2×YT-CG (2×YT broth containing 50 µg/mL carbenicillin and 2% glucose) at an $OD_{600\ nm}$ of 0.07 and incubated with shaking at 250 rpm and 37° C. until an $OD_{600\ nm}$~0.5. The cultures were then infected with M13KO7 helper phage (Antibody Design Labs) at a multiplicity of infection (MOI) of 25 and incubated at 37° C. without shaking for 30 minutes, followed by shaking at 200 rpm for 30 minutes. Cultures were centrifuged followed by medium replacement in 2×YT-CK (2×YT supplemented with 50 µg/mL carbenicillin and 25 µg/mL kanamycin). After overnight incubation at 30° C. and 200 rpm, the phage particles were purified and concentrated by PEG/NaCl precipitation and resuspended in PBS containing 0.5% BSA and 0.05% Tween-20. Phage concentration was determined using a spectrophotometer, assuming 1 unit at OD is equivalent to $5×10^{12}$ phage/mL. PEG-precipitated phage from each GAN sub-library was normalized to $1×10^{13}$ phage/mL and serially diluted 10-fold in 2% non-fat dry milk in PBS, in duplicate, for use in the polyclonal phage ELISA.

Monoclonal Phage Production

Single clones harboring a functional Fab fusion protein were inoculated into 500 µL 2×YT-CTG (2×YT broth supplemented with 50 µg/mL carbenicillin, 15 µg/mL tetracycline, and 2% glucose) and cultivated in 96 deep-well plates overnight at 37° C. with rigorous shaking. 5 µL of the overnight cultures was then transferred to new deep-well plates containing 100 µL 2×YT-CTG and incubated at 37° C. with rigorous shaking until an $OD_{600\ nm}$~0.5. M13KO7 helper phage was added to each well at MO125, and plates were incubated without agitation at 37° C. for 1 hour before medium replacement to 2×YT-CK and overnight incubation with rigorous shaking at 30° C. Phage supernatants were harvested after centrifugation and diluted 1:1 in 2% non-fat dry milk in PBS for use in the monoclonal phage ELISA.

Phage ELISA

The amount of Fab displayed on phage was determined using ELISA. Briefly, 96-well MaxiSorp® assay plates (Nunc) were coated overnight at 4° C. with anti-human Fab (Millipore Sigma) diluted 1:500 in PBS, then blocked in PBS containing 1% BSA for 1 hour at room temperature (RT). Diluted phage preparations were added and allowed to incubate for 1 hour at RT before captured virions were detected using a 1:5000 dilution of anti-M13-HRP (Santa Cruz Biotechnology) for 1 hour at RT. All interval plate washes were performed 3 times in PBST (PBS supplemented with 0.1% v/v Tween-20). ELISAs were developed by addition of TMB solution (Thermo Fisher Scientific) and quenched using 10% phosphoric acid. Absorbance was read at $A_{450\ nm}$. Phage supernatant from non-transformed *E. coli* SS520 host cells was included as a negative control.

Selected CHO-Expressed Molecules

CHOK1 Glutamine Synthetase (GS) knockout host cells (Horizon Discovery, Cambridge, United Kingdom) were maintained in CD OptiCHO (Thermo Fisher Scientific, Waltham, Mass.) containing 4 mM glutamine. Cells were cultured as previously described.[70]

The light chains (LC) and heavy chains (HC) containing appropriate signal peptides were cloned into an in-house proprietary bicistronic PiggyBac transposon expression vector[70] in a sequential, 2-step manner using Gibson assembly. Successful insertion of the intended coding sequences was confirmed by Sanger DNA sequencing. Plasmid DNA was purified using a conventional silica-based low endotoxin Zymo Research kit (Irvine, Calif.).

Cells, DNA and RNA were added to BTX 25—multi-well electroporation plates (Harvard Bioscience, Holliston, Mass.) using a Tecan Freedom EVO (Mannedorf, Switzerland) liquid handler. For each transfection, 2.4E6 cells were spun down and resuspended in 150 uL of PFCHO medium (Sigma-Aldrich, St. Louis, Mo.). 7.5 ug of DNA and 2.5 ug of pJV95 transposase RNA were added to the cells, then electroporated at 3175 uF capacitance, 290 V voltage, 950 Ω resistance in an ECM 830 electro manipulator coupled to a HT 100 high throughput adaptor (BTX, Holliston, Mass.). Both molecules were transfected in triplicate. Cells were transferred to 2 mLs of non-selective medium in a 24 deep well plate (DWP) shaking at 220 rpm at standard growth conditions and cultured for 2 days prior to selection. After two days, cells were counted on a guava flow cytometer (Luminex, Austin, Tex.); plates were spun down and resuspended in 2 mLs of selective CD OptiCHO medium. Cells were counted and passaged every four to five days thereafter.

Thirteen days after selection started and viability was >90%, cells were seeded into proprietary production medium at 8×105 c/mL in 3 mLs in 24 DWPs under standard growth conditions. On days 3, 6 and 8, cells were fed with 5% of the starting volume with Cell Boost7a and 0.5% Cell Boost7b (Hyclone GE Healthcare Life Sciences). Cell counts and glucose was measured as previously described,[70] On day 8, 50% glucose was supplemented to a final concentration of approximately 10 g/L. On day 10, cells were counted, spun down and filtered by centrifugation onto 24-deep well filter plates (Thomson, Oceanside, Calif.). Titer was sampled by Ultra High-Performance Liquid Chromatography (UHPLC) Protein A affinity. Replicate wells were pooled together for Protein A purification.

Biophysical Validation of CHO-Expressed Molecules

Sample Preparation

Samples were buffer exchanged against 10 diavolumes of 20 mM sodium chloride, 150 mM sodium chloride, pH 7.1 (PBS) using a centrifugal filter with a 30 kDa molecular weight cut off (Amicon). After buffer exchange, samples were normalized to 1 mg/mL using a Lunatic protein concentration plate format instrument (Unchained Labs).

Differential Scanning Fluorimetry

Thermal transition temperature(s) and weighted shoulder scores were determined by DSF according to the method previously described (Kerwin, 2019).

Self Interaction Nanoparticle Spectroscopy

SINS measurements were performed according to the method previously described (Liu, 2013) Briefly, gold nanoparticles (Ted Pella) were conjugated overnight with an 80:20 ratio of anti-human and anti-goat antibodies (Jackson Immuno Research). Unreacted sites were blocked using an aqueous 0.1% (w/v) polysorbate 20 solution. Conjugated gold nanoparticles were then concentrated by centrifugation and removal of 95% of the supernatant. Analysis was carried out in PBS (20 mM phosphate, 150 mM NaCl, pH 7.1) at a protein concentration of 0.05 mg/mL reacted with 5 ul of concentrated conjugated gold nanoparticles. After a 2 hour incubation, absorbance spectrum from 400-600 nm was collected using a Spectrostar Nano plate reader at 2 nm steps. The wavelength maximum of the spectrum peak is reported.

Relative Solubility

Solubility was assessed according to the method previously described (Kerwin, 2019). Analysis was done in PBS buffer (20 mM sodium phosphate and 150 mM sodium chloride pH 7.1) and a final PEG 10,000 concentration ranging from 0% to 12%. Remaining soluble protein after PEG incubation is reported.

Size Exclusion High Performance Liquid Chromatography

Size exclusion high performance liquid chromatography (SEC) was performed on a Dionex UltiMate 3000 HPLC System using a Waters XBridge Protein BEH SEC 200 Å, 3.5 μm column and a diode array detector collecting at 280 nm. Separation was achieved under native conditions with a 100 mM sodium phosphate, 250 mM sodium chloride, 10% acetonitrile v/v mobile-phase buffer at pH 6.8.

What is claimed is:

1. A method comprising:
   generating, by a computing system including one or more computing devices having one or more processors and memory and using a generative adversarial network, a plurality of first amino acid sequences, individual first amino acid sequences of the plurality of first amino acid sequences corresponding to antibody light chains;
   generating, by the computing system and using the generative adversarial network, a plurality of second amino acid sequences, individual second amino acid sequences of the plurality of second amino acid sequences corresponding to antibody heavy chains;
   combining, by the computing system and using the generative adversarial network, a first amino acid sequence of the plurality of first amino acid sequences with a second amino acid sequence of the plurality of second amino acid sequences to produce a third amino acid sequence, the third amino acid sequence corresponding to an antibody including a light chain corresponding to the first amino acid sequence and a heavy chain corresponding to the second amino acid sequence; and
   analyzing, by the computing system and using the generative adversarial network, the third amino acid sequence with respect to an additional plurality of amino acid sequences to produce an output, the additional plurality of amino acid sequences being included in training data for the generative adversarial network and the output indicating a measure of similarity between the third amino acid sequence and at least a portion of the additional plurality of amino acid sequences.

2. The method of claim 1, wherein combining the first amino acid sequence with the second amino acid sequence includes concatenating the second amino acid sequence to the first amino acid sequence.

3. The method of claim 1, wherein:
   the generative adversarial network includes a first generating component that implements a first model to generate the plurality of first amino acid sequences and a second generating component that implements a second model to generate the plurality of second amino acid sequences;

the first model includes a first function having one or more first variables and one or more first weights; and the second model includes a second function different from the first function, the second function including one or more second variables and one or more second weights.

4. The method of claim 3, wherein the third amino acid sequence is analyzed by a discriminator and the output is provided to at least one of the first generating component or the second generating component.

5. The method of claim 4, wherein the first generating component modifies the first model based on the output.

6. The method of claim 4, wherein the second generating component modifies the second model based on the output.

7. The method of claim 1, wherein the first amino acid sequence includes at least a portion of a first variable region of an antibody light chain and the second amino acid sequence includes at least a portion of a first variable region of an antibody heavy chain.

8. The method of claim 1, wherein the first amino acid sequence includes at least a portion of a first variable region and a first constant region of an antibody light chain and the second amino acid sequence includes at least a portion of a second variable region and a second constant region of an antibody heavy chain.

9. The method of claim 3, comprising:

determining, by the computing system and based on the output, that training of the first model is complete such that the first model is a first trained model;

determining, by the computing system and based on the output, that training of the second model is complete such that the second model is a second trained model;

generating, by the computing system and using the first trained model, a first additional amino acid sequence of an additional light chain of an antibody;

generating, by the computing system and using the second trained model, a second additional amino acid sequence of an additional heavy chain of an antibody; and combining, by the computing system, the first additional amino acid sequence and the second additional amino acid sequence to produce a third additional amino acid sequence, the third additional amino acid sequence including a light chain and a heavy chain of an additional antibody.

10. The method of claim 9, comprising evaluating, by the computing system, the third additional amino acid sequence with respect to one or more metrics, the one or more metrics including at least one of a number of hydrophobic amino acids included in the third additional amino acid sequence, a number of positively charged amino acids included in the third additional amino acid sequence, a number of negatively charged amino acids included in the third additional amino acid sequence, a number of uncharged amino acids included in the third additional amino acid sequence, a level of expression of the third additional amino acid sequence, a melting temperature of the third additional amino acid sequence, or a level of self-aggregation of the third additional amino acid sequence.

11. The method of claim 9, comprising analyzing, by the computing system and using the generative adversarial network, the third additional amino acid sequence with respect to a further plurality of amino acid sequences to produce an additional output, wherein:

the further plurality of amino acid sequences is included in additional training data for the generative adversarial network;

the additional training data includes different amino acid sequences of antibodies than the additional plurality of amino acid sequences included in the training data; and the additional output indicates an additional measure of similarity between the third additional amino acid sequence and at least a portion of the further plurality of amino acid sequences.

12. A system comprising:

one or more hardware processors; and one or more non-transitory computer readable media storing computer-executable instructions that, when executed by the one or more hardware processors, cause the one or more processor to perform operations comprising:

training a first model of a first generating component of a generative adversarial network using a first training dataset including a first number of amino acid sequences of light chains of antibodies to produce a first trained model;

training a second model of a second generating component of the generative adversarial network using a second training dataset including a second number of amino acid sequences of heavy chains of antibodies to produce a second trained model, wherein training the second generating component proceeds at a first rate that is different from a second rate of training the first generating component;

generating, using the first generating component, a first additional number of first additional amino acid sequences corresponding to antibody light chains;

generating, using the second generating component, a second additional number of second additional acid sequences corresponding to antibody heavy chains; and combining, using the generative adversarial network, a first amino acid sequence of the first additional number of first additional amino acid sequences with a second amino acid sequence of the second additional number of second additional amino acid sequences to produce a third amino acid sequence, the third amino acid sequence corresponding to an antibody including a light chain corresponding to the first amino acid sequence and a heavy chain corresponding to the second amino acid sequence.

13. The system of claim 12, wherein the second generating component is trained using a number of hobbled weights to decrease a rate of training the second generating component relative to an additional rate of training the second generating component without the number of hobbled weights.

14. The system of claim 12, wherein the second generating component is trained by slowing a gradient of the second generating component.

15. The system of any one of claim 12 wherein the one or more non-transitory computer readable media store additional computer-executable instructions that, when executed by the one or more hardware processors, cause the one or more processors to perform additional operations comprising:

training the second generating component during a first period of time;

determining that a first plurality of amino acid sequences produced during an end portion of the first period of time have a first level of quality;

training the first generating component for a second period of time that includes the first period of time and is longer than the first period of time;

determining that a second plurality of amino acid sequences produced during an end portion of the second period of time have the first level of quality;

training the second generating component during a third period of time that is subsequent to the second period of time;

determining that a third plurality of amino acid sequences produced during an end portion of the third period of time have a second level of quality;

training the first generating component for a fourth period of time that includes the third period of time and is longer than the third period of time; and determining that a fourth plurality of amino acid sequences produced during an end portion of the fourth period of time has the second level of quality.

16. The system of claim 15, wherein a total amount of time elapsed to train the second generating component is less than a total amount of time elapsed to train the first generating component.

* * * * *